(12) United States Patent
Ng et al.

(10) Patent No.: US 9,234,180 B2
(45) Date of Patent: Jan. 12, 2016

(54) METHOD FOR INDUCING PLURIPOTENCY IN HUMAN SOMATIC CELLS WITH PRDM14 OR NFRKB

(75) Inventors: Huck Hui Ng, Singapore (SG); Na Yu Chia, Singapore (SG); Bo Feng, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

(21) Appl. No.: 13/701,437

(22) PCT Filed: Jun. 2, 2011

(86) PCT No.: PCT/SG2011/000202
§ 371 (c)(1),
(2), (4) Date: Nov. 30, 2012

(87) PCT Pub. No.: WO2011/152798
PCT Pub. Date: Dec. 8, 2011

(65) Prior Publication Data
US 2013/0078720 A1    Mar. 28, 2013

Related U.S. Application Data

(60) Provisional application No. 61/350,843, filed on Jun. 2, 2010.

(51) Int. Cl.
*C12N 5/071* (2010.01)
*C12N 5/074* (2010.01)

(52) U.S. Cl.
CPC .......... *C12N 5/0696* (2013.01); *C12N 2501/60* (2013.01); *C12N 2501/602* (2013.01); *C12N 2501/603* (2013.01); *C12N 2501/604* (2013.01); *C12N 2501/606* (2013.01); *C12N 2506/1307* (2013.01); *C12N 2510/00* (2013.01)

(58) Field of Classification Search
None
See application file for complete search history.

(56) References Cited

U.S. PATENT DOCUMENTS

2009/0047263 A1* 2/2009 Yamanaka et al. ......... 424/93.21
2011/0286978 A1* 11/2011 Klimanskaya et al. .... 424/93.21

FOREIGN PATENT DOCUMENTS

| GB | 2450603 | 12/2008 |
| WO | WO 2009/067563 | 5/2009 |
| WO | WO 2009/136867 | 11/2009 |
| WO | WO 2009/157201 | 12/2009 |
| WO | WO 2010/017562 | 2/2010 |

OTHER PUBLICATIONS

Takahashi (A) et al. "Induction of pluripotent stem cells from mouse embryonic and adult fibroblast cultures by defined factors ." Cell. Aug. 25, 2006;126(4):663-76. Epub Aug. 10, 2006.*

Yamanaka et al. "Induction of pluripotent stem cells from mouse fibroblasts by four transcription factors." Cell Prolif. 2008, 41 (Suppl. 1), pp. 51-56.*
Stadtfeld et al. "Induced Pluripotent Stem Cells Generated Without Viral Integration." Science (2008), 7: pp. 945-949.*
Kim et al. "Direct reprogramming of mouse fibroblasts to neural progenitors." Proc Natl Acad Sci U S A. May 10, 2011;108(19):7838-43.*
Takahashi (B) et al. "Induction of Pluripotent Stem Cells from Adult Human Fibroblasts by Defined Factors." Cell (2007), 131; pp. 861-872.*
Tsuneyoshi et al. "PRDM14 suppresses expression of differentiation marker genes in human embryonic stem cells." Biochem Biophys Res Commun. 2008, 21;367(4): pp. 899-905.*
Extended European Search Report mailed Feb. 18, 2015 for Application No. EP11790096.9.
Chia, et al., "A genome-wide RNAi screen reveals determinants of human embryonic stem cell identity," Nature 2010, 468(7321):316-20.
International Search Report and Written Opinion mailed Aug. 18, 2011 in corresponding PCT application No. PCT SG2011/000202.
International Preliminary Report on Patentability issued on Dec. 4, 2012 in corresponding PCT application No. PCT/SG2011/000202.
Adams et al., "Localization of the gene encoding R kappa B (NFRKB, a tissue-specific DNA binding protein, to chromosome 11q24-q25", Genomics, 1992, pp. 270-274, vol. 14.
Albright et al., "TAFs revisited: more data reveal new twists and confirm old ideas", Gene., 2000, pp. 1-13, vol. 242.
Altschul et al., "Basic local alignment search tool", Journal of Molecular biology, 1990, pp. 403-410, vol. 215 No. 3.
Assou et al., "A meta-analysis of human embryonic stem cells transcriptome integrated into a web-based expression atlas", Stem Cells, 2007, pp. 961-973, vol. 25.
Badis et al., "Diversity and complexity in DNA recognition by transcription factors", Science, 2009, pp. 1720-1723, vol. 324.
Bailey et al., "Meme Suite: tools for motif discovery and searching", Nucleic Acids Res., 2009, pp. W202-W208, vol. 37 (Web Server issue).
Bowles et al., "Phylogeny of the Sox family of developmental transcription factors based on sequence and structural indicators", Dev Biol., 2000, pp. 239-255, vol. 227.
Boyer et al., "Core transcriptional regulatory circuitry in human embryonic stem cells", Cell, 2005, pp. 947-956, vol. 122.
Brons et al., "Derivation of pluripotent epiblast stem cells from mammalian embryos", Nature, 2007, pp. 191-195, vol. 448.
Casamassimi et al., "Mediator complexes and eukaryotic transcription regulation: an overview", Biochimie, 2007, pp. 1439-1446, vol. 89.

(Continued)

*Primary Examiner* — Thaian N Ton
*Assistant Examiner* — Titilayo Moloye
(74) *Attorney, Agent, or Firm* — Wolf, Greenfield & Sacks, P.C.

(57) ABSTRACT

Methods of inducing pluripotency in human somatic cells and methods of maintaining pluripotency in human embryonic stem cells (hESCs) are provided, as well as cells and uses of employing such cells. The methods comprise culturing cells in the presence of (i) OCT4 and SOX2; (ii) at least one of KLF4 and c-MYC; and at least one of PRDM14 and NFRKB.

19 Claims, 69 Drawing Sheets

(56) References Cited

OTHER PUBLICATIONS

Chambers et al., "Functional expression cloning of Nanog, a pluripotency sustaining factor in embryonic stem cells", Cell, 2003, pp. 643-655, vol. 113.
Chambers et al., "Nanog safeguards pluripotency and mediates germline development", Nature, 2007, pp. 1230-1234, vol. 450.
Chamovitz et al., "Revisiting the COP9 signalosome as a transcriptional regulator", EMBO Rep., 2009, pp. 352-358, vol. 10.
Chen et al., "Integration of external signaling pathways with the core transcriptional network in embryonic stem cells", Cell, 2008, pp. 1106-1117, vol. 133.
Chew et al., "Reciprocal transcriptional regulation of Pou5f1 and Sox2 via the Oct4/Sox2 complex in embryonic stem cells", Mol. Cell. Biol., 2005, pp. 6031-6046, vol. 25.
Conaway et al., "The INO80 chromatin remodeling complex in transcription, replication and repair", Trends Biochem. Sci., 2009, pp. 71-77, vol. 34.
D'Amour et al., "Efficient differentiation of human embryonic stem cells to definitive endoderm", Nat. Biotechnol., 2005, pp. 1534-1541, vol. 23.
Derunes et al., "Characterization of the PR domain of RIZ1 histone methyltransferase", Biochem. Biophys. Res. Commun., 2005, pp. 925-934, vol. 333.
Dettman et al., "The zinc finger SET domain gene Prdm14 is overexpressed in lymphoblastic lymphomas with retroviral insertions at Evi32", PLoS One, 2008, p. e3823, vol. 3 No. 11.
Dimos et al., "Induced pluripotent stem cells generated from patients with ALS can be differentiated into motor neurons", Science, 2008, pp. 1218-1221, vol. 321.
Ding et al., "A genome-scale RNAi screen for Oct4 modulators defines a role of the Paf1 complex for embryonic stem cell identity", Cell Stem Cell, 2009, pp. 403-415, vol. 4.
Evans et al., "Establishment in culture of pluripotential cells from mouse embryos", Nature, 1981, pp. 154-156, vol. 292.
Evans et al., "Kruppel-like factor 4 is acetylated by p300 and regulates gene transcription via modulation of histone acetylation", J. Biol. Chem., 2007, p. 1074, vol. 10.
Fazzio et al., "An RNAi screen of chromatin proteins identifies Tip60-p400 as a regulator of embryonic stem cell identity", Cell, 2008, pp. 162-174, vol. 134.
Fumasoni et al., "Family expansion and gene rearrangements contributed to the functional specialization of PRDM genes in vertebrates", BMC Evol. Biol., 2007, p. 187, vol. 7.
Hanna et al., "Metastable pluripotent states in NOD-mouse-derived ESCs", Cell Stem Cell, 2009, pp. 513-524, vol. 4.
Heintzman et al., "Histone modifications at human enhancers reflect global cell-type-specific gene expression", Nature, 2009, pp. 108-112, vol. 459.
Hockemeyer et al., "A drug-inducible system for direct reprogramming of human somatic cells to pluripotency", Cell Stem Cell, 2008, pp. 346-353, vol. 3.
Hu et al., "A genome-wide RNAi screen identifies a new transcriptional module required for self-renewal", Genes Dev., 2009, pp. 837-848, vol. 23.
Huang et al., "Histone methyltransferases, diet nutrients and tumour suppressors", Nat. Rev. Cancer, 2002, pp. 469-476, vol. 2.
Ivanova et al., "Dissecting self-renewal in stem cells with RNA interference", Nature, 2006, pp. 533-538, vol. 442.
Jackson et al., "The mechanism of eukaryotic translation initiation and principles of its regulation", Nat. Rev. Mol. Cell. Biol., 2010, pp. 113-127, vol. 11.
Joshi-Tope et al., "Reactome: a knowledgebase of biological pathways", Nucleic Acids Res., 2005, pp. D428-D432, vol. 33.
Kim et al., "An extended transcriptional network for pluripotency of embryonic stem cells", Cell, 2008, pp. 1049-1061, vol. 132.
Lister et al., "Human DNA methylomes at base resolution show widespread epigenomic differences", Nature, 2009, pp. 315-322, vol. 462.

Loh et al., "The Oct4 and Nanog transcription network regulates pluripotency in mouse embryonic stem cells", Nat. Genet., 2006, pp. 431-440, vol. 38.
Lowry et al., "Generation of human induced pluripotent stem cells from dermal fibroblasts", Proc. Natl. Acad. Sci. USA, 2008, pp. 2883-2888, vol. 105.
Lu et al., "Defined culture conditions of human embryonic stem cells", PNAS, 2006, pp. 5688-5693, vol. 103 No. 15.
Maehr et al., "Generation of pluripotent stem cells from patients with type 1 diabetes", Proc. Natl. Acad. Sci. USA, 2009, pp. 15768-15773, vol. 106.
Martin, "Isolation of a pluripotent cell line from early mouse embryos cultured in medium conditioned by teratocarcinoma stem cells", Proc. Natl. Acad. Sci. USA, 1981, pp. 7634-7638, vol. 78.
Matys et al., "TRANSFAC® and its module TRANSCompel®: transcriptional gene regulation in eukaryotes", Nucleic Acids Res., 2006, pp. D108-D110, vol. 34 (Database issue).
Mi et al., "The Panther database of protein families, subfamilies, functions and pathways", Nucleic Acids Res., 2005, pp. D284-D288, vol. 33 (Database issue).
Mitsui et al., "The homeoprotein Nanog is required for maintenance of pluripotency in mouse epiblast and ES cells", Cell, 2003, pp. 631-642, vol. 113.
Nakagawa et al., "Generation of induced pluripotent stem cells without Myc from mouse and human fibroblasts", Nat. Biotechnol., 2008, pp. 101-106, vol. 26.
Needleman et al., "A general method applicable to the search for similarities in the amino acid sequence of two proteins", Journal of Molecular Biology, 1970, pp. 443-453, vol. 48 No. 3.
Nichols et al., "Formation of pluripotent stem cells in the mammalian embryo depends on the POU transcription factor Oct4", Cell, 1998, pp. 379-391, vol. 95.
Niwa et al., "Quantitative expression of Oct-3/4 defines differentiation, dedifferentiation or self-renewal of ES cells", Nat. Genet., 2000, pp. 372-376, vol. 24.
Nordhoff et al., "Comparative analysis of human, bovine, and murine Oct-4 upstream promoter sequences", Mamm Genome, 2001, pp. 309-317, vol. 12.
Park et al., "Disease-specific induced pluripotent stem cells", Cell, 2008, pp. 877-886, vol. 134.
Park et al., "Reprogramming of human somatic cells to pluripotency with defined factors", Nature, 2008, pp. 141-146, vol. 451.
Pearson et al., "Improved tools for biological sequence comparison", Proc. Natl. Acad. Sci. USA, 1988, p. 2444, vol. 85.
Raya et al., "Disease-corrected haematopoietic progenitors from Fanconi anaemia induced pluripotent stem cells", Nature, 2009, pp. 53-59, vol. 460.
Richards et al., "The transcriptome profile of human embryonic stem cells as defined by SAGE", Stem Cells, 2004, pp. 51-64, vol. 22.
Rino et al., "The spliceosome: a self-organized macromolecular machine in the nucleus?", Trends Cell Biol., 2009, pp. 375-384, vol. 19.
Ryan et al., "POU domain family values: flexibility, partnerships, and developmental codes", Genes & Dev., 1997, pp. 1207-1225, vol. 11.
Scholer et al., "New type of POU domain in germ line-specific protein Oct-4", Nature, 1990, pp. 435-439, vol. 344.
Scholer et al., "Oct-4: a germline-specific transcription factor mapping to the mouse t-complex", EMBO J, 1990, pp. 2185-2195, vol. 9.
Sharov et al., "Exhaustive search for over-represented DNA sequence motifs with CisFinder", DNA Res., 2009, pp. 261-273, vol. 16.
Silva et al., "Nanog is the gateway to the pluripotent ground state", Cell, 2009, pp. 722-737, vol. 138.
Sun et al., "Cross-species transcriptional profiles establish a functional portrait of embryonic stem cells", Genomics, 2007, pp. 22-35, vol. 89.
Takeda et al., "Human Oct3 gene family: cDNA sequences, alternative splicing, gene organization, chromosomal location, and expression at low levels in adult tissues", Nucleic Acids Res., 1992, pp. 4613-4620, vol. 20.
Tesar et al., "New cell lines from mouse epiblast share defining features with human embryonic stem cells", Nature, 2007, pp. 196-199, vol. 448.

(56) References Cited

OTHER PUBLICATIONS

Thomson et al., "Embryonic stem cell lines derived from human blastocysts", Science, 1998, pp. 1145-1147, vol. 282.

Tsubooka et al., "Roles of Sall4 in the generation of pluripotent stem cells from blastocysts and fibroblasts", Genes Cells, 2009, pp. 683-694, vol. 14.

Tusher et al., "Significance analysis of microarrays applied to the ionizing radiation response", Proc. Natl. Acad. Sci. USA, 2001, pp. 5116-5121, vol. 98.

Valuer et al., "Signaling pathways controlling pluripotency and early cell fate decisions of human induced pluripotent stem cells", Stem Cells, 2009, pp. 2655-2666, vol. 27.

Watanabe et al., "A ROCK inhibitor permits survival of dissociated human embryonic stem cells", Nat. Biotechnol., 2007, pp. 681-686, vol. 25.

Wegner et al., "From head to toes: the multiple facets of Sox proteins", Nucleic Acid Res., 1999, pp. 1409-1420, vol. 27.

Wei et al., "Transcriptome profiling of human and murine ESCs identifies divergent paths required to maintain the stem cell state", Stem Cells, 2005, pp. 166-185, vol. 23.

Xu et al., "BMP4 initiates human embryonic stem cell differentiation to trophoblast", Nat. Biotechnol., 2002, pp. 1261-1264, vol. 20.

Xu et al., "Feeder-free growth of undifferentiated human embryonic stem cells", Nat. Biotechnol., 2001, pp. 971-974, vol. 19.

Xu et al., "Nanog is a direct target of TGFbeta/activin-mediated SMAD signaling in human ESCs", Cell Stem Cell, 2008, pp. 196-206, vol. 3.

Yamaji et al., "Critical function of Prdm14 for the establishment of the germ cell lineage in mice", Nat. Genet., 2008, pp. 1016-1022, vol. 40.

Yeom et al., "Germline regulatory element of Oct-4 specific for the totipotent cycle of embryonal cells", Development, 1996, pp. 881-894, vol. 122.

Ying et al., "The ground state of embryonic stem cell self-renewal", Nature, 2008, pp. 519-523, vol. 453.

Yu et al., "Induced pluripotent stem cell lines derived from human somatic cells", Science, 2007, pp. 1917-1920, vol. 318.

Yu et al., "Pluripotent stem cell lines", Genes Dev., 2008, pp. 1987-1997, vol. 22.

Zhang et al., "Model-based analysis of ChIP-Seq (MACS)", Genome Biol., 2008, p. R137, vol. 9.

Zhao et al., "Two supporting factors greatly improve the efficiency of human iPSC generation", Cell Stem Cell, 2008, pp. 475-479, vol. 3.

\* cited by examiner

Bars = 50 μm

| Gene | Ranking (% of 21,121 genes) | References |
|---|---|---|
| POU5F1 | 1 (0.005%) | |
| HCFC1 | 32 (0.15%) | (Dejosez et al, 2008. Cell) |
| TCL1A | 145 (0.69%) | (Ivanova et al, 2006. Nature) |
| ZSCAN10 | 187 (0.89%) | (Wang et al, 2007. Stem Cells) |
| ZIC3 | 844 (3.99%) | (Lim et al, 2007. MBC) |
| NANOG | 873 (4.13%) | (Chambers et al, 2003. Cell) |
| ZNF143 | 1024 (4.85%) | (Chen et al, 2008. Stem Cells) |
| RIF1 | 1350 (6.39%) | (Loh et al, 2006. Nat Genet) |

FIG. 3A

| Gene | Refseq ID | Ranking (% of 21,121 genes) |
|---|---|---|
| MED1 | NM_004774 | Top 10% |
| MED4 | NM_014166 | Top 10% |
| MED6 | NM_005466 | Top 10% |
| MED7 | NM_004270 | Top 10% |
| MED8 | NM_201542 | >25% |
| MED9 | NM_01819 | >25% |
| MED10 | NM_032286 | 10% to 25% |
| MED11 | NM_001001683 | >25% |
| MED12 | NM_005120 | Top 10% |
| MED12L | NM_053002 | >25% |
| MED13 | NM_005121 | Top 10% |
| MED13L | NM_015335 | Top 10% |
| MED14 | NM_004229 | Top 10% |
| MED15 | NM_001003891 | 10% to 25% |
| MED16 | NM_005481 | >25% |
| MED17 | NM_004268 | Top 10% |
| MED18 | NM_017638 | >25% |
| MED19 | NM_153450 | Top 10% |
| MED20 | NM_004275 | Top 10% |
| MED21 | NM_004264 | >25% |
| MED22 | NM_181491 | >25% |
| MED23 | NM_015979 | >25% |
| MED24 | NM_014815 | Top 10% |
| MED25 | NM_030973 | >25% |
| MED26 | NM_004831 | Top 10% |
| MED27 | NM_004269 | 10% to 25% |
| MED28 | NM_025205 | Top 10% |
| MED29 | NM_017592 | 10% to 25% |
| MED30 | NM_080651 | 10% to 25% |
| MED31 | NM_016060 | >25% |

FIG. 3B

| Gene | Alternative name | Ranking (% of 21,121 genes) |
|---|---|---|
| INO80 | | 10% to 25% |
| ACTB | | >25% |
| ACTL6A | Baf53a | >25% |
| ACTR5 | | Top 10% |
| ACTR8 | | Top 10% |
| RUVBL1 | | >25% |
| RUVBL2b | Tip49 | >25% |
| INO80B | | >25% |
| INO80C | | 10% to 25% |
| YY1 | | Top 10% |
| UCHL5 | | >25% |
| INO80G | NFRKB | Top 10% |
| INO80Q | MCRS1 | Top 10% |
| INO80F | TFPT | Top 10% |
| INO80D | FLJ20309 | >25% |
| INO80E | CCDC95 | Top 10% |

FIG. 3C

| TF family | TRANSFAC PWM | p-value |
|---|---|---|
| FXR | V_PXR_Q2 | 3.27E-12 |
| OCT | V_OCT4_01 | 3.61E-12 |
| ETS | V_ETS1_B | 3.88E-12 |
| WHN | V_WHN_B | 5.44E-12 |
| EGR | V_EGR3_01 | 5.73E-12 |
| AP2 | V_AP2ALPHA_01 | 6.37E-12 |
| E2F | V_E2F_Q6_01 | 6.49E-12 |
| NRF | V_NRF1_Q6 | 7.21E-12 |
| ZF5 | V_ZF5_B | 7.64E-12 |
| SP1 | V_SP1_Q6 | 7.66E-12 |
| WT1 | V_WT1_Q6 | 7.67E-12 |
| HIC1 | V_HIC1_02 | 8.29E-12 |
| ZNF219 | V_ZNF219_01 | 8.48E-12 |
| MOVO | V_MOVOB_01 | 9.68E-12 |
| GGG | V_CHCH_01 | 9.92E-12 |
| CREB | V_NRSE_B | 2.72E-10 |
| P300 | V_P300_01 | 1.26E-09 |
| VMYB | V_VMYB_02 | 1.31E-07 |
| HEN | V_HEN1_02 | 3.36E-07 |
| LEF | V_LEF1_Q2_01 | 3.68E-05 |

| TF family | TRANSFAC PWM | p-value |
|---|---|---|
| BARBIE | V_BARBIE_01 | Not significant, p>0.05 |
| BLIMP1 | V_BLIMP1_Q6 | Not significant, p>0.05 |
| BRCA | V_BRCA_01 | Not significant, p>0.05 |
| CHOP | V_CHOP_01 | Not significant, p>0.05 |
| GFI | V_GFI1_Q6 | Not significant, p>0.05 |
| HSF | V_HSF_Q6 | Not significant, p>0.05 |
| POLYA | V_LPOLYA_B | Not significant, p>0.05 |
| LYF1 | V_LYF1_01 | Not significant, p>0.05 |
| P53 | V_P53_DECAMER_Q2 | Not significant, p>0.05 |
| RP58 | V_RP58_01 | Not significant, p>0.05 |

FIG. 20C

METHOD FOR INDUCING PLURIPOTENCY IN HUMAN SOMATIC CELLS WITH PRDM14 OR NFRKB

CROSS-REFERENCE TO RELATED APPLICATION

The present application is a national stage filing under 35 U.S.C. §371 of international PCT application, PCT/SG2011/000202, filed Jun. 2, 2011, which claims priority under 35 U.S.C. §119(e) to U.S. provisional application, U.S. Ser. No. 61/350,843, filed Jun. 2, 2010; each of which is incorporated herein by reference.

FIELD OF THE INVENTION

The present invention relates to methods for inducing pluripotency in human somatic cells, and for maintaining pluripotency in human embryonic stem cells, with PRDM14 or NFRKB.

BACKGROUND

The derivation of clinically relevant human embryonic stem cells (hESCs) from human blastocysts represents one of the milestones in stem cell biology [1]. hESCs have the capacity for extensive self-renewal under in vitro culture conditions. A second hallmark of these cells is their ability to undergo multi-lineage differentiation; also defined as pluripotency. Hence, the robust self-renewal capability of these pluripotent hESCs makes them a renewable source for the generation of functional cell-types or tissues for potential therapeutic applications and drug discovery. Importantly, hESCs provide an opportunity to study early human developmental biology—an area of study where it is difficult to acquire experimental data.

In addition to the ability to self-renew and differentiate, hESCs share many similarities with mouse embryonic stem cells (mESCs) [2, 3]. Both of them express genes which are associated with pluripotency [4-6]. POU5F1 (coding for the protein OCT4) and NANOG, both key components of the core transcriptional regulatory network [7-9], are highly expressed in undifferentiated ESCs [10-15] and upon differentiation, the expression of these genes is reduced. These and other transcription regulators, including the co-activator p300, show extensive co-localization at genomic sites and this binding configuration may be important for the expression of pluripotency-specific genes [9, 16, 17].

However, there are significant and intriguing differences between hESCs and mESCs. One of the differences is the signaling pathways that promote ESC identity. The fibroblast growth factor/Mitogen-Activated Protein Kinase Kinase (FGF/MEK) pathway is important for the propagation of hESCs. In contrast, stimulation of the FGF/MEK pathway promotes differentiation of mESCs. The inhibition of FGF signaling using specific FGF receptor/MEK inhibitors, in combination with glycogen synthase kinase-3 inhibitor, allows mESCs to be propagated in the absence of other growth promoting molecules [18]. The TGFβ/Activin/Nodal pathway maintains the self-renewal of hESCs but not mESCs, through the up-regulation of NANOG expression [19, 20]. Leukemia inhibitory factor (LIF) and bone morphogenetic protein 4 (BMP4) are known to sustain mESCs, but LIF does not support hESCs and BMP4 induces hESCs to differentiate [4]. Moreover, hESCs and mESCs are morphologically distinct where mESCs form dome-shaped colonies while the hESC colonies are flat. In addition, certain surface molecules like SSEA-3 and SSEA-4 are present in undifferentiated hESCs but not mESCs [4].

The differences between both mouse and human ESCs could be due to species-specific differences in embryonic development. Alternatively, the ESCs could be derived from cells originating from different developmental stages. Consistent with this idea is the identification of post-implantation murine epiblast-derived stem cells which show characteristics of hESCs [21, 22]. Hence, it is useful to understand the differences between these ESCs and the molecular basis for the differences. Furthermore, to harness the full potential of hESCs, it is valuable to dissect the mechanisms that maintain the identity of hESCs.

SUMMARY

The full potential of hESCs in therapeutic and clinical applications requires a detailed understanding of the genetic network that governs the unique properties of hESCs. Previous efforts have focused primarily on murine ESCs, due to the robust nature of their growth and their amenability to animal experimental models. Despite these efforts, little is known about the key players in hESCs.

The present invention provides methods of inducing pluripotency in a human somatic cell, including for example a human fibroblast cell.

In one aspect, the present invention provides a method of inducing pluripotency in a human somatic cell, the method comprising culturing the human somatic cell in the presence of (i) OCT4 and SOX2; (ii) at least one of KLF4 and c-MYC; and (iii) at least one of PRDM14 and NFRKB.

In some embodiments, culturing may comprise contacting the human somatic cell, with the OCT4 and the SOX2, with the at least one of KLF4 and c-MYC and with the at least one of PRDM14 and NFRKB so that the OCT4, the SOX2, the at least one of KLF4 and c-MYC and the at least one of PRDM14 and NFRKB are taken up by the human somatic cell.

In other embodiments, culturing may comprise expressing the OCT4, the SOX2, the at least one of KLF4 and c-MYC and the at least one of PRDM14 and NFRKB in the human somatic cell. Each of OCT4, SOX2, at least one of KLF4 and c-MYC and at least one of PRDM14 and NFRKB may be expressed from one or more expression vectors, which may be viral vectors.

In one embodiment, OCT4, SOX2, KLF4 and PRDM14 are expressed in the human somatic cell.

In another embodiment, OCT4, SOX2, c-MYC and PRDM14 are expressed in the human somatic cell.

In another embodiment, OCT4, SOX2, KLF4, c-MYC and PRDM14 are expressed in the human somatic cell.

In another embodiment, OCT4, SOX2, KLF4 and NFRKB are expressed in the human somatic cell.

In another embodiment, OCT4, SOX2, c-MYC and NFRKB are expressed in the human somatic cell.

In another embodiment, OCT4, SOX2, KLF, c-MYC and NFRKB are expressed in the human somatic cell.

The human somatic cell may be partially differentiated prior to the culturing or may be fully differentiated prior to the culturing. In some embodiments, the human somatic cell is a fibroblast, including a human fibroblast prior to the culturing.

In another aspect, the present invention provides a method of inducing pluripotency in a human fibroblast, the method comprising expressing in the human fibroblast (i) OCT4 and SOX2; (ii) at least one of KLF4 and c-MYC; and (iii) at least one of PRDM14 and NFRKB from one or more expression vectors; and culturing the human fibroblast under conditions suitable for growth of embryonic stem cells.

In another aspect, the present invention provides a method of inducing pluripotency in a human fibroblast, the method comprising expressing in the human fibroblast (i) PRDM14 or NFRKB; together with (ii) OCT4, SOX2 and KLF4. The method may further comprise expressing c-MYC in the human fibroblast.

In another aspect, the present invention provides a human somatic cell comprising (i) OCT4 and SOX2; (ii) at least one of KLF4 and c-MYC; and (iii) at least one of PRDM14 and NFRKB.

In some embodiments, the human somatic cell expresses each of OCT4, SOX2 and KLF4 and at least one of PRDM14 and NFRKB.

In some embodiments, the human somatic cell expresses each of OCT4, SOX2 and c-MYC and at least one of PRDM14 and NFRKB.

In some embodiments, the human somatic cell expresses each of OCT4, SOX2, KLF4 and c-MYC and at least one of PRDM14 and NFRKB.

In some embodiments of the human somatic cell, pluripotency has been induced in the cell.

In some embodiments, the human somatic cell is a fibroblast.

In another aspect, the present invention provides a human somatic cell comprising one or more expression vectors encoding (i) OCT4 and SOX2; (ii) at least one of KLF4 and c-MYC; and (iii) at least one of PRDM14 and NFRKB. In some embodiments, the human somatic cell is a fibroblast, including a human fibroblast.

In another aspect, the present invention provides a human somatic cell, including a human fibroblast cell, produced according to the described methods. The human somatic cell may be one in which pluripotency has been induced.

The present invention further provides methods of maintaining pluripotency of a human embryonic stem cell (hESC). Thus, in another aspect, the present invention provides a method of maintaining pluripotency of a hESC comprising culturing the hESC in the presence of (i) OCT4 and SOX2; (ii) at least one of KLF4 and c-MYC; and (iii) at least one of PRDM14 and NFRKB.

In some embodiments of maintaining pluripotency of a hESC, culturing may comprise contacting the hESC with the OCT4 and the SOX2, with the at least one of KLF4 and c-MYC and with the at least one of PRDM14 and NFRKB so that the OCT4, the SOX2, the at least one of KLF4 and c-MYC and the at least one of PRDM14 and NFRKB are taken up by the hESC.

In other embodiments of maintaining pluripotency of a hESC, culturing may comprise expressing the OCT4, the SOX2, the at least one of KLF4 and c-MYC and the at least one of PRDM14 and NFRKB in the hESC. Each of OCT4, SOX2, at least one of KLF4 and c-MYC and at least one of PRDM14 and NFRKB may be expressed from one or more expression vectors, which may be viral vectors.

Other aspects and features of the present invention will become apparent to those of ordinary skill in the art upon review of the following description of specific embodiments of the invention in conjunction with the accompanying figures.

BRIEF DESCRIPTION OF THE DRAWINGS

In the figures, which illustrate, by way of example only, embodiments of the present invention:

FIG. 3: Gene ontology analysis of $F_{av}$. (3A) Transcription factors that have been shown to be involved in the maintenance of mESC identity. The human counterparts of these genes were identified from this genome wide siRNA screen and they are ranked based on the z-score. The percentage of ranking of these genes out of the 21,121 genes is indicated in bracket. (3B) Components of the mediator complex are identified among the top hits. (3C) Components of the INO80 complex are identified among the top hits.

Anti-GST antibody was used as a control for the anti-HA IP. (14K) 3 copies of CR2 consensus motif identified previously are inserted in tandem before the minimal promoter of the reporter construct. NANOG and PRDM14 expression construct were co-transfected with the reporter construct into 293T cells and luciferase activity was normalized against the control vector. All values are means±s.e.m from 3 independent experiments (n=3). (14L) PRDM14 and NANOG synergistically enhance reprogramming of human fibroblasts. Graph depicts fold change of number of TRA-1-60 positive hiPSC colonies generated from PRDM14 or NANOG in conjunction with OCT4, SOX2 and KLF4 (OSK) with respect to the control (OSK). All values are means±s.e.m from 3 independent experiments (n=3).

Figure 15:
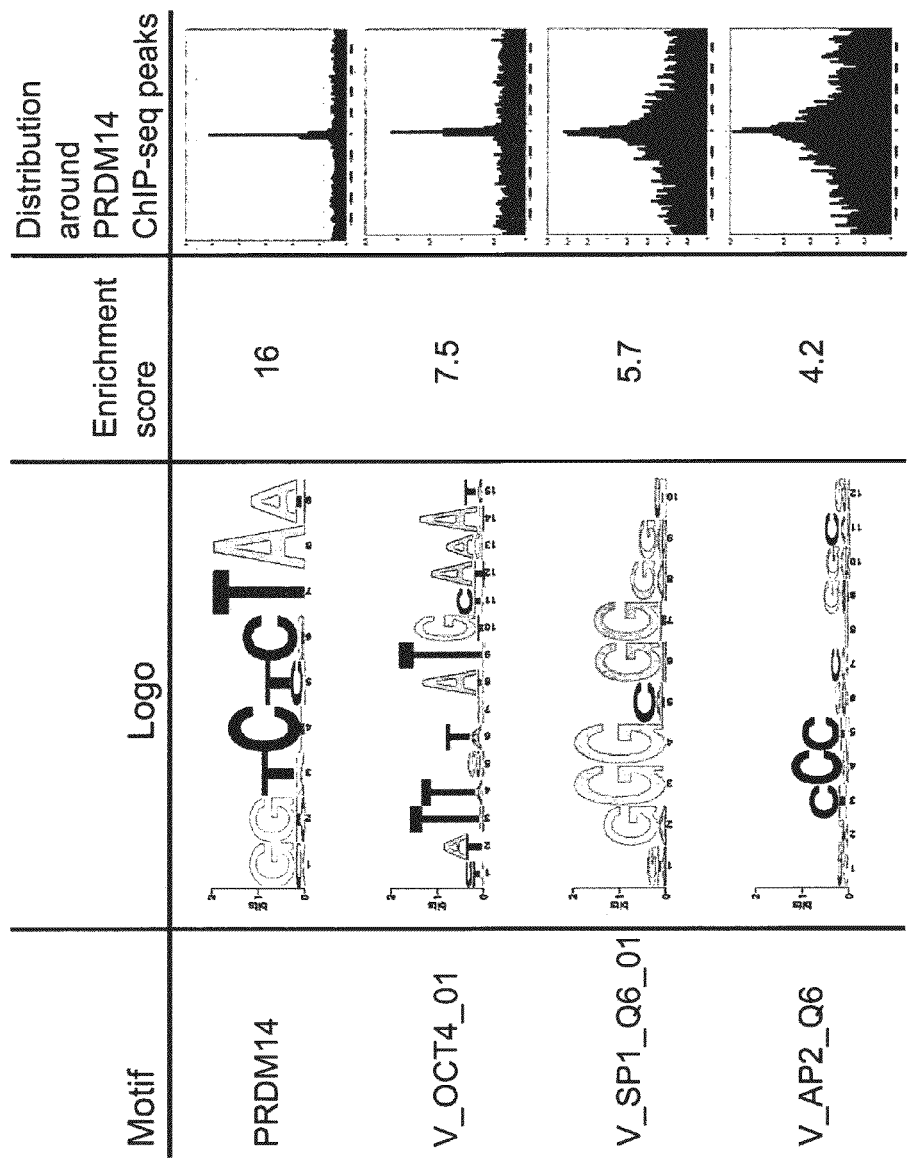

FIG. 15: Co-motif analysis. The distribution and enrichment of sequence motifs around PRDM14 ChIP-seq peaks. Except for the PRDM14 motif which was found de novo in this study, the other 3 motifs V_OCT4_01, V_SP1_Q6_01 and V_AP2_Q6 shown are the most enriched from the TRANSFAC database. The enrichment score reflects the number of motif matches compared to the expected number of matches in windows around the ChIP-seq peaks.

FIG. 16: PRDM14 regulates CR2 enhancer in different hESCs. (16A) Map of luciferase reporters used to test enhancer activity of CR2 and CR4. CR2 and CR4 of the POU5F1 upstream regulatory region were each cloned downstream of the luciferase reporter gene driven by a POU5F1 proximal promoter (~350 bp). (16B) Each of the constructs was transfected into HES2 and HES3 hESCs to test for enhancer activity. PRDM14 shRNA construct was co-transfected with the reporter construct and activity was normalized against the knockdown control. All values are means±s.e.m from 3 independent experiments (n=3). (16C) Mutation of PRDM14 site at CR2 reduces its activity in H1, HES2 and HES3 hESC. All values are means±s.e.m from 3 independent experiments (n=3).

FIG. 17: Mapping of functional domains for transcriptional regulation and reprogramming. (17A) A schematic summary of different molecules generated for PRDM14 functional study. N, N-terminal; SET, PR/SET domain; DBD, DNA binding domain; Δ, deletion. (17B) 3 copies of PRDM14 motif found in CR2 enhancer were inserted in tandem before a minimal promoter found in pGL4.23 luciferase reporter vector. Full length cDNA of PRDM14 or different mutant versions of PRDM14 were transfected into 293T cells to test for their ability to regulate transcription. Luciferase vector without PRDM14 motif was used as control. The reporter activity was normalized to the activity of control vector in the presence of PRDM14 or deletion mutants. All values are means±s.e.m from 3 independent experiments (n=3). (17C) Functional analysis of PRDM14 domains in reprogramming of human fibroblasts. Graph depicts fold change of number of TRA-1-60 positive hiPSC colonies generated from PRDM14 or its mutant molecules in conjunction with OCT4, SOX2, KLF4 and c-MYC (OSKM) with respect to the control (OSKM). Each column represents the average of 3 replicates. All values are means±s.e.m from 3 independent experiments (n=3). (17D) Deletion of the DNA binding domain at the C-terminal abolished PRDM14 binding activity as indicated in the EMSA. (17E) The first 5 zinc fingers but not the last zinc finger are critical for the binding of PRDM14. (17F) The first 5 zinc fingers but not the last zinc finger are required for the transcriptional activity of PRDM14.

FIG. 18: Regulation of target genes by PRDM14. (18A) Venn diagram showing the intersection of PRDM14-bound genes with genes that were down-regulated after PRDM14 depletion. This subset of PRDM14 bound genes are positively regulated by PRDM14. (18B) Venn diagram showing the intersection of PRDM14-bound genes with genes that were induced after PRDM14 depletion. (18C) GO analysis of the overlapping genes shown in (18A). (18D) GO analysis of the overlapping genes shown in (18B). (18E) Schematic representation of a model for the transcriptional regulatory network governed by PRDM14 in hESC.

FIG. 19: Validation of gene expression (from the different Gene Ontology group) upon PRDM14 depletion. (19A) 20 genes from the different Gene Ontology group of FIG. 18C were selected for qPCR validation and 19 genes were downregulated upon PRDM14 depletion. All values are means±s.e.m from 3 independent experiments (n=3). (19B) 20 genes from the different Gene Ontology group of FIG. 18D were selected for qPCR validation and all the 20 genes were upregulated upon PRDM14 depletion. All values are means±s.e.m from 3 independent experiments (n=3).

FIG. 20: Transcription factors that co-localize to PRDM14 sites at PRDM14 regulated genes. (20A) Top 20 enriched PWMs at PRDM14 sites. (20B) Motif logo for V_OCT4_01 TRANSFAC PWM. (20C) Examples of 10 PWM not enriched at PRDM14 sites. (20D) PRDM14 shows co-binding with OCT4, SOX2, NANOG and co-activator p300. Greyscale intensity in the heat map reflects the co-localization frequency of each of the transcription factors (the descending frequency of localization ranges from white to grey to dark grey).

FIG. 21: PRDM14 recruits polycomb group proteins in hESCs and during reprogramming. (21A) Co-localization analysis for PRDM14 and histone modifications. Greyscale intensity in the heat map reflects the co-localization frequency of each of transcription factors (the descending frequency of localization ranges from white to grey to dark grey). (21B) PRDM14 interacts with Ezh2 in hESC. Co-IP assays were performed using hESC whole cell lysate with anti-PRDM14 and anti-Ezh2 antibody. Western was carried out with anti-PRDM14 or anti-Ezh2 antibody. Anti-GST antibody was used in the control IP sample. (21C) PRDM14 interacts with Ezh2 in 293T cells. 293T cell were co-transfected with cDNA encoding HA tagged PRDM14 and Myc tagged EZH2 protein. Whole cell lysate was used for co-IP with anti-HA and anti-Myc antibody. Anti-GST antibody was used in the control IP. (21D) H3K27me3 is reduced with PRDM14 depletion. hESC transfected with control knockdown shRNA targeting Luciferase or PRDM14 shRNA were fixed and harvested 48 hr post transfection. ChIP was carried out with anti-H3K27me3 antibodies. All values are means±s.e.m from 3 independent experiments (n=3). (21E) Recruitment of Ezh2 is reduced with PRDM14 depletion. hESC transfected with control knockdown shRNA or PRDM14 shRNA were fixed and harvested 48 hr post transfection. ChIP was carried out with anti-Ezh2 antibodies. All values are means±s.e.m from 3 independent experiments (n=3). (21F) PRDM14 is targeted to the genes shown in (21D) in fibroblasts. MCR-5 fibroblasts infected with retroviruses expressing PRDM14 or control Red Fluorescent Protein (RFP) were fixed and harvested 5 days post infection. ChIP was carried out with anti-PRDM14 antibodies. All values are means±s.e.m from 3 independent experiments (n=3). (21G) H3K27me3 is induced at PRDM14 targets in fibroblasts. MCR-5 fibroblasts infected with retroviruses expressing PRDM14 or control RFP were fixed and harvested 5 days post infection. ChIP was carried out with anti-H3K27me3 antibodies. All values are means±s.e.m from 3 independent experiments (n=3). (21H) Ezh2 is recruited to PRDM14 targets in fibroblasts. MCR-5 fibroblasts infected with retroviruses expressing PRDM14 or control RFP were fixed and harvested 5 days post infection. ChIP was carried out with anti-Ezh2 antibodies. All values are means±s.e.m from 3 independent experiments (n=3). (21I) PRDM14 represses the genes shown in (21D) in fibroblasts. Total RNA of MCR-5 fibroblasts infected with retroviruses expressing PRDM14 or RFP were extracted. Expression levels of target genes were measured with real time-PCR and relative expression levels were normalized against the RFP infected control. All values are means±s.e.m from 3 independent experiments (n=3). (21J) Overexpression of NR2F1 and ZEB1 induce differentiation of hESCs. Expression construct for NR2F1 or ZEB1 was transfected into H1 hESCs and cellular morphology was captured by light microscopy. TRA-1-60 staining was performed on the control, NR2F1 and ZEB1 transfected cells.

DETAILED DESCRIPTION

Extensive efforts have been made in the identification of regulators for mESCs through the use of loss-of-function genetic approaches [23-26]. However, despite these efforts, little is known about the key regulators that are required for inducing pluripotency in human somatic cells and the maintenance of human embryonic stem cell (hESC) identity.

Here, the inventors performed a genome-wide RNAi screen and identified key regulators for the maintenance of hESCs, and which are able to induce pluripotency. PR domain-containing protein 14 (PRDM14) and nuclear factor related kappaB binding protein (NFRKB) were found to be effective in the reprogramming of human somatic cells.

The present invention thus relates to methods of inducing pluripotency in a human somatic cell, to methods of maintaining hESCs and to human somatic cells comprising OCT4, SOX2, at least one of KLF4 and c-MYC and at least one of PRDM14 and NFRKB.

It was previously known that human somatic cells could be reprogrammed into induced pluripotent stem cells (iPSCs) through the co-expression of four transcription factors, OCT4, SOX2, KLF4 and c-MYC [27, 42-44]. This is significant since the reprogramming of somatic cells provides unprecedented opportunities for generating patient-specific pluripotent cells which may be used as in vitro models for studying and developing applications for treating human diseases [28-31].

OCT4 is a protein encoded by the human POU5F1 gene [71]. The POU family of transcription factors consists of at least 14 members, which often act synergistically during vertebrate development with the SOX family of transcription factors [72-74]. The role of OCT4 as an inducer of pluripotency is well established [27, 57]. The sequence of two isoforms of the human OCT4 gene, generated by alternative splicing, is available for example in GenBank under DQ486515 and DQ486516. As will be understood, the reference to OCT4 in the present application may encompass either of the OCT4 isoforms. A representative amino acid sequence for human OCT4 is provided below:

```
                                        (SEQ ID NO: 1)
MAGHLASDFAFSPPPGGGGDGPGGPEPGWVDPRTWLSFQGP

PGGPGIGPGVGPGSEVWGIPPCPPPYEFCGGMAYCGPQVGV

GLVPQGGLETSQPEGEAGVGVESNSDGASPEPCTVTPGAVK

LEKEKLEQNPEESQDIKALQKELEQFAKLLKQKRITLGYTQ

ADVGLTLGVLFGKVFSQTTICRFEALQLSFKNMCKLRPLLQ
```

```
KWVEEADNNENLQEICKAETLVQARKRKRTSIENRVRGNLE

NLFLQCPKPTLQQISHIAQQLGLEKDVVRVWFCNRRQKGKR

SSSDYAQREDFEAAGSPFSGGPVSFPLAPGPHFGTPGYGSP

HFTALYSSVPFPEGEAFPPVSVTTLGSPMHSN
```

SOX2 is a transcription factor that is critical to maintain self-renewal of undifferentiated stem cells, and is one of the key transcription factors required in iPSCs [45]. The SOX family of transcription factors consists of at least 20 members [72-74]. Despite their diverse biological roles, the specificity of SOX proteins for DNA elements is largely indistinguishable and highly conserved [75]. Indeed, specificity in transcriptional control may be achieved as a result of selective heterodimerization. For example, SOX2/OCT4 pairs are important factors in embryonic stem (ES) cells [8, 64]. The sequence of the human SOX2 gene is available, for example, in GenBank under BC013923. As will be understood, reference herein to SOX2 may include for example mutated versions of SOX proteins, such as described International Patent Application PCT/SG2010/000423. A representative amino acid sequence for human SOX2 is provided below:

```
                                        (SEQ ID NO: 2)
MYNMMETELKPPGPQQTSGGGGGNSTAAAAGGNQKNSPDRV

KRPMNAFMVWSRGQRRKMAQENPKMHNSEISKRLGAEWKLL

SETEKRPFIDEAKRLRALHMKEHPDYKYRPRRKTKTLMKKD

KYTLPGGLLAPGGNSMASGVGVGAGLGAGVNQRMDSYAHMN

GWSNGSYSMMQDQLGYPQHPGLNAHGAAQMQPMHRYDVSAL

QYNSMTSSQTYMNGSPTYSMSYSQQGTPGMALGSMGSVVKS

EASSSPPVVTSSSHSRAPCQAGDLRDMISMYLPGAEVPEPA

APSRLHMSQHYQSGPVPGTAINGTLPLSHM
```

KLF4 is a member of a family of proteins characterized by their three Cyst His2 zinc fingers located at the C-terminus, each of which is separated by a highly conserved H/C link. KLF4 interacts with p300 histone acetyltransferase to regulate gene transcription by modulating histone acetylation [76]. KLF4 has been shown to play a role in reprogramming human somatic cells into iPSCs [27]. The sequence of the human KLF4 gene is available, for example, in GenBank under AF105036. A representative amino acid sequence for human KLF4 is provided below:

```
                                        (SEQ ID NO: 3)
MRQPPGESDMAVSDALLPSFSTFASGPAGREKTLRQAGAPN

NRWREELSHMKRLPPVLPGRPYDLAAATVATDLESGGAGAA

CGGSNLAPLPRRETEEFNDLLDLDFILSNSLTHPPESVAAT

VSSSASASSSSSPSSSGPASAPSTCSFTYPIRAGNDPGVAP

GGTGGGLLYGRESAPPPTAPFNLADINDVSPSGGFVAELLR

PELDPVYIPPQQPQPPGGGLMGKFVLKASLSAPGSEYGSPS

VISVSKGSPDGSHPVVVAPYNGGPPRTCPKIKQEAVSSCTH

LGAGPPLSNGHRPAAHDFPLGRQLPSRTTPTLGLEEVLSSR

DCHPALPLPPGFHPHPGPNYPSFLPDQMQPQVPPLHYQGQS
```

```
RGFVARAGEPCVCWPHFGTHGMMLTPPSSPLELMPPGSCMP

EEPKPKRGRRSWPRKRTATHTCDYAGCGKTYTKSSHLKAHL

RTHTGEKPYHCDWDGCGWKFARSDELTRHYRKHTGHRPFQC

QKCDRAFSRSDHLALHMKRHF
``` c-MYC is a member of a family of transcription factors containing a basic Helix-Loop-Helix Leucine. It has been proposed that the role of c-MYC in establishing iPSCs may be as a booster of reprogramming rather than a controller of maintenance [27]. The sequence of the human c-MYC gene may be found, for example, in GenBank under NCBI RefSeq NM_002467. A representative amino acid sequence for human c-MYC is provided below:

```
                                              (SEQ ID NO: 4)
MPLNVSFTNRNYDLDYDSVQPYFYCDEEENFYQQQQQSELQ

PPAPSEDIWKKFELLPTPPLSPSRRSGLCSPSYVAVTPFSL

RGDNDGGGGSFSTADQLEMVTELLGGDMVNQSFICDPDDET

FIKNIIIQDCMWSGFSAAAKLVSEKLASYQAARKDSGSPNP

ARGHSVCSTSSLYLQDLSAAASECIDPSVVFPYPLNDSSSP

KSCASQDSSAFSPSSDSLLSSTESSPQGSPEPLVLHEETPP

TTSSDSEEEQEDEEEIDVVSVEKRQAPGKRSESGSPSAGGH

SKPPHSPLVLKRCHVSTHQHNYAAPPSTRKDYPAAKRVKLD

SVRVLRQISNNRKCTSPRSSDTEENVKRRTHNVLERQRRNE

LKRSFFALRDQIPELENNEKAPKVVILKKATAYILSVQAEE

QKLISEEDLLRKRREQLKHKLEQLRNSCA
```

It will be appreciated that reference herein to OCT4, SOX2, KLF4 and c-MYC includes those embodiments described above, as well as sequence variants or fragments (e.g. fragments of at least 25, 50, 100, 150, 200, 250, 300, 350, 400 or more amino acids in length) which retain the ability to direct the specific function of OCT4, SOX2, KLF4 and c-MYC, respectively, including for example either the induction or maintenance of pluripotency. Any such variants or fragments may be used in the methods of the present invention, for example, either in methods involving contacting the human somatic cells with OCT4, SOX2, KLF4 or c-MYC or methods involving expressing OCT4, SOX2, KLF4 or c-MYC in the human somatic cell. In a particular embodiment, the OCT4, SOX2, KLF4 and c-MYC used in the present invention may be obtained from cDNA found in Addgene plasmids 17217, 17218, 17219 and 17220, respectively [27].

Polypeptides or peptides that have substantial identity to proteins encoded by the cDNA found in the Addgene plasmids or substantial identity to the representative amino acid sequences provided herein for OCT4, SOX2, KLF4 and c-MYC may also be used. Similarly, nucleotide sequences encoding any of these polypeptides, peptides or proteins, or nucleotide sequences having substantial identity thereto, are also encompassed by the present invention.

Two sequences are considered to have substantial identity if, when optimally aligned (with gaps permitted), they share at least approximately 50% sequence identity, or if the sequences share defined functional motifs. In alternative embodiments, optimally aligned sequences may be considered to be substantially identical (i.e., to have substantial identity) if they share at least 60%, 70%, 75%, 80%, 85%, 90%, 95%, 96%, 97%, 98%, or 99% identity over a specified region. The term "identity" refers to sequence similarity between two polypeptides molecules. Identity can be determined by comparing each position in the aligned sequences. A degree of identity between amino acid sequences is a function of the number of identical or matching amino acids at positions shared by the sequences, for example, over a specified region. Optimal alignment of sequences for comparisons of identity may be conducted using a variety of algorithms, as are known in the art, including the ClustalW program, available at http://clustalw.genome.ad.ip, the local homology algorithm of Smith and Waterman, 1981, *Adv. Appl. Math* 2: 482, the homology alignment algorithm of Needleman and Wunsch, 1970, *J. Mol. Biol.* 48:443, the search for similarity method of Pearson and Lipman, 1988, *Proc. Natl. Acad. Sci. USA* 85:2444, and the computerised implementations of these algorithms (such as GAP, BESTFIT, FASTA and TFASTA in the Wisconsin Genetics Software Package, Genetics Computer Group, Madison, Wis., U.S.A.). Sequence identity may also be determined using the BLAST algorithm, described in Altschul et al., 1990, *J. Mol. Biol.* 215:403-10 (using the published default settings). For example, the "BLAST 2 Sequences" tool, available through the National Center for Biotechnology Information (through the interne at http://www.ncbi.nlm.nih.gov/BLAST/bl2seq/wblast2.cqi) may be used, selecting the "blastp" program at the following default settings: expect threshold 10; word size 3; matrix BLOSUM 62; gap costs existence 11, extension 1. In another embodiment, the person skilled in the art can readily and properly align any given sequence and deduce sequence identity and/or homology by mere visual inspection Here, an important role for each of PRDM14 and NFRKB in inducing and maintaining pluripotency in human somatic cells has now been observed and characterized.

As shown herein, the presence of either PRDM14 or NFRKB during culture of human somatic cells enhances reprogramming of the human somatic cells to iPSCs (i.e. imparting pluripotency). This is observed when the cells are cultured in the presence of OCT4, SOX2, at least one of KLF4 and c-MYC, and at least one of PRDM14 and NFRKB. While OCT2 and SOX2 may be required for the generation of iPSCs, PRDM14 and NFRKB are able to substitute for either KLF4 or c-MYC. Thus, the present methods provide a method of using OCT4, SOX2 and KLF4 or c-MYC, together with at least one of PRDM14 and NFRKB to induce pluripotency by converting a non-pluripotent cell to a pluripotent cell, including in vitro methods.

In a particular embodiment, there is provided a method of inducing pluripotency in a human somatic cell comprising culturing the human somatic cell in the presence of (i) OCT4 and SOX2; (ii) at least one of KLF4 and c-MYC; and (iii) at least one of PRDM14 and NFRKB.

As will be understood, prior to providing OCT4, SOX2, at least one of KLF4 and c-MYC, and at least one of PRDM14 and NFRKB, the human somatic cells may be cultured in conditions appropriate for maintaining the particular human somatic cell type. Appropriate conditions for culturing human somatic cell types are known in the art. For example, in a representative embodiment, human fibroblast cells may be cultured in 15% fetal bovine serum (FBS)/Dulbecco's Modified Eagle Medium (DMEM).

Methods of inducing pluripotency are known, for example as described in Takahashi and Yamanaka [41]. In the present methods for inducing pluripotency, the human somatic cells are cultured in the presence of OCT4, SOX2, at least one of KLF4 and c-MYC, and at least one of PRDM14 and NFRKB. The culture conditions may be adjusted during the method from conditions supporting the human somatic cells to conditions which are suitable for the growth and maintenance of embryonic stem cells. The change in culture conditions may be performed, for example, upon the introduction of OCT4, SOX2, at least one of KLF4 and c-MYC, and at least one of PRDM14 and NFRKB, or shortly thereafter (e.g. about 24 hours). The cells may then be maintained and expanded in such conditions which are suitable for the growth and maintenance of embryonic stem cells.

Thus, the present invention provides methods of reprogramming human somatic cells to iPSCs, which are known to be comparable to hESCs [27]. These human iPSCs are able to be maintained in the presence of OCT4, SOX2, at least one of KLF4 and c-MYC, and at least one of PRDM14 and NFRKB. Indeed, a role for these regulators in maintaining pluripotency in hESCs is further shown by the fact that reduction in expression of one of these key regulators, PRDM14, results in a loss of pluripotency.

Here, it is shown that PRDM14 is required to maintain the expression of a key pluripotency gene, POU5F1 (coding for the protein OCT4). De novo computational methods identified an over-represented PRDM14 motif, which the inventors validated using electrophoretic mobility shift assay (EMSA). Interestingly, PRDM14 shows co-binding with OCT4, SOX2, NANOG and the co-activator p300, indicating that the PRDM14 circuitry is integrated into the core hESC transcriptional regulatory network, and is an important regulatory factor in maintaining pluripotency.

Also contemplated therefore is a method of maintaining pluripotency of a human embryonic stem cell (hESC) comprising culturing the hESC in the presence of (i) OCT4 and SOX2; (ii) at least one of KLF4 and c-MYC; and (iii) at least one of PRDM14 and NFRKB. Similar to the methods of inducing pluripotency, in the methods for maintaining pluripotency, the hESCs may be cultured under conditions suitable for the growth and maintenance of embryonic stem cells.

In the methods of the present invention, culturing the cell (human somatic cell or hESC) in the presence of OCT4 and SOX2, at least one of KLF4 and c-MYC, and at least one of PRDM14 and NFRKB includes contacting the cell with the various pluripotency protein factors so that the pluripotency protein factors are taken up by the cell, as well as transfecting or transducing the cell with nucleic acids encoding the various pluripotency protein factors and expressing the pluripotency protein factors. Procedures for accomplishing such culturing methods are widely known in the art and any of these known culturing techniques may be used in the present invention. As used herein, reference to pluripotency protein factors is a reference to OCT4, SOX2, KLF4, c-MYC, PRDM14 and NFRKB, either alone or in combination.

Where the methods involve transfecting or transducing the cell with nucleic acids encoding the various pluripotency protein factors, expression of the pluripotency protein factors may involve expression from an expression vector. The expression vector may be of any suitable structure which provides expression of the pluripotency protein factors. As will be appreciated, a suitable promoter will be operably linked to the coding region for the particular pluripotency protein factor. For example, a coding sequence is operably linked to a promoter if the promoter activates the transcription of the coding sequence. The expression vector may for example be a plasmid, bacteriophage, DNA virus, RNA virus, or retrovirus vector. For example, a pMX retroviral plasmid may be used to carry cDNA of human OCT4, SOX2, KLF4, c-MYC, PRDM14 or NFRKB. It will be understood that the pluripotency protein factors may be co-expressed from one or more expression vectors.

Once the cell has been contacted with the pluripotency protein factors, or once the cell has been transfected or transduced with nucleic acid molecules encoding each of the pluripotency protein factors, the cells may be cultured under conditions suitable for the growth and maintenance of embryonic stem cells. Conditions that are suitable for growth and maintenance embryonic stem cells are known. Exemplary conditions are described herein which were used for the culture of the hESC lines H1, H9, HES2, HES3 and H1 POU5F1-GFP lines. Further, commercial medium for human embryonic stem cell culture is available (e.g. HEScGRO from Millipore; StemPro from Invitrogen) and other culture media and culture conditions are described, for example, in Lu et al. (2006) *PNAS*, 103(15): 5688-5693. In some circumstances, it may be desirable to use feeder cells to promote stem cell growth in culture, in keeping with standard embryonic stem cell culture techniques.

As used herein, the term "cell" refers to and includes a single cell, as well as a plurality of cells or a population of cells, where context permits, and unless otherwise specified. Similarly, reference to "cells" also includes reference to a single cell where context permits, unless otherwise specified. The cell or cells may be grown in e.g. batch culture or in tissue culture plates.

The human somatic cell may be any human somatic cell, for example any human somatic cell that is partially differentiated or fully differentiated, including an in vitro cell, a cell in culture, or an explanted cell from a subject. The cell may be of any type of partially or fully differentiated human somatic cell, including for example a human fibroblast cell. Likewise, the hESC may be any type of undifferentiated hESC. The undifferentiated hES cell or cells are typically originally obtained from a blastocyst as is known in the art, but may be previously expanded.

As used herein, the term "pluripotent" or "pluripotency" refers to a state where the cell has the potential to differentiate into any of the three germ layers: endoderm, mesoderm or ectoderm. Pluripotency may be assessed according to any means known in the art. For example, the expression levels of known pluripotency markers, such as for example NANOG, TRA-1-60, TRA-1-81, SSEA-4 or alkaline phosphatase, may be determined. An increased expression of any of these genes as compared to levels in differentiated human somatic cells may be considered indicative of pluripotency. Also, cells may be identified as pluripotent by their ability to differentiate into different lineages via EB (embryoid body)-mediated or growth factor-induced in vitro differentiation or by teratoma formation assays.

The maintenance of hESCs refers to the maintenance of these cells in their undifferentiated, pluripotent state. Techniques described above for determining pluripotency may also be used to determine if cells are maintained as embryonic stem cells. Other known means may also be used. For example, the expression profile of hESC-associated genes, such as for example SOX2, HELLS and DPPA4, may be determined. Continued expression of these genes during culture may indicate maintenance of hESCs. In contrast, an increased expression of proteins that are expressed in differentiated cells types, such as RUNX1, MAFB and IGFBP5, may signify differentiation, and therefore a loss of hESCs.

Here, a key role has been identified for PRDM14 in inducing pluripotency in human somatic stem cells, and maintaining hESCs. PRDM14 is a pluripotency protein factor belongs to a family of PR (PRDI-BFI and RIZ) domain proteins, a common domain found in histone modifying enzymes [50, 51]. In this family, there are predicted to be at least 17 PRDM proteins in primates and 16 PRDM proteins in rodents [70]. The proteins share a characteristic domain organization, each (with the exception of PRDM11) having an N-terminal PR domain followed by a variable number of zinc-finger repeats [70]. The sequence of the human PRDM14 gene may be found, for example, in GenBank under AF319458. A representative sequence for human PRDM14 is provided below:

(SEQ ID NO: 5)
MALPRPSEAVPQDKVCYPPESSPQNLAAYYTPFPSYGHYRN

SLATVEEDFQPFRQLEAAASAAPAMPPFPFRMAPPLLSPGL

GLQREPLYDLPWYSKLPPWYPIPHVPREVPPFLSSSHEYAG

ASSEDLGHQIIGGDNESGPCCGPDTLIPPPPADASLLPEGL

RTSQLLPCSPSKQSEDGPKPSNQEGKSPARFQFTEEDLHFV

LYGVTPSLEHPASLHHAISGLLVPPDSSGSDSLPQTLDKDS

LQLPEGLCLMQTVFGEVPHFGVFCSSFIAKGVRFGPFQGKV

VNASEVKTYGDNSVMWEIFEDGHLSHFIDGKGGTGNWMSYV

NCARFPKEQNLVAVQCQGHIFYESCKEIHQNQELLVWYGDC

YEKFLDIPVSLQVTEPGKQPSGPSEESAEGYRCERCGKVFT

YKYYRDKHLKYTPCVDKGDRKFPCSLCKRSFEKRDRLRIHI

LHVHEKHRPHKCSTCGKCFSQSSSLNKHMRVHSGDRPYQCV

YCTKRFTASSILRTHIRQHSGEKPFKCKYCGKSFASHAAHD

SHVRRSHKEDDGCSCSICGKIFSDQETFYSHMKFHEDY

Few of the PRDM family members have been studied in detail, and it will be appreciated that the present findings for PRDM14 may also extend to other members of the family. Further, it will be understood that reference herein to PRDM14 may encompass sequence variants or fragments (e.g. fragments of at least 25, 50, 100, 150, 200, 250, 300, 350, 400 or more amino acids in length) which retain the ability to direct the specific function of PRDM14, including for example either the induction or maintenance of pluripotency. Any such variants or fragments may be used in the methods of the present invention, for example, either in methods involving contacting the human somatic cells with PRDM14 or methods involving expressing PRDM14 in the human somatic cell.

Polypeptides or peptides that have substantial identity to PRDM14 protein sequences known in the art or substantial identity to the representative amino acid sequences provided herein for PRDM14 may also be used. Similarly, nucleotide sequences encoding any of these polypeptides, peptides or proteins, or nucleotide sequences having substantial identity thereto, are also encompassed by the present invention. The meaning of substantial identity has been described earlier herein and applies equally to nucleotide and amino acid sequences of PRDM14.

Previous work on a Prdm14 knockout mouse model showed that Prdm14 is critical for the establishment of the germ cell lineage [52]. In addition, Prdm14 is essential for the derivation of embryonic germ cells from primordial germ cells (PGCs). However, the knockout animals do not show early embryonic lethal phenotype, unlike the knockout phenotype of other key regulators essential for the maintenance of pluripotency of mESCs [13, 15, 57, 58]. Prdm14 does not appear to be required to maintain mESC and pluripotent stem cells of the blastocysts [23, 25, 52]. In PGCs, the expression of Pou5f1 is maintained in the absence of Prdm14. However, the present invention indicates that PRDM14 is critical for activating POU5F1 in hESCs.

Without being limited to any particular theory, the present inventors suggest that PRDM14 maintains pluripotency and promotes the acquisition of pluripotency of the germ cell lineage and hESCs through distinctive mechanisms. These differences may arise through cell-type specific or species-specific differences in regulating Pou5f1. Also, it is shown that PRDM14 associates with NANOG, another transcription factor important for the establishment of ground state pluripotency [58]. PRDM14 and NANOG can function synergistically to activate POU5F1 enhancer as well as to mediate reprogramming. Therefore, PRDM14 is connected via multiple points to the pluripotency-specific transcriptional regulatory network.

Here, a key role has also been identified for NFRKB in inducing pluripotency in human somatic stem cells, and maintaining hESCs. NFRKB, which is thought to be a component of the chromatin-remodelling INO80 complex, is a member of a family of transcription factors and has been shown to bind in vitro to several of the kappa B regulatory elements [77]. The sequence of the human NFRKB gene may be found, for example, in GenBank under BC063280. A representative amino acid sequence for human NFRKB is provided below:

(SEQ ID NO: 6)
MDSLDHMLTDPLELGPCGDGHGTRIMEDCLLGGTRVSLPED

LLEDPEIFFDVVSLSTWQEVLSDSQREHLQQFLPQFPEDSA

EQQNELILALFSGENFRFGNPLHIAQKLFRDGHFNPEVVKY

RQLCFKSQYKRYLNSQQQYFHRLLKQILASRSDLLEMARRS

GPALPFRQKRPSPSRTPEEREWRTQQRYLKVLREVKEECGD

TALSSDEEDLSSWLPSSPARSPSPAVPLRVVPTLSTTDMKT

ADKVELGDSDLKIMLKKHHEKRKHQPDHPDLLTGDLTLNDI

MTRVNAGRKGSLAALYDLAVLKKKVKEKEEKKKKIKTIKS

EAEDLAEPLSSTEGVAPLSQAPSPLAIPAIKEEPLEDLKPC

LGINEISSSFFSLLLEILLLESQASLPMLEERVLDWQSSPA

SSLNSWFSAAPNWAELVLPALQYLAGESRAVPSSFSPFVEF

KEKTQQWKLLGQSQDNEKELAALFQLWLETKDQAFCKQENE

DSSDATTPVPRVRTDYVVRPSTGEEKRVFQEQERYRYSQPH

KAFTFRMHGFESVVGPVKGVFDKETSLNKAREHSLLRSDRP

AYVTILSLVRDAAARLPNGEGTRAEICELLKDSQFLAPDVT

STQVNTVVSGALDRLHYEKDPCVKYDIGRKLWIYLHRDRSE

EEFERIHQAQAAAAKARKALQQKPKPPSKVKSSSKESSIKV

LSSGPSEQSQMSLSDSSMPPTPVTPVTPTTPALPAIPISPP

PVSAVNKSGPSTVSEPAKSSSGVLLVSSPTMPHLGTMLSPA

SSQTAPSSQAAARVVSHSGSAGLSQVRVVAQPSLPAVPQQS

GGPAQTLPQMPAGPQIRVPATATQTKVVPQTVMATVPVKAQ

TTAATVQRPGPGQTGLTVTSLPATASPVSKPATSSPGTSAP

SASTAAVIQNVTGQNIIKQVAITGQLGVKPQTGNSIPLTAT

-continued

NFRIQGKDVLRLPPSSITTDAKGQTVLRITPDMMATLAKSQ

VTTVKLTQDLFGTGGNTTGKGISATLHVTSNPVHAADSPAK

ASSASAPSSTPTGTTVVKVTPDLKPTEASSSAFRLMPALGV

SVADQKGKSTVASSEAKPAATIRIVQGLGVMPPKAGQTITV

ATHAKQGASVASGSGTVHTSAVSLPSMNAAVSKTVAVASGA

ASTPISISTGAPTVRQVPVSTTVVSTSQAGKLPTRITVPLS

VISQPMKGKSVVTAPIIKGNLGANLSGLGRNIILTTMPAGT

KLIAGNKPVSFLTAQQLQQLQQQGQATQVRIQTVPASHLQQ

GTASGSSKAVSTVVVTTAPSPKQAPEQQ

It will be understood that reference herein to NFRKB may encompass sequence variants or fragments (e.g. fragments of at least 25, 50, 100, 150, 200, 250, 300, 350, 400 or more amino acids in length) which retain the ability to direct the specific function of NFRKB, including for example either the induction or maintenance of pluripotency. Any such variants or fragments may be used in the methods of the present invention, for example, either in methods involving contacting the human somatic cells with NFRKB or methods involving expressing NFRKB in the human somatic cell.

Polypeptides or peptides that have substantial identity to NFRKB protein sequences known in the art or substantial identity to the representative amino acid sequences provided herein for NFRKB may also be used. Similarly, nucleotide sequences encoding any of these polypeptides, peptides or proteins, or nucleotide sequences having substantial identity thereto, are also encompassed by the present invention. The meaning of substantial identity has been described earlier herein and applies equally to nucleotide and amino acid sequences of NFRKB.

Thus, the present methods are based on the finding that PRDM14 and NFRKB enhance reprogramming of human somatic cells. The profound effect of these pluripotency protein factors is exemplified by the conversion of human somatic cells to iPSCs when cultured with OCT4 and SOX2 and at least one of KLF4 and c-MYC.

In an embodiment, the method of inducing pluripotency in a human somatic cell, or maintaining pluripotency in a hESC, may comprise expression in the human somatic cell or the hESC of PRDM14 or NFRKB together with OCT4, SOX2 and KLF4. The method may further comprise expressing c-MYC. In the human somatic cell, the presence of c-MYC may further enhance generation of iPSCs. Alternatively, KLF4 may be substituted with c-MYC.

If preferred, individual colonies of induced pluripotent cells may be selected and then expanded in order to obtain a clonal population of an induced pluripotent cell, in accordance with standard cell culture techniques.

The present invention also provides a human somatic cell comprising (i) OCT4 and SOX2; (ii) at least one of KLF4 and c-MYC; and (iii) at least one of PRDM14 and NFRKB. The cell may comprise one or more expression vectors which provide for the expression these pluripotency protein factors.

The present methods may be used to conveniently produce a human somatic cell that comprises OCT4, SOX2 and at least one of KLF4 and c-MYC together with at least one of PRDM14 and NFRKB. As described above, the cell may have taken up the pluripotency protein factors or may have been transfected or transduced the cell with nucleic acid for the pluripotency protein factors and thereby expresses the pluripotency protein factors. As well, the human somatic cell that comprises OCT4, SOX2, at least one of KLF4 and c-MYC together with at least one of PRDM14 and NFRKB may be one in which pluripotency has been induced.

As will be appreciated, the cell in which pluripotency is to be induced may already express one or more of the pluripotency protein factors, such as OCT4, SOX2, KLF4 and c-MYC and one or both of PRDM14 and NFRKB, but culture in the presence of OCT4, SOX2, at least one of KLF4 and c-MYC and at least one of PRDM14 and NFRKB according to the present invention will enhance reprogramming.

The induced pluripotent stem cells and hESCs of the present invention may be used in any therapeutic, clinical or research application to which embryonic stem cells generally are capable of being used. For example, patient-specific pluripotent cells of the present invention may have application as in vitro models for studying and developing applications for treating human diseases [28-31]. This includes their use in therapies relating to regenerative medicine and tissue replacement after injury or disease. It also includes uses in the treatment of diseases such as, for example, blood and immune-system related genetic diseases, cancers, and disorders; juvenile diabetes; Parkinson's; blindness and spinal cord injuries.

The invention is further illustrated by way of the following non-limiting examples.

EXAMPLES

Example 1

Detailed below are procedures in an exemplary method for the identification of PRDM14 and NFRKB as regulators of hESCs.

Figure 1A:
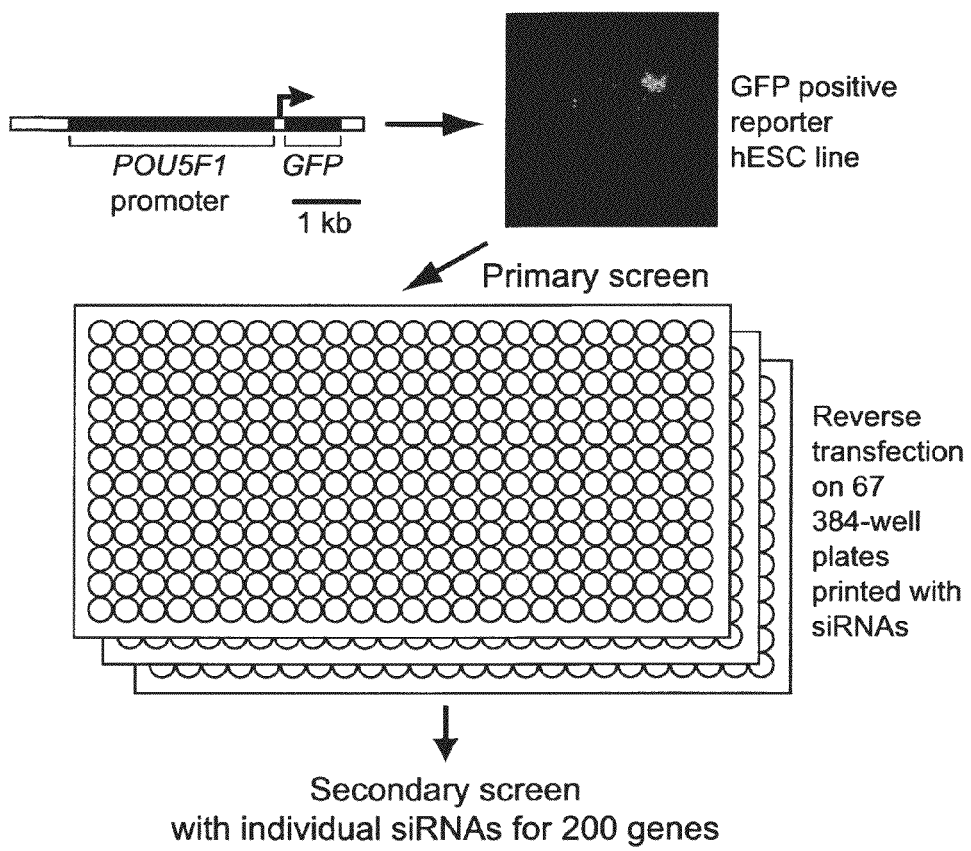
FIG. 1: Genome-wide screen for regulators that maintain hESC identity. (1A) Schematic representation of siRNA screen. H1 hESC line with a GFP reporter gene driven by the POU5F1 promoter was used for the screen. For the primary screen, 21,121 Dharmacon SMARTpooled siRNA were seeded onto 67 384-well plates and the POU5F1-GFP reporter hESCs were reverse transfected on these plates. For secondary screen, individual siRNAs for 200 high confidence candidates from the primary screen were reverse transfected into the reporter cells and two other hESC lines HES2 and HES3. (1B) Montage representing the images for GFP fluorescence and Hoechst staining for a typical 384-well plate is shown. The hESCs were imaged 4 days post transfection. The negative control siRNA (NT: non-targeting) and the positive controls siRNA (GFP and POU5F1) were printed at the designated wells as indicated. (1C) Dot plot of the genome-wide screen results. The average z-scores of the GFP readouts are shown. Controls are represented by the open square box (NT siRNA), open circle (POU5F1 siRNA) and filled square box (GFP siRNA). Genes with z-score>2, represented by a filled circle above the z-score=2 line, are considered as potential candidates required for the maintenance of hESC identity. The rest of the genes are indicated as filled circles below the z-score=2 line.
Figure 2A:
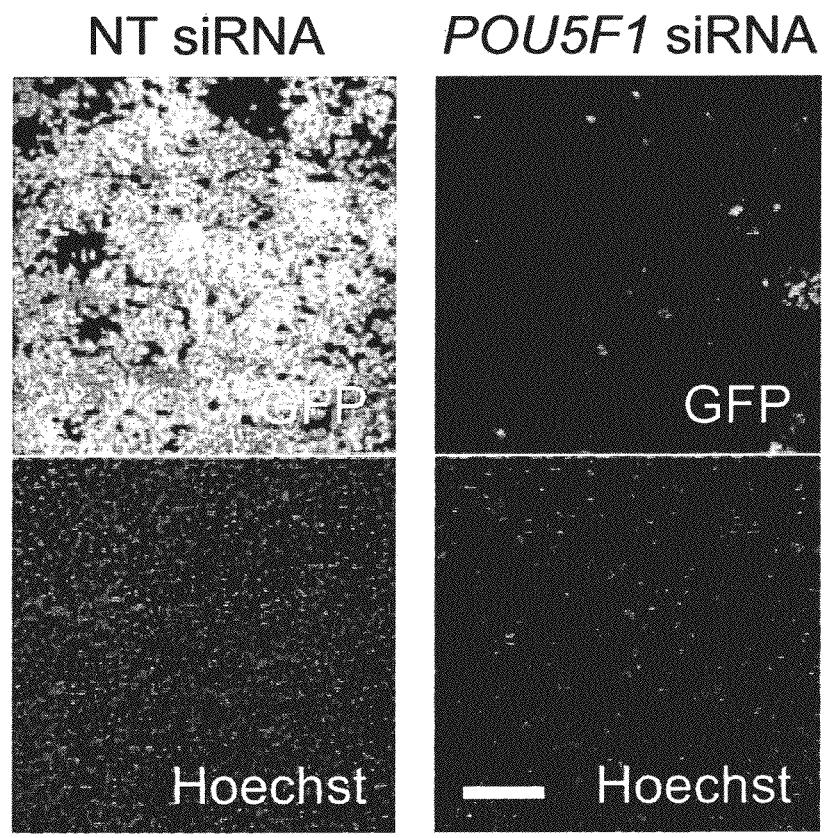
FIG. 2: Characterization of POU5F1-GFP H1 hESC line. (2A) POU5F1-GFP reporter cells transfected with non-targeting (NT) siRNA exhibited strong fluorescence while reporter cells transfected with POU5F1 siRNA resulted in a reduction in GFP expression. Nuclei of the cells were counterstained with Hoechst. Scale bars represent 50 μm. (2B) Fluorescent activated cell sorting for GFP quantification. Graphed lines are shown for non-reporter cells (H1 hESC), POU5F1-GFP reporter cells transfected with POU5F1 siRNA (POU5F1 siRNA) and reporter cells transfected with non-targeting siRNA (NT siRNA). (2C) Karyotypic analysis of POU5F1-GFP reporter cells. The cells have a normal karyotype with 46XY chromosomes. (2D) Teratoma formation assay for POU5F1-GFP reporter cells. Teratoma of ectoderm, mesoderm and endoderm lineages were obtained after 8 weeks of injection into SCID mice.
Figure 2B:
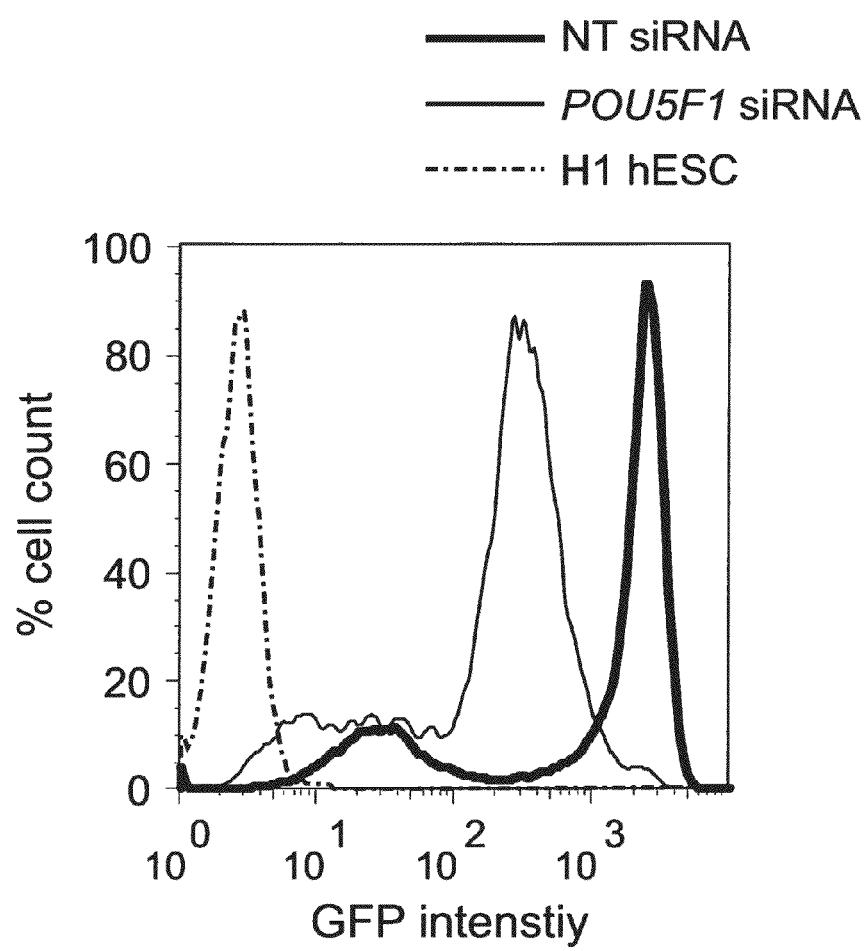
Figure 2C:
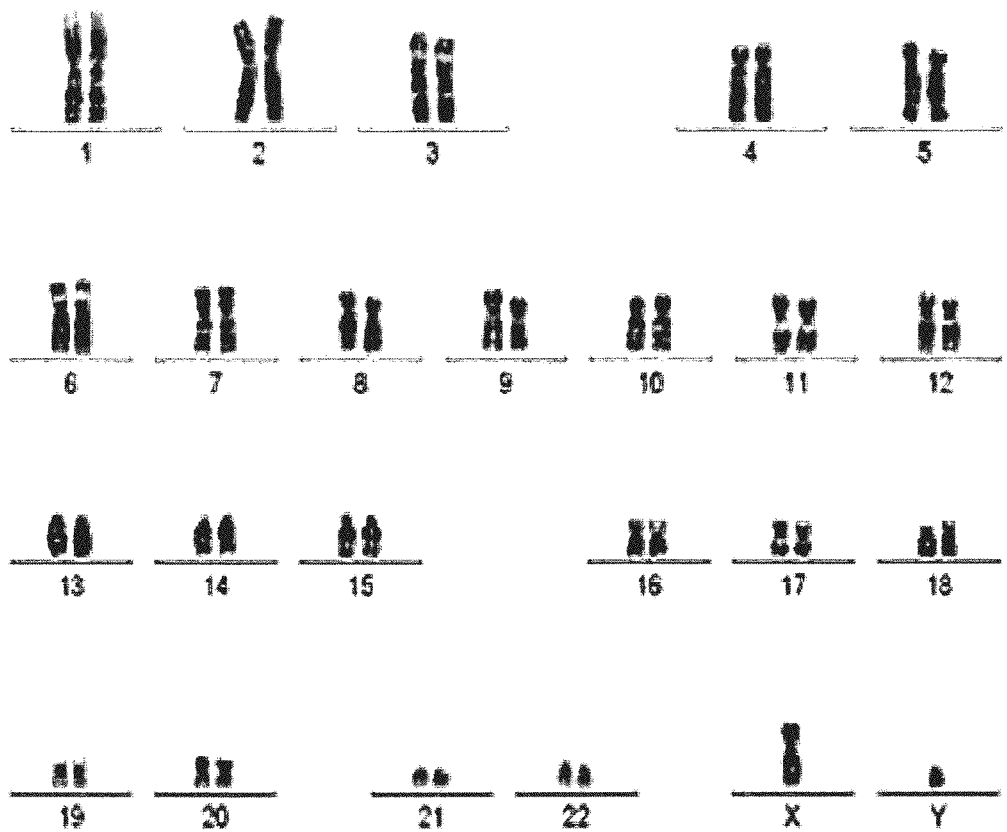
Figure 2D:
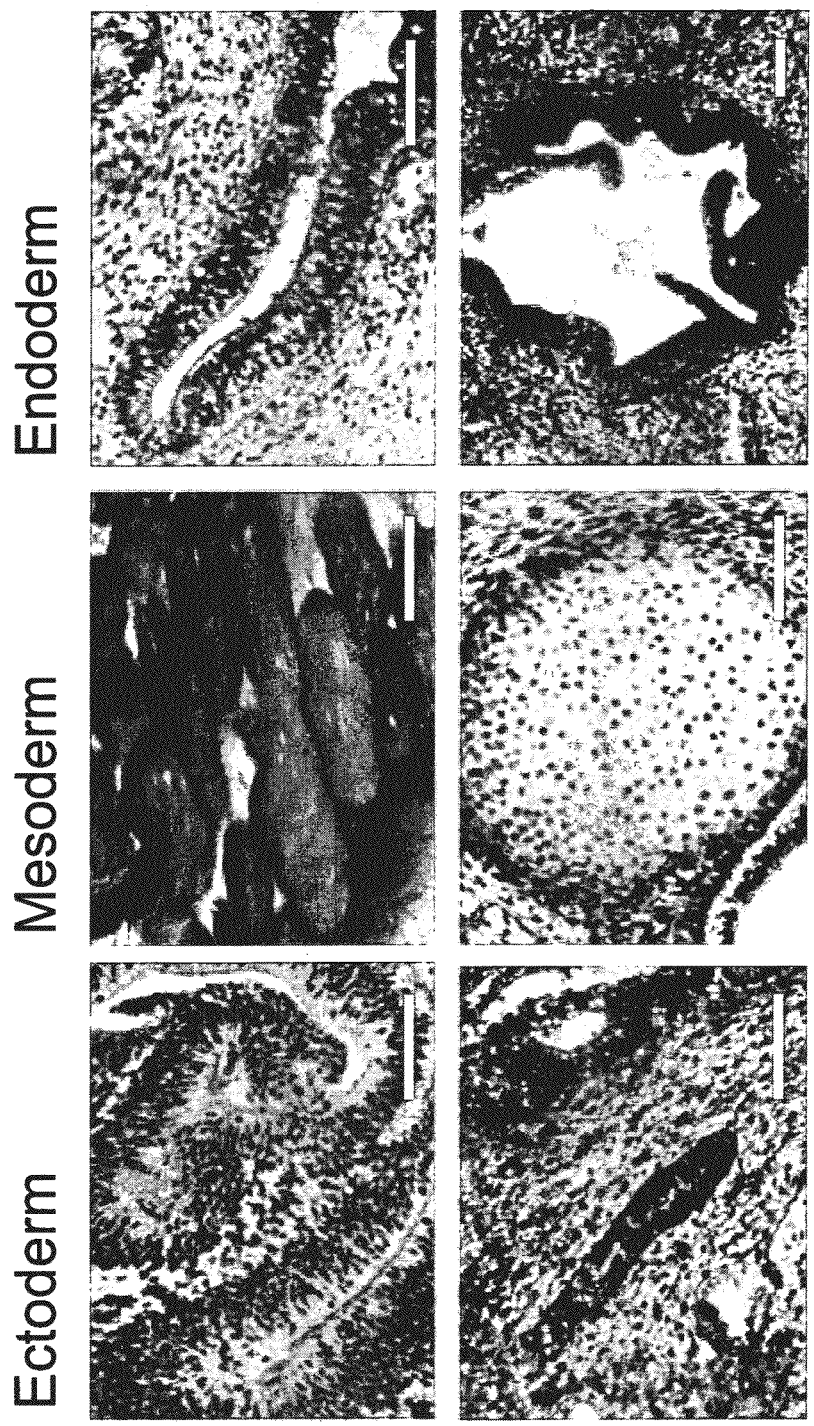

Genome-Wide RNAi Screen for Candidates Required for the Maintenance of hESC Identity:

Candidates for maintaining hESC identity were identified using a siRNA screen that uses GFP fluorescence as an indicator for the undifferentiated state of hESCs. A GFP reporter gene was placed under the control of a 3 kb POU5F1 upstream regulatory region which had been previously characterized [32]. This reporter construct was introduced into H1 hESC to generate a stable hESC line (FIG. 1A). When hESCs differentiate, the POU5F1 gene regulatory element will be silenced and correspondingly, the GFP expression will be reduced. The reliability and robustness of this reporter line was tested with a positive control siRNA (targeting POU5F1) and a negative control siRNA (non-targeting siRNA). Transfection of POU5F1 siRNA resulted in differentiation and a reduction in GFP, while negative control siRNA had no effect on GFP (FIGS. 2A and 2B). Therefore, GFP fluorescence was used as a proxy for the undifferentiated state of hESCs. Further characterization of the POU5F1-GFP reporter cell-line showed that they are normal with 46XY chromosomes (FIG. 2C) and they formed teratomas containing tissues of the ectoderm, mesoderm and endoderm lineages when injected into SCID mice (FIG. 2D).

For a high throughput screen in a 384-well format, one of the technical challenges is to ensure high transfection efficiency. To enable high transfection efficiency, the cells were dissociated into single cells and reverse transfected with the siRNA/transfection lipid complexes. As hESCs are known for their poor survival rate upon extensive dissociation, ROCK inhibitor was supplemented into the medium to protect singly dissociated cells from apoptosis [33]. A pilot experiment was performed to determine the optimized conditions (amount of transfection reagent and cell density) for reverse transfection.

A Z' factor of more than 0.5 was obtained from this pilot screen, indicating a robust dynamic range between the positive (GFP siRNA) and negative (non-targeting siRNA) controls for a high throughput screen.

Figure 1B:

Thereafter, the genome-wide siRNA screen was performed using the Dharmacon SMARTpooled siRNA library targeting 21,121 human genes. The siRNAs were printed onto 67 matrigel coated 384-well plates where each well contained a mixture of 4 siRNAs targeting a single gene. On each plate, negative controls (non-targeting siRNA) and positive controls (GFP siRNA and POU5F1 siRNA) were included in the designated wells. The screen was carried out in duplicates and the cells were imaged for GFP and Hoechst fluorescence 4 days after transfection (FIGS. 1A and 1B). The Z' factor for the entire screen was 0.76 and it was reproducibly greater than 0.5 as observed from the pilot screen.

The mean of the z-score for GFP fluorescence reduction ($F_{av}$) and nuclei number reduction ($N_{av}$) were calculated to generate a candidate list (data not shown). POU5F1, which is a key regulator in the maintenance of both mouse and human ESCs, ranked first for GFP fluorescence reduction, with a z-score of 5.15. In addition, several known pluripotency regulators including HCFC1, TCL1A, ZSCAN10, ZIC3, NANOG, ZNF143 and RIF1 were identified among the top 5% of the hits (FIG. 3A). PRDM14 and NFRKB demonstrated significant GFP fluorescence reduction with a z-score of 3.79 and 3.13, respectively. This correlates to PRDM14 and NFRKB being ranked $10^{th}$ and $21^{st}$, respectively, out of the 21,121 genes tested.

Figure 4A:
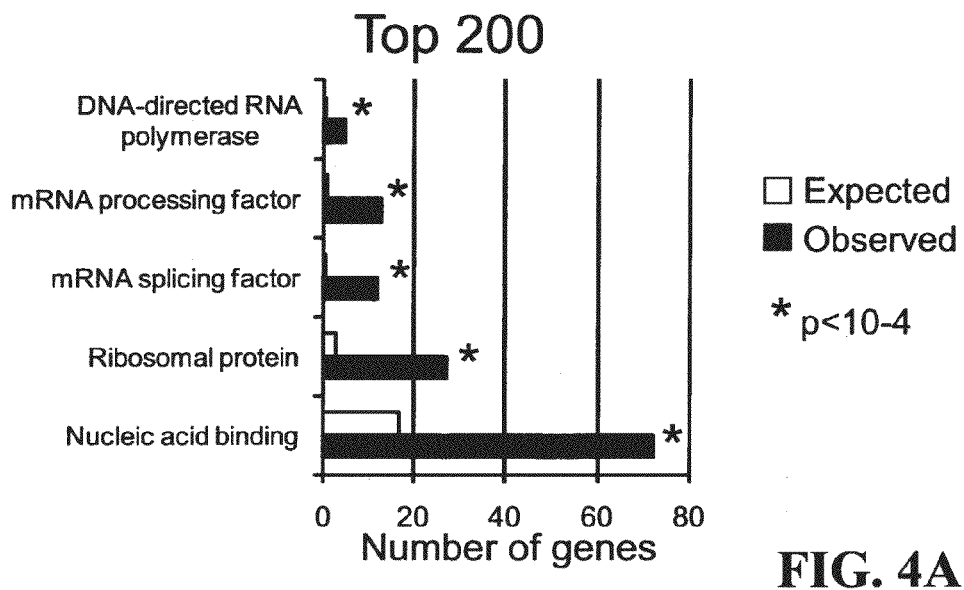
FIG. 4: Gene ontology analysis of $N_{av}$. (4A) Gene ontology analysis on the molecular function of the top 200 genes ranked by $N_{av}$ scores (Panther classification). Candidate genes involved in cell survivability were enriched in GO categories for nucleic acid binding and ribosomal proteins, mRNA splicing and processing factor and DNA-directed RNA polymerase. (4B) Transcripts encoding for RNA polymerase subunits were among the top 200 hits (ranked by $N_{av}$ score). (4C) Transcripts encoding for ribosomal subunits were found among the top hits.
Figure 4B:
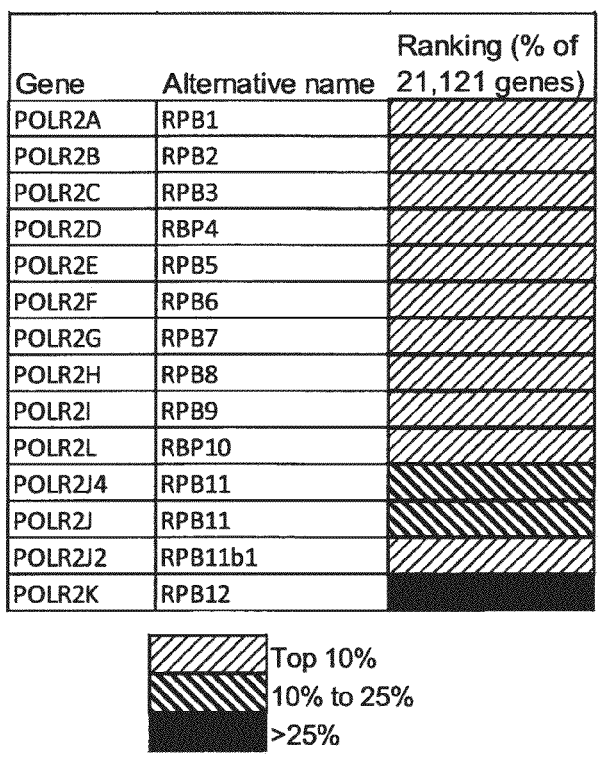
Figure 4C:
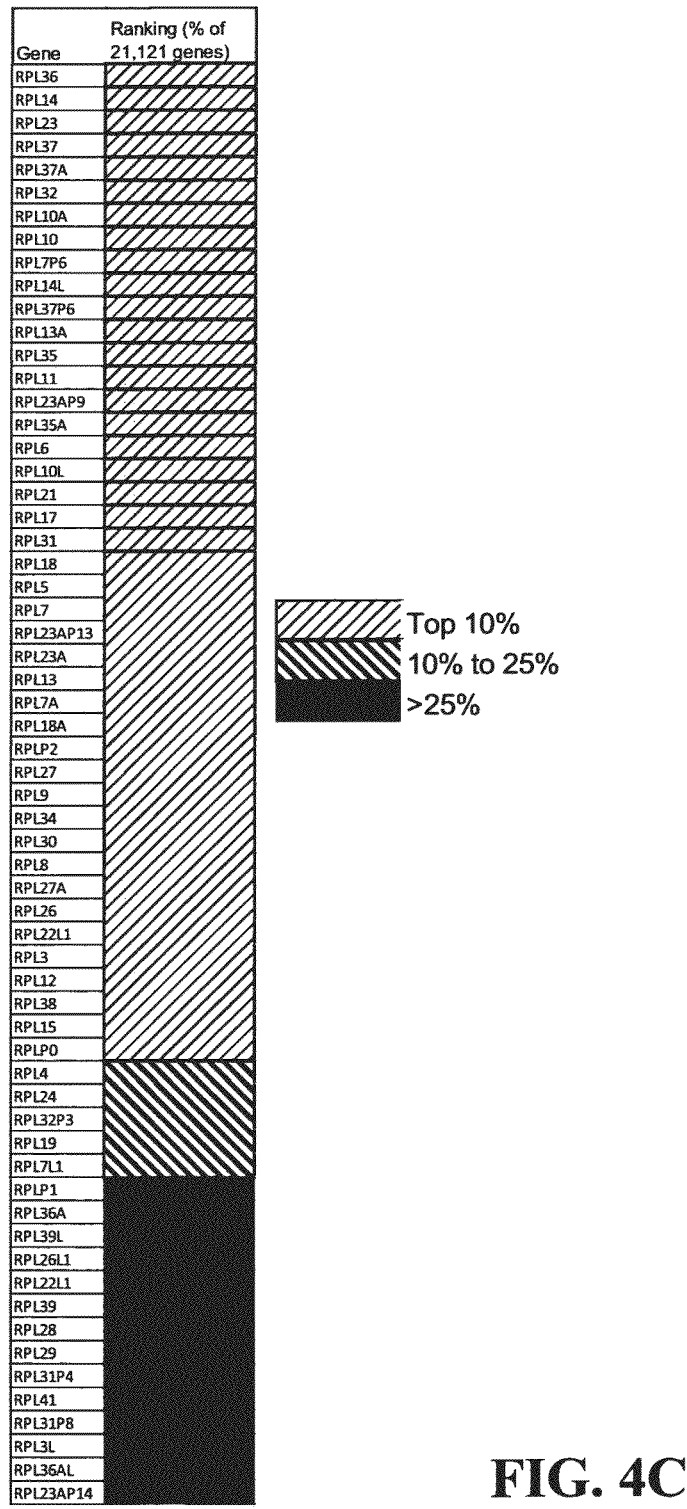

In addition to GFP fluorescence changes, the genes that could affect survivability of hESCs were analyzed by quantifying the nuclei number (data not shown). Gene ontology (GO) analysis of the top 200 genes ranked by $N_{av}$ score revealed that gene categories such as nucleic acid binding protein, ribosomal protein and DNA-directed RNA polymerase were significantly enriched (FIGS. 4A, 4B and 4C). This is expected given the essential roles of ribosomal proteins and RNA polymerase II complex in eukaryotes.

Figure 1C:
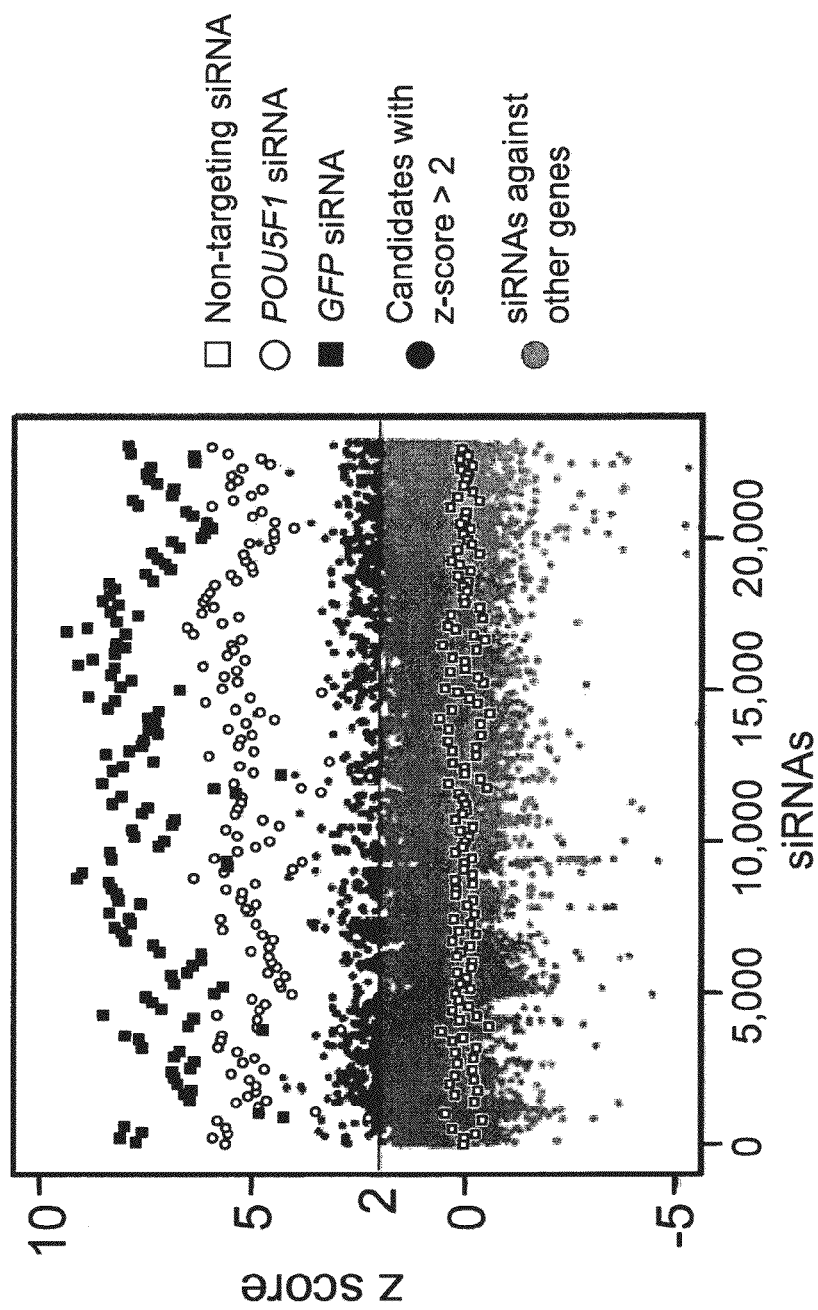
Figure 5A:
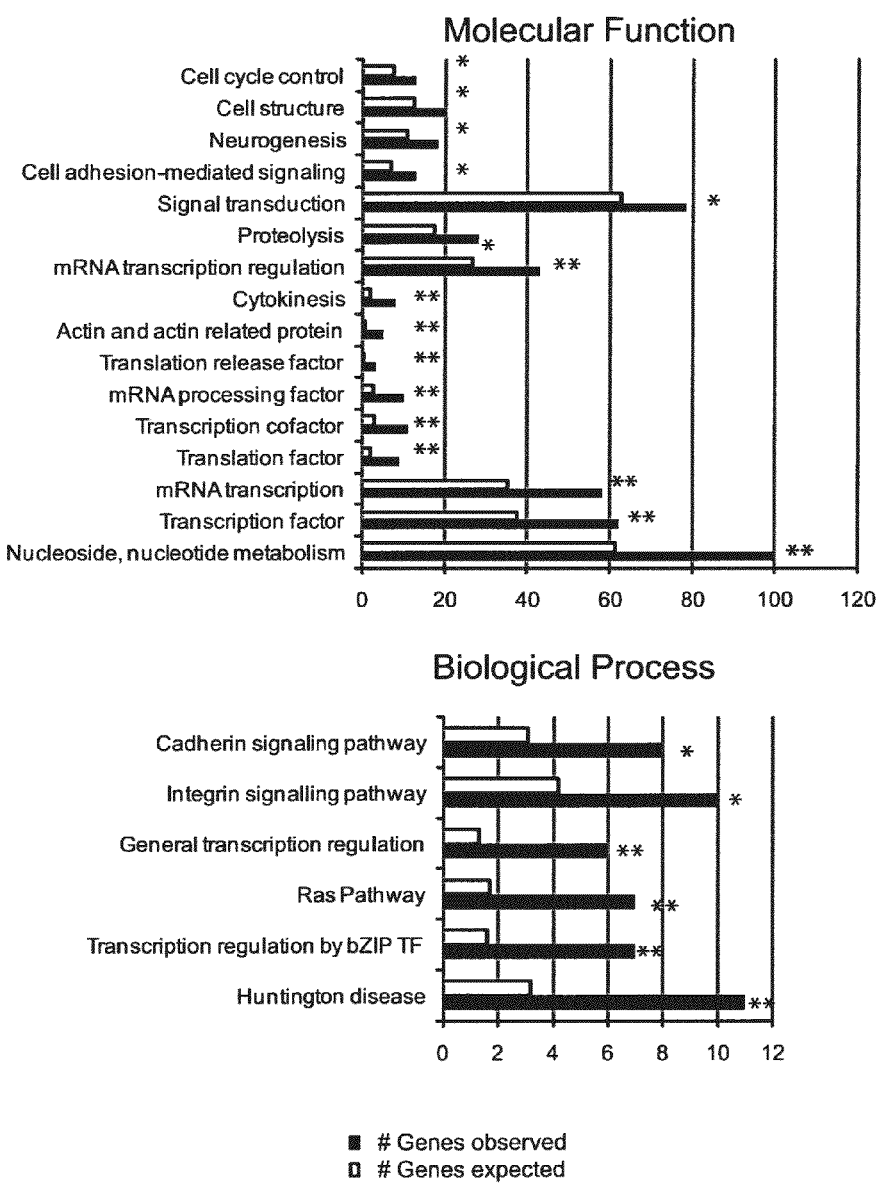
FIG. 5: Pathway analyses. (5A) Gene Ontology analysis of the 566 genes with z-score>2. Graphs represent the functional categorization of the biological process and molecular function categories that are over-represented. Categories with p-value<0.05 are indicated with * and categories with p-value<0.01 are indicated with **. (5B) Reactome analysis. The 566 genes (identifiers) were analyzed using the web-resource Reactome. The reactome map were plotted using Skypainter tool to determine which events (reactions and/or pathways) are statistically over-represented in the set of genes submitted. 113 identifiers could be matched to the 333 out of 4374 events. 12 categories with p-value<0.05 are over-represented. (5C) Interaction map. 263 genes were found to be interacting between/among themselves from the 566 genes. (5D) Components of the INO80 chromatin remodeling complex, mediator complex, TAF complex, COP9 signalosome, eukaryotic initiation complex and spliceosome complex with z-score>2 are indicated in with an asterisk (*). These complexes are assessed using the STRING database with a high confidence threshold.
Figure 5B:
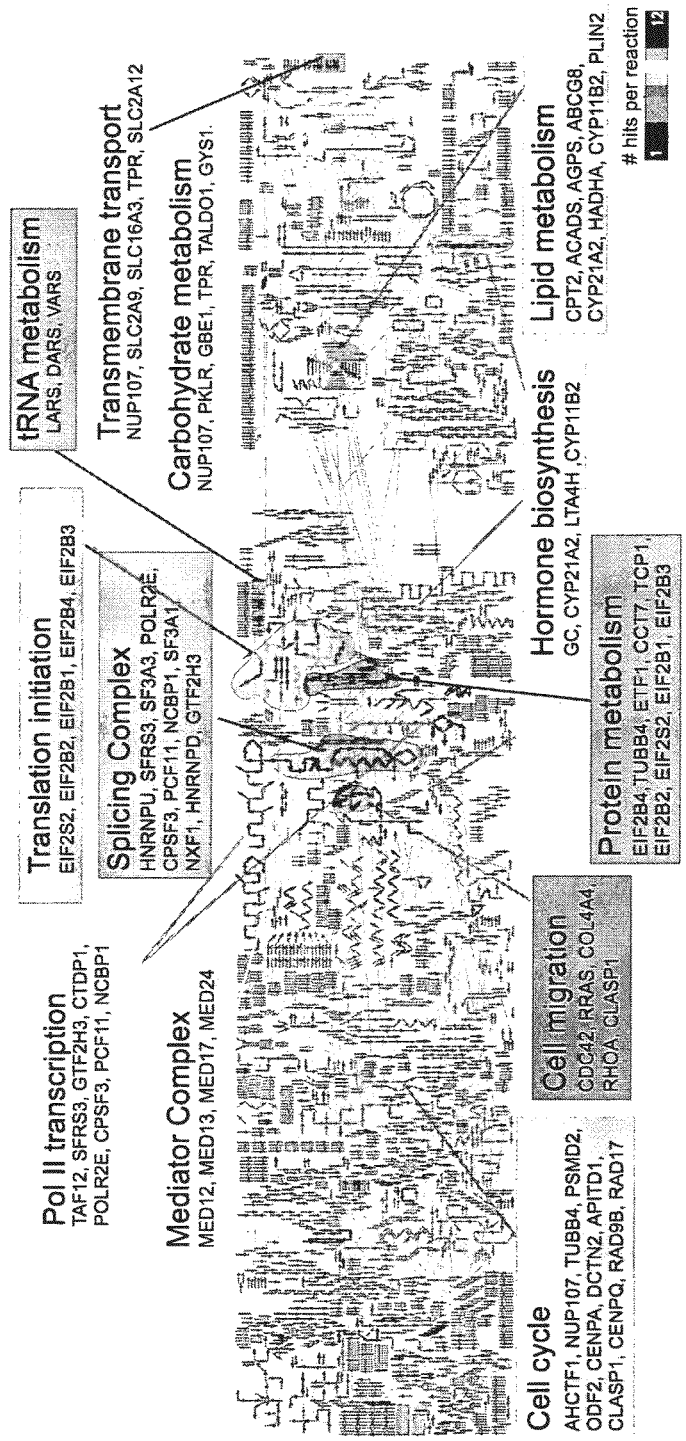
Figure 5C:
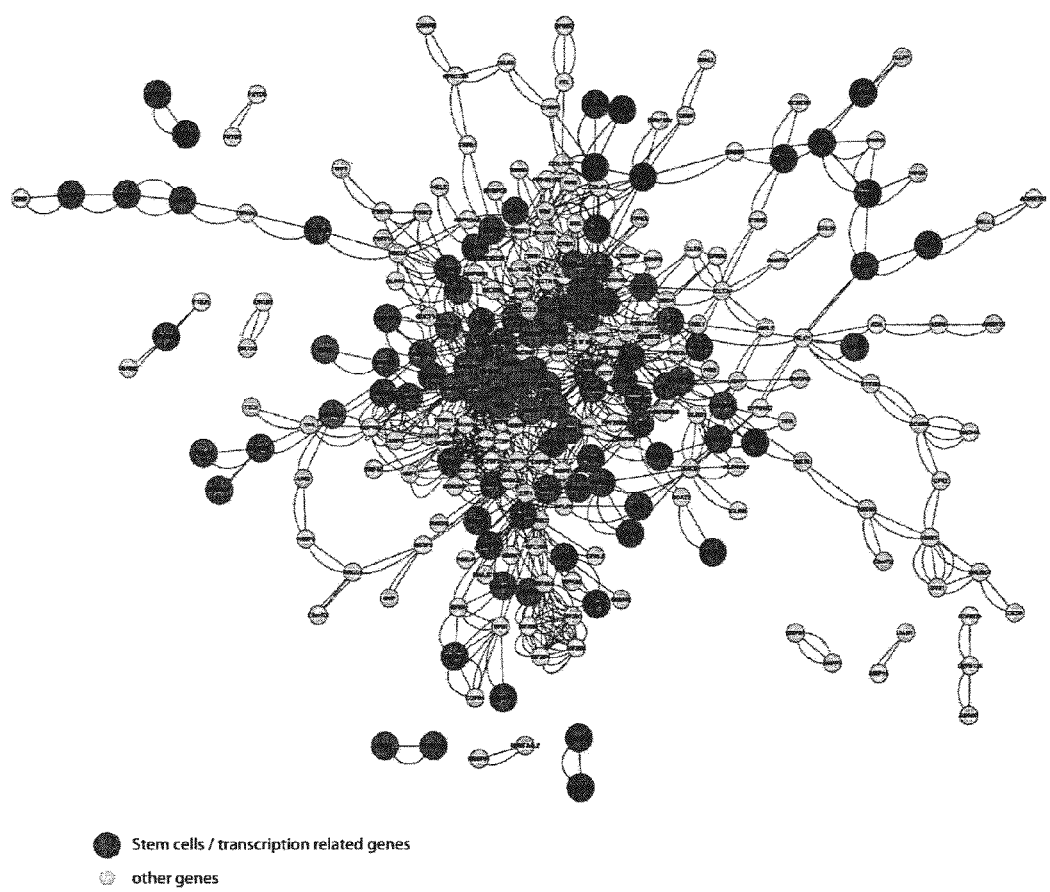
Figure 5D:
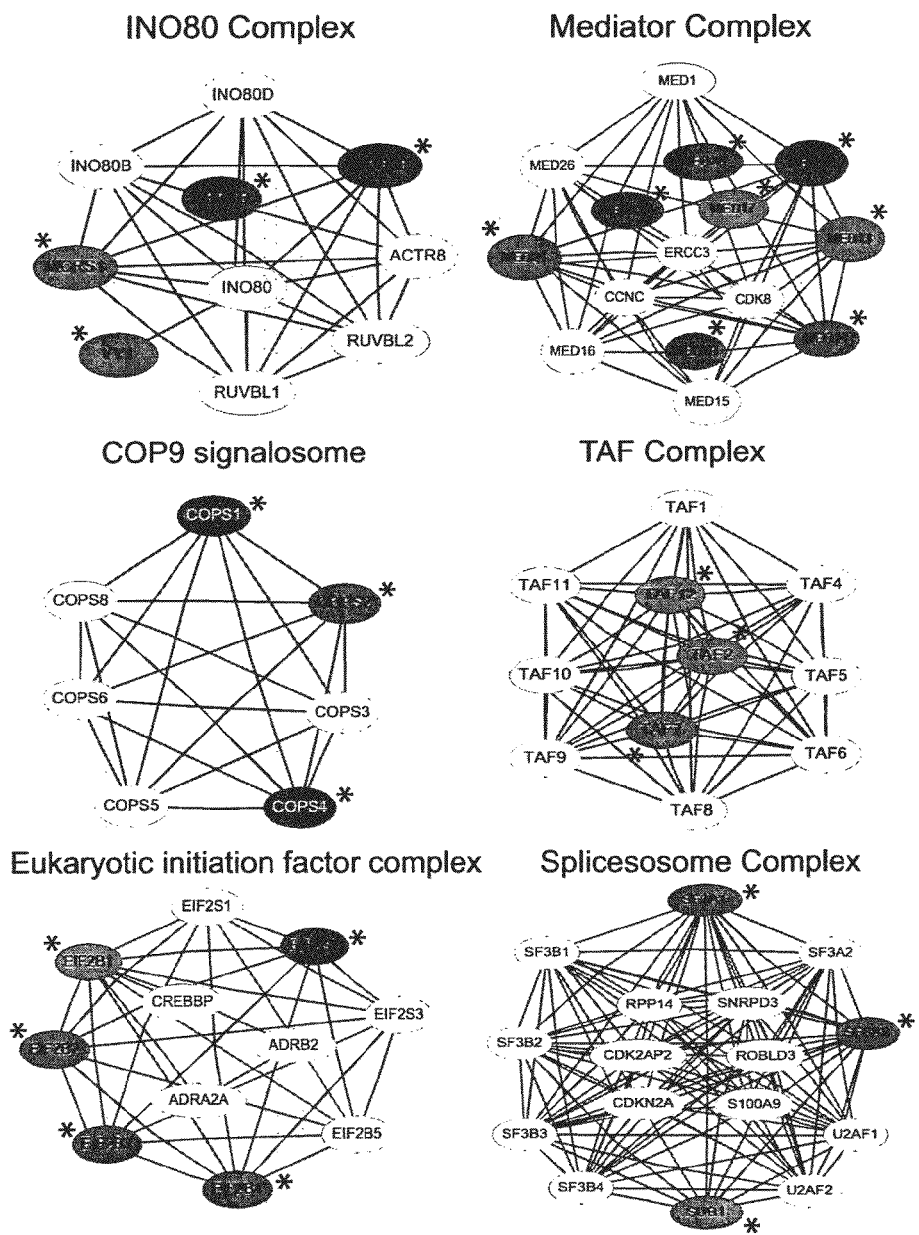

A $F_{av}$ z-score>2 (2 standard deviations from the negative controls) was set as the cutoff for a gene to be considered a potential candidate and 566 genes were obtained (FIG. 1C). GO analysis of the 566 genes showed enrichment for transcription factors and translation factors (FIG. 5A). Reactome analysis also revealed enrichment of pathways involved in transcription and translation (FIG. 5B, additional data not shown) [34]. The STRING database was used to uncover protein-protein interactions among the protein products encoded by the 566 genes (FIGS. 5C and 5D). Interestingly, components of the INO80 chromatin remodelling complex [35], the mediator complex [36], the COP9 signalosome [37], the TAF complex [38], the eukaryotic initiation factor complex [39], and spliceosome complex [40] were found among these candidates (FIG. 5D, FIGS. 3B and 3C). Hence, genes coding for proteins in known biochemical complexes which have not been previously implicated as important for hESCs were identified.

Next, a secondary validation screen for 200 candidates was performed. The majority of these candidates are found within the top 50% of the 566 primary hits. The pooled siRNAs for each gene were deconvoluted into 4 individual siRNAs, i.e. a total 800 of siRNAs targeting 200 genes. To further enhance the confidence of the hit genes, a multi-parametric approach was adopted where the importance of each gene in the maintenance of hESCs was assessed by different stemness markers of analysis and subjecting this mode of analysis on different hESCs cell lines. Since OCT4 and NANOG are key markers for pluripotency, in which depletion will induce differentiation, these 2 factors in addition to GFP (for the H1-GFP reporter cell only) were utilized as markers for assessing hESCs' stemness state.

Figure 6A:
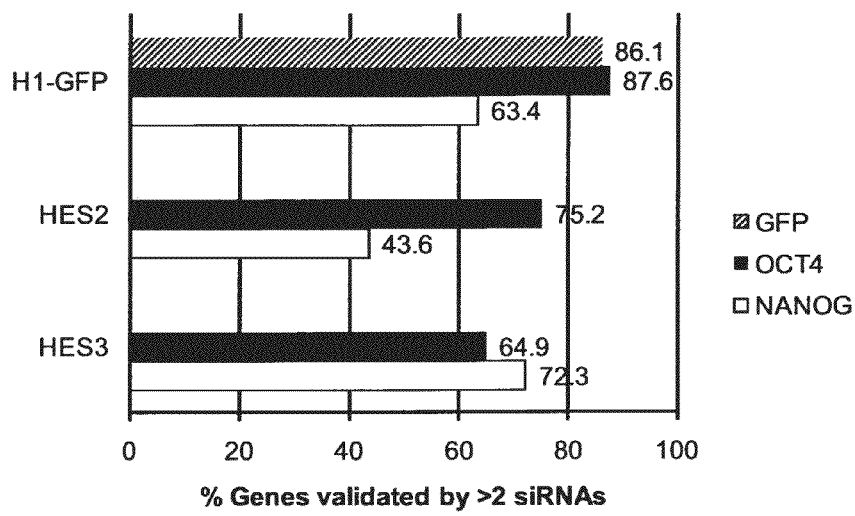
FIG. 6: Secondary validation of 200 genes. (6A) Deconvoluted siRNA screen on H1-GFP, HES2 and HES3 hESCs lines. 200 genes from the 566 genes with z-score>2 were subjected to further validation by deconvoluting the pooled mixture of 4 siRNAs. The screen was performed on 3 different hESCs lines and different stemness markers were used for analysis. H1-GFP hESCs line were analyzed for GFP, OCT4 and NANOG expression, HES2 and HES3 hESCs lines were analyzed for OCT4 and NANOG expression. Genes were considered positive hits if 2 or more siRNA down-regulate GFP/OCT4/NANOG expression. The percentage of genes that were validated/cell line/stemness marker are indicated beside the respective bars. (6B) Venn diagram showing the overlapping hits for the different marker of analysis in each of the different cell line. 126 genes are validated by GFP, OCT4 and NANOG downregulation in H1-GFP hESCs. 86 genes in HES2 and 124 genes in HES3 were validated based on OCT4 and NANOG downregulation. (6C) Venn diagram showing the common overlapping genes among the 3 different hESC lines based on OCT4 or NANOG stemness marker for analysis. 93 common genes are involved in the downregulation of OCT4 and 54 common genes are involved in the down regulation of NANOG in all the 3 hESCs lines. (6D) Graphs depicting the GFP VS OCT4, GFP VS NANOG correlation for H1-GFP hESCs and NANOG VS OCT4 correlation for each of H1-GFP, HES2 and HES3 hESCs.
Figure 6B:
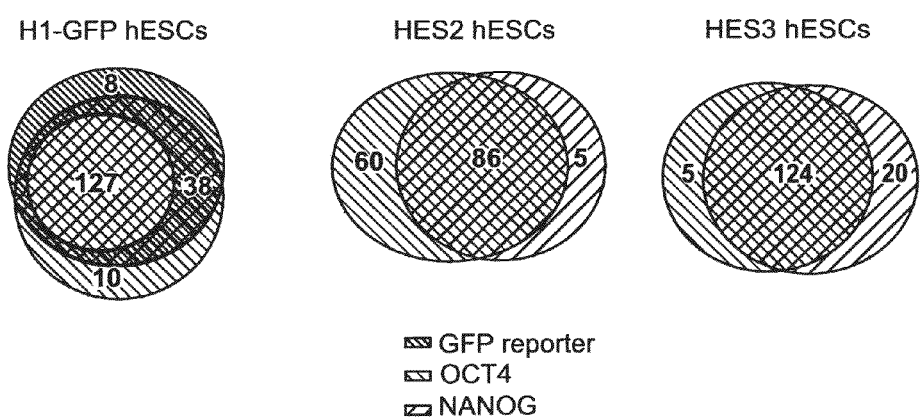

For the secondary screen, a threshold cutoff of 0.75 (equivalent to 2 S.D. from the negative control in the primary screen) was set and the number of siRNAs that down-regulated OCT4/NANOG/POU5F1-GFP expression to below the threshold were scored. The candidates were considered positive if the assay of assessment was scored by at least 2 siRNAs. For H1-GFP hESCs, the validation rate based on the reduction of GFP reporter, OCT4 and NANOG expression were 86.1%, 87.6% and 63.4% respectively and 127 common genes were obtained with the 3 stemness markers of assessment (FIGS. 6A and 6B). The 127 common genes are listed in Table 1 below:

TABLE 1

| H1-GFP hESCs - Common Genes for GFP, OCT4 and NANOG | |
| --- | --- |
| 1 | ABP1 |
| 2 | ABTB1 |
| 3 | ADA |
| 4 | ADAMTS1 |
| 5 | ANGPT4 |
| 6 | ANXA4 |
| 7 | APLP2 |
| 8 | BDP1 |
| 9 | BENE |
| 10 | C22ORF16 |
| 11 | CAPN2 |
| 12 | CDC42 |
| 13 | CGGBP1 |
| 14 | COL11A1 |
| 15 | COPS4 |
| 16 | CPSF3 |
| 17 | CREBL2 |
| 18 | CRLF1 |
| 19 | CRSP2 |
| 20 | CYBA |
| 21 | DEFB126 |
| 22 | DKFZP564B147 |
| 23 | DKFZP564K142 |
| 24 | E4F1 |
| 25 | EDF1 |
| 26 | EIF2B1 |
| 27 | EIF2B2 |
| 28 | EIF2B3 |
| 29 | EIF2B4 |
| 30 | EIF2S2 |
| 31 | ELYS |
| 32 | ENPP7 |
| 33 | ETF1 |
| 34 | FAM19A1 |
| 35 | FLJ20898 |
| 36 | FLJ23447 |
| 37 | FLJ25439 |
| 38 | FLJ32954 |
| 39 | FLJ46536 |
| 40 | FLJ90652 |
| 41 | FTSJ1 |
| 42 | GJA8 |
| 43 | GLRB |
| 44 | GLTSCR1 |
| 45 | GPS1 |
| 46 | GUSB |
| 47 | H1FX |
| 48 | HCFC1 |
| 49 | HELZ |
| 50 | HEMK1 |
| 51 | HES6 |
| 52 | HNRPU |
| 53 | IGFBP6 |
| 54 | INCA1 |
| 55 | KIR3DL1 |
| 56 | KIRREL2 |
| 57 | LARS |
| 58 | LCMR1 |

TABLE 1-continued

H1-GFP hESCs - Common Genes for GFP, OCT4 and NANOG

| | |
|---|---|
| 59 | LIF |
| 60 | LOC124245 |
| 61 | LOC374654 |
| 62 | LOC390790 |
| 61 | LOC400221 |
| 64 | LOC56901 |
| 65 | LRRC33 |
| 66 | LUC7A |
| 67 | MBTD1 |
| 68 | MCRS1 |
| 69 | MGC10471 |
| 70 | MGC21874 |
| 71 | MGC32871 |
| 72 | MGC39827 |
| 73 | MMP15 |
| 74 | MOCS1 |
| 75 | MR1 |
| 76 | MVP |
| 77 | NANOG |
| 78 | NCBP1 |
| 79 | NEUROD2 |
| 80 | NFRKB |
| 81 | NPEPL1 |
| 82 | NUDT8 |
| 83 | NUP107 |
| 84 | NXF1 |
| 85 | ODF2 |
| 86 | PCF11 |
| 87 | PDZK11 |
| 88 | PHB |
| 89 | POLH |
| 90 | POU5F1 |
| 91 | PPAPDC2 |
| 92 | PRDM14 |
| 93 | PROP1 |
| 94 | PSMD2 |
| 94 | PXN |
| 96 | RASEF |
| 97 | REA |
| 98 | RHOA |
| 99 | RPESP |
| 100 | SAMD7 |
| 101 | SERPINB2 |
| 102 | SF3A1 |
| 103 | SF3A3 |
| 104 | SFPQ |
| 105 | SFRS3 |
| 106 | SFXN3 |
| 107 | SOAT2 |
| 108 | SON |
| 109 | SOX14 |
| 110 | SUV39H2 |
| 111 | TAF2 |
| 112 | TBC1D10 |
| 113 | THRAP2 |
| 114 | TMEM14B |
| 115 | TNRC11 |
| 116 | TPD52L1 |
| 117 | TPM1 |
| 118 | TPR |
| 119 | TRIP |
| 120 | TRPA1 |
| 121 | VMP |
| 122 | YY1 |
| 123 | ZFP36 |
| 124 | ZIC4 |
| 125 | ZNF206 |
| 126 | ZNF35 |
| 127 | ZNF434 |

The secondary screen was extended to 2 other hESC lines; HES2 and HES3. For HES2 hESCs, 86 common genes were obtained based on OCT4 and NANOG expression and the validation rate was 75.2% and 43.6%, respectively (FIGS. 6A and 6B). The 86 common genes are listed in Table 2 below:

TABLE 2

HES2 hESCs - Common Genes for OCT4 and NANOG

| | |
|---|---|
| 1 | ANKRD1 |
| 2 | ANXA4 |
| 3 | ATOH8 |
| 4 | BCL6B |
| 5 | BDP1 |
| 6 | BENE |
| 7 | C22ORF16 |
| 8 | CAMP |
| 9 | CAPN2 |
| 10 | CDC42 |
| 11 | CDX2 |
| 12 | CPSF3 |
| 13 | CREBL2 |
| 14 | CRSP2 |
| 15 | CYBA |
| 16 | E4F1 |
| 17 | EIF2B2 |
| 18 | EIF2B3 |
| 19 | EIF2B4 |
| 20 | EIF2S2 |
| 21 | ELYS |
| 22 | EP300 |
| 23 | ETF1 |
| 24 | FAM19A1 |
| 25 | FLJ90652 |
| 26 | FOXJ3 |
| 27 | FTL |
| 28 | FTSJ1 |
| 29 | GSPT1 |
| 30 | GUSB |
| 31 | H1FX |
| 32 | HCFC1 |
| 33 | HELZ |
| 34 | HEMK1 |
| 35 | HES6 |
| 36 | HIVEP3 |
| 37 | HNRPU |
| 38 | IGFBP6 |
| 39 | JMJD2B |
| 40 | KIAA0274 |
| 41 | KLK5 |
| 42 | LCMR1 |
| 43 | LIF |
| 44 | LOC390790 |
| 45 | MGC10471 |
| 46 | MGC21874 |
| 47 | MGC39827 |
| 48 | MMP15 |
| 49 | MR1 |
| 50 | NANOG |
| 51 | NCBP1 |
| 52 | NFRKB |
| 53 | NPEPL1 |
| 54 | NUP107 |
| 55 | NXF1 |
| 56 | PCF11 |
| 57 | PDZK11 |
| 58 | PHB |
| 59 | POU5F1 |
| 60 | PRDM14 |
| 61 | PRDM9 |
| 62 | PRO2730 |
| 63 | PROP1 |
| 64 | PSMD2 |
| 65 | PSTPIP2 |
| 66 | PXN |
| 67 | RASEF |
| 68 | REA |
| 69 | SF3A1 |
| 70 | SF3A3 |
| 71 | SFPQ |
| 72 | SFRS3 |
| 73 | SON |
| 74 | SOX14 |
| 75 | SUV39H2 |
| 76 | TAF7 |
| 77 | TBC1D10 |
| 78 | TCL1A |

TABLE 2-continued

HES2 hESCs - Common Genes for OCT4 and NANOG

| | |
|---|---|
| 79 | TNRC11 |
| 80 | TPR |
| 81 | VWF |
| 82 | ZFP64 |
| 83 | ZIC4 |
| 84 | ZNF136 |
| 85 | ZNF206 |
| 86 | ZNF434 |

Likewise, measuring OCT4 and NANOG expression in HES3 hESCs yielded 124 common genes with a validation rate of 64.9% and 72.3%, respectively (FIGS. 6A and 6B). The 124 common genes are listed in Table 3 below:

TABLE 3

HES3 hESCs - Common Genes for OCT4 and NANOG

| | |
|---|---|
| 1 | ADAMTS1 |
| 2 | AGPS |
| 3 | ANGPT4 |
| 4 | ANXA4 |
| 5 | ATOH8 |
| 6 | BCL6B |
| 7 | BDP1 |
| 8 | CAPN2 |
| 9 | CDC42 |
| 10 | CDX2 |
| 11 | CGGBP1 |
| 12 | COL11A1 |
| 13 | CREBL2 |
| 14 | CRK7 |
| 15 | CRLF1 |
| 16 | DDIT3 |
| 17 | DEFB126 |
| 18 | DKFZP564B147 |
| 19 | E4F1 |
| 20 | EDF1 |
| 21 | EIF2B1 |
| 22 | EIF2B2 |
| 23 | EIF2B3 |
| 24 | EIF2B4 |
| 25 | EIF2S2 |
| 26 | ELYS |
| 27 | ENPP7 |
| 28 | ETF1 |
| 29 | FLJ23447 |
| 30 | FLJ25439 |
| 31 | FLJ25952 |
| 32 | FLJ38508 |
| 33 | FLJ46536 |
| 34 | FLJ90652 |
| 35 | FTSJ1 |
| 36 | FUBP1 |
| 37 | GLTSCR1 |
| 38 | GPS1 |
| 39 | GSPT1 |
| 40 | GUSB |
| 41 | H1FX |
| 42 | HCFC1 |
| 43 | HELZ |
| 44 | HEMK1 |
| 45 | HNRPU |
| 46 | IBSP |
| 47 | IGFBP6 |
| 48 | INCA1 |
| 49 | JMJD2B |
| 50 | KIAA1076 |
| 51 | KIRREL2 |
| 52 | KLK5 |
| 53 | LARS |
| 54 | LCE1E |
| 55 | LCMR1 |
| 56 | LOC124245 |
| 57 | LOC390790 |

TABLE 3-continued

HES3 hESCs - Common Genes for OCT4 and NANOG

| | |
|---|---|
| 58 | LOC56901 |
| 59 | LPPR2 |
| 60 | LRRC33 |
| 61 | LUC7A |
| 62 | MAP2K7 |
| 63 | MCRS1 |
| 64 | MGC21874 |
| 65 | MGC39827 |
| 66 | MMP15 |
| 67 | MMP24 |
| 68 | MOCS1 |
| 69 | MR1 |
| 70 | MVP |
| 71 | NANOG |
| 72 | NCBP1 |
| 73 | NFRKB |
| 74 | NPEPL1 |
| 75 | NUP107 |
| 76 | NXF1 |
| 77 | OACT1 |
| 78 | ODF2 |
| 79 | PCF11 |
| 80 | PDZK11 |
| 81 | PHB |
| 82 | PITX1 |
| 83 | POU5F1 |
| 84 | PPAPDC2 |
| 85 | PPP2R3A |
| 86 | PRDM9 |
| 87 | PRO2730 |
| 88 | PROP1 |
| 89 | PSMD2 |
| 90 | PSTPIP2 |
| 91 | PXN |
| 92 | RBM17 |
| 93 | REA |
| 94 | RPESP |
| 94 | RRAS |
| 96 | SAMD7 |
| 97 | SF3A1 |
| 98 | SF3A3 |
| 99 | SFPQ |
| 100 | SFRS3 |
| 101 | SOAT2 |
| 102 | SON |
| 103 | SOX14 |
| 104 | SPI1 |
| 105 | SUV39H2 |
| 106 | SYNCRIP |
| 107 | TAF2 |
| 108 | TAF7 |
| 109 | THRAP4 |
| 110 | TMEM14B |
| 111 | TPD52L1 |
| 112 | TPM1 |
| 113 | TPR |
| 114 | TRIP15 |
| 115 | TRPA1 |
| 116 | ULK2 |
| 117 | VMP |
| 118 | XRCC1 |
| 119 | ZFP64 |
| 120 | ZNF136 |
| 121 | ZNF138 |
| 122 | ZNF206 |
| 123 | ZNF35 |
| 124 | ZNF43 |

Figure 6C:
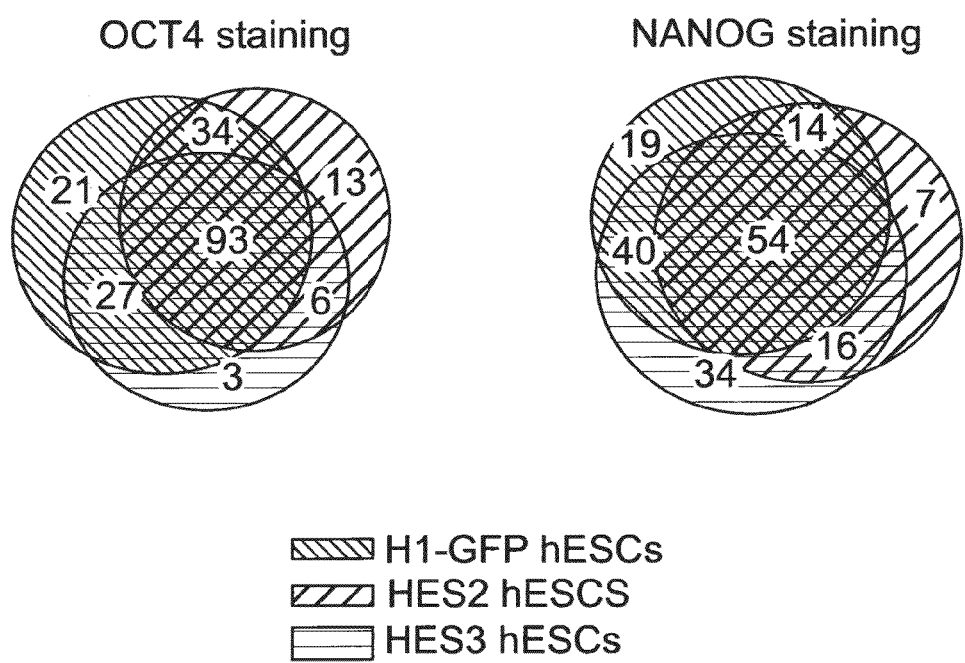

The higher validation rate for H1-GFP hESCs as compared to other hESC lines corroborated the fact that the same cell line was used for the primary screen. Thus, 93 genes were identified that down-regulated OCT4 expression (see Table 4, below) and 54 genes that down-regulated NANOG expression (see Table 5, below) in the 3 different hESC lines (FIG. 6C).

TABLE 4

Genes that down-regulated OCT4 in all 3 hESCs

| | |
|---|---|
| 1 | AGPS |
| 2 | ANXA4 |
| 3 | ATOH8 |
| 4 | BDP1 |
| 5 | BENE |
| 6 | CAPN2 |
| 7 | CDC42 |
| 8 | CDX2 |
| 9 | COL11A1 |
| 10 | CREBL2 |
| 11 | CRK7 |
| 12 | DDIT3 |
| 13 | DEFB126 |
| 14 | E4F1 |
| 15 | EDF1 |
| 16 | EIF2B1 |
| 17 | EIF2B2 |
| 18 | EIF2B3 |
| 19 | EIF2B4 |
| 20 | EIF2S2 |
| 21 | ELYS |
| 22 | ENPP7 |
| 23 | ETF1 |
| 24 | FLJ90652 |
| 25 | FTSJ1 |
| 26 | FUBP1 |
| 27 | GLTSCR1 |
| 28 | GPS1 |
| 29 | GSPT1 |
| 30 | GUSB |
| 31 | H1FX |
| 32 | HCFC1 |
| 33 | HELZ |
| 34 | HEMK1 |
| 35 | HNRPU |
| 36 | IGFBP6 |
| 37 | INCA1 |
| 38 | JMJD2B |
| 39 | KLK5 |
| 40 | LARS |
| 41 | LCE1E |
| 42 | LCMR1 |
| 43 | LIF |
| 44 | LOC124245 |
| 45 | LOC390790 |
| 46 | LOC56901 |
| 47 | LPPR2 |
| 48 | LUC7A |
| 49 | MGC21874 |
| 50 | MGC39827 |
| 51 | MMP15 |
| 52 | MMP24 |
| 53 | MOCS1 |
| 54 | MR1 |
| 55 | NANOG |
| 56 | NCBP1 |
| 57 | NFRKB |
| 58 | NPEPL1 |
| 59 | NUP107 |
| 60 | NXF1 |
| 61 | ODF2 |
| 62 | PCF11 |
| 63 | PDZK11 |
| 64 | PHB |
| 65 | POU5F1 |
| 66 | PPAPDC2 |
| 67 | PRDM14 |
| 68 | PRDM9 |
| 69 | PRO2730 |
| 70 | PROP1 |
| 71 | PSMD2 |
| 72 | PSTPIP2 |
| 73 | PXN |
| 74 | REA |
| 75 | RPESP |
| 76 | RRAS |
| 77 | SAMD7 |
| 78 | SF3A1 |
| 79 | SF3A3 |
| 80 | SFPQ |
| 81 | SFRS3 |
| 82 | SOAT2 |
| 83 | SON |
| 84 | SOX14 |
| 85 | SPI1 |
| 86 | SUV39H2 |
| 87 | TAF7 |
| 88 | TPD52L1 |
| 89 | TPR |
| 90 | ZFP64 |
| 91 | ZNF136 |
| 92 | ZNF206 |
| 93 | ZNF43 |

TABLE 5

Genes that down-regulated NANOG in all 3 hESCs

| | |
|---|---|
| 1 | ANXA4 |
| 2 | BDP1 |
| 3 | CAPN2 |
| 4 | CDC42 |
| 5 | CGGBP1 |
| 6 | CREBL2 |
| 7 | CYBA |
| 8 | E4F1 |
| 9 | EIF2B2 |
| 10 | EIF2B3 |
| 11 | EIF2B4 |
| 12 | EIF2S2 |
| 13 | ELYS |
| 14 | ETF1 |
| 15 | FAM19A1 |
| 16 | FLJ90652 |
| 17 | FTSJ1 |
| 18 | GUSB |
| 19 | H1FX |
| 20 | HCFC1 |
| 21 | HELZ |
| 22 | HEMK1 |
| 23 | HNRPU |
| 24 | IGFBP6 |
| 25 | LCMR1 |
| 26 | LOC390790 |
| 27 | MCRS1 |
| 28 | MGC21874 |
| 29 | MGC39827 |
| 30 | MMP15 |
| 31 | MR1 |
| 32 | NANOG |
| 33 | NCBP1 |
| 34 | NFRKB |
| 35 | NPEPL1 |
| 36 | NUP107 |
| 37 | NXF1 |
| 38 | PCF11 |
| 39 | PDZK11 |
| 40 | PHB |
| 41 | POU5F1 |
| 42 | PROP1 |
| 43 | PSMD2 |
| 44 | PXN |
| 45 | REA |
| 46 | SF3A1 |
| 47 | SF3A3 |
| 48 | SFPQ |
| 49 | SFRS3 |
| 50 | SON |
| 51 | SOX14 |
| 52 | SUV39H2 |
| 53 | TPR |
| 54 | ZNF206 |

Figure 6D:
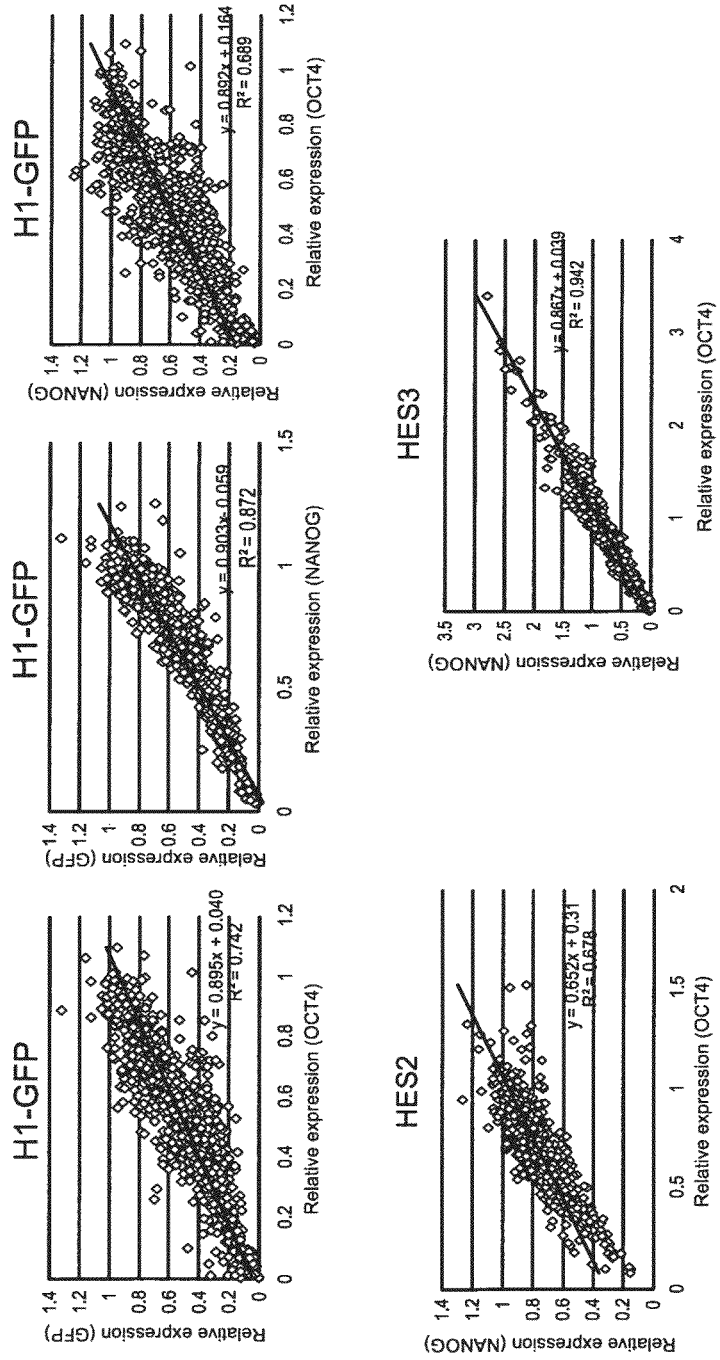

In addition, a positive correlation was observed between the different stemness markers (FIG. 6D). Overall, the secondary validation assay enabled the selection of genes for further functional assays for pluripotency. In particular, PRDM14 and NFRKB were identified for further analysis.

Example 2

Detailed below are exemplary methods of inducing pluripotency in human somatic cells, and maintaining pluripotency in hESCs, using PRDM14 and NFRKB.

PRDM14 and NFRKB Enhance Reprogramming of Human Somatic Cells:

Pluripotency can be reinstated in somatic cells through the introduction of defined transcription factors [41]. In human cells, OCT4, SOX2, KLF4 and c-MYC can reprogram human fibroblasts into human iPSCs (hiPSCs) [27, 42-44]. To date, a limited number of transcription factors such as NANOG, UTF1 and SALL4 have been shown to mediate reprogramming in conjunction with OCT4, SOX2 and/or KLF4 [44-46].

Figure 7A:
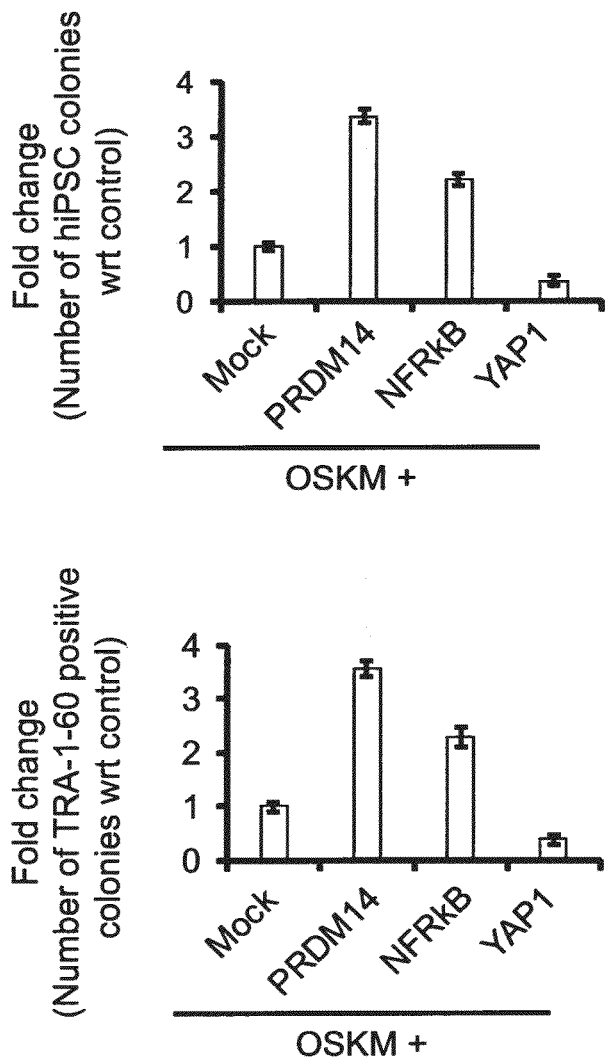
FIG. 7: PRDM14 and NFRKB can enhance reprogramming of human fibroblasts to iPSCs. (7A) Graph depicts fold change of the number of hESC-like iPSC colonies generated from PRDM14, NFRKB or YAP1 in conjunction with OCT4, SOX2, KLF4 and c-MYC (OSKM) with respect to the control (OSKM) (upper panel). Samples were subsequently fixed for immuno-staining, and the number of TRA-1-60 positive colonies was recorded (lower panel). Each column represents the average of 3 replicates. All values are means±s.e.m from 3 independent experiments (n=3). (7B) PRDM14 and NFRKB are required for reprogramming of human somatic cell. Retroviruses harboring PRDM14 shRNA or NFRKB shRNA were co-transduced with the 4 reprogramming factors. 2 independent shRNAs were used for the depletion of either PRDM14 or NFRKB. The number of hESC-like iPSC colonies was counted after 4 weeks post infection (upper panel). Samples were subsequently fixed for immunofluorescence staining, and the number of TRA-1-60 positive colonies was recorded (lower panel). All values are means±s.e.m from 3 independent experiments (n=3). (7C) Bright field images show MRC-5 human embryonic lung fibroblasts and iPSC colonies induced by PRDM14 or NFRKB in combination with the 4 factors. Immunofluorescence staining detects hESC markers (NANOG, TRA-1-60, TRA-1-81 and SSEA-4) in PRDM14 or NFRKB-induced hiPSCs. These hiPSC colonies were also stained for alkaline phosphatase (AP). The scale bars represent 200 μm in bright field and IF images, and 2 mm in the AP staining image. (7D) Both OSKM+PRDM14 hiPSCs and OSKM+NFRKB hiPSCs showed normal karyotype. (7E) In vitro differentiation of hiPSCs. Both PRDM14 and NFRKB-induced hiPSCs can differentiate into different lineages via EB (embryoid body)-mediated or growth factor-induced in vitro differentiation. The hiPSCs can differentiate into ectodermal (indicated by NESTIN staining) and mesodermal cells (indicated by α-smooth muscle actin staining) using EB-mediated method. Definitive endodermal cells (as shown by staining for SOX17) derived with activin A induction and trophectodermal cells (as shown by staining for p57kip2) derived with combined BMP4 induction and FGF inhibition (PD0325901) were also obtained from these hiPSCs. The scale bars represent 200 μm. (7F) Teratoma formation assay for OSKM+PRDM14 hiPSCs and OSKM+NFRKB hiPSCs. Tissues derived from all three germ layers (ectoderm, mesoderm and endoderm) were obtained. Tissues shown correspond to pigmented epithelium, neural rosettes, muscle and gut epithelium. Bars represent 50 μm. (7G) Microarray profiling of hiPSCs. Heatmap showing the gene expression profile of 1,000 hESC-associated genes and fibroblast-associated genes in H1, H9 hESCs, two hiPSC lines and MRC-5. The selection of genes was based on the fold differences in their expression levels in hESCs and fibroblasts. The genes were sorted according to the average expression ratios and mean-centred around the fibroblasts signal. The greyscale bar indicates the gene expression normalized to fibroblasts in log 2 scale. (7H) DNA methylation analysis of hiPSCs. POU5F1 and NANOG promoter regions in H1 hESCs, MRC-5, PRDM14-induced hiPSCs and NFRKB-induced hiPSCs were analyzed by bisulfite sequencing. Each row of squares represents an individual sequencing result. Grey squares represent unmethylated. CpG dinucleotides; black squares represent methylated CpG dinucleotides.

To assess the role of PRDM14, NFRKB and YAP1, human fibroblasts were transduced with retroviruses containing expression constructs for OCT4 (O), SOX2 (S), KLF4 (K), and c-MYC (M) to generate hiPSC colonies that resembled hESCs. Interestingly, the number of hiPSC colonies was increased by 3.5 fold when human fibroblasts were co-introduced PRDM14 (P) along with OSKM (FIG. 7A). NFRKB (N) enhanced reprogramming by 2 fold, while YAP1 did not show a positive effect on reprogramming.

Figure 7B:
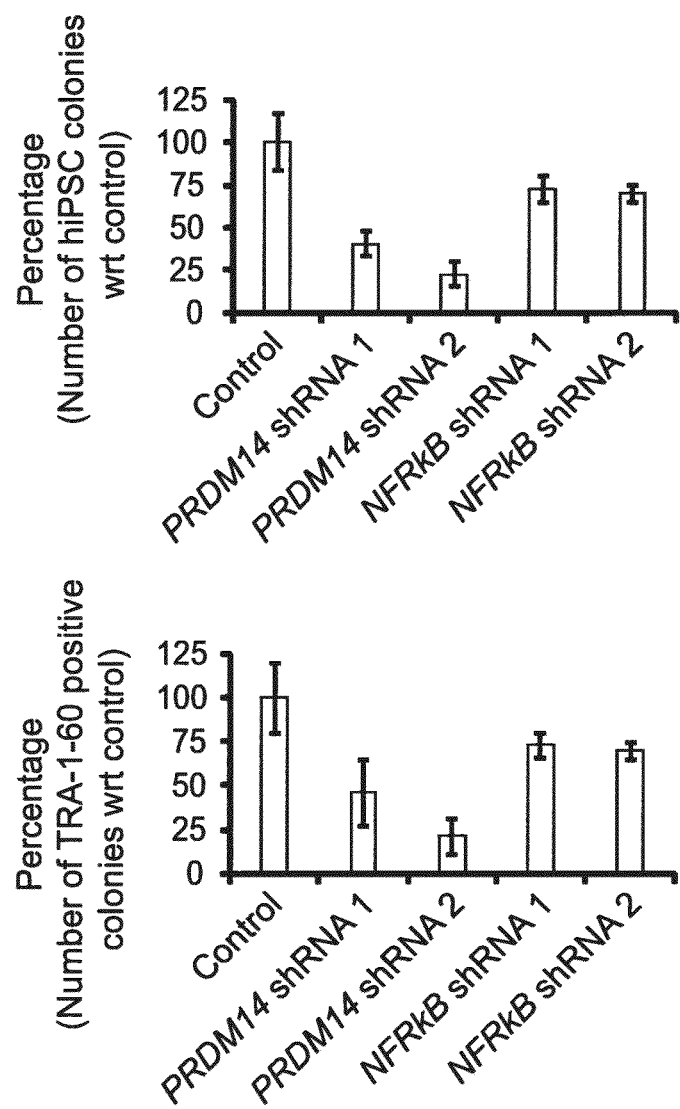

To further address the role of PRDM14 and NFRKB in reprogramming and inducing pluripotency, shRNAs targeting PRDM14 or NFRKB were introduced along with the OSKM retroviruses. Remarkably, knockdown of PRDM14 by different shRNA constructs reduced the number of hiPSC colonies formed, indicating that reprogramming of human somatic cells is dependent on PRDM14 (FIG. 7B). Knockdown of NFRKB had a weaker effect than PRDM14, but also resulted in a reduced number of hiPSC colonies, indicating a role for NFRKB in the reprogramming of human somatic cells (FIG. 7B).

Figure 7C:
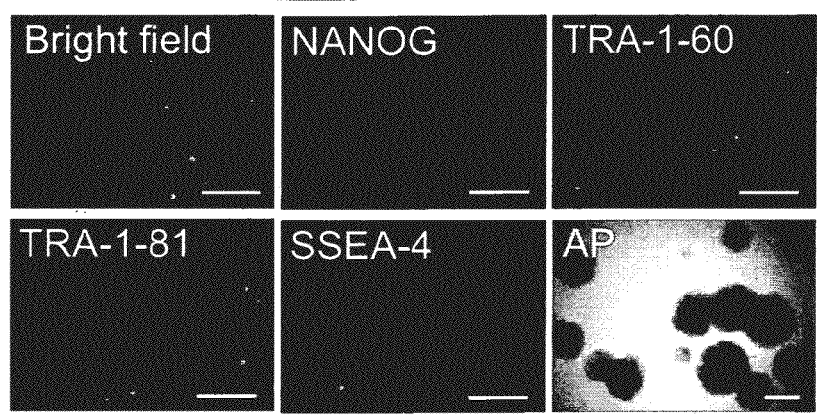
Figure 7C:
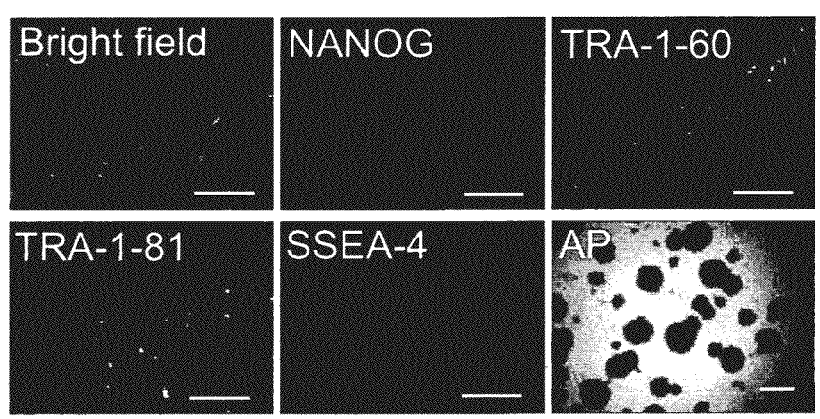
Figure 7C:
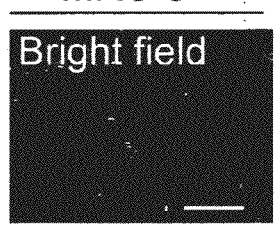
Figure 7D:
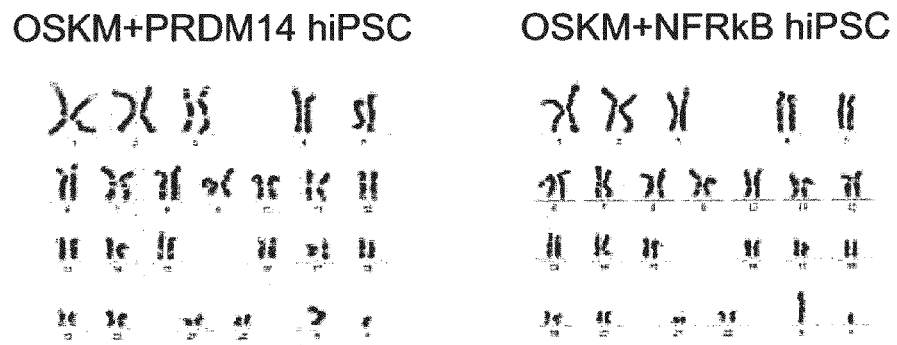
Figure 7E:
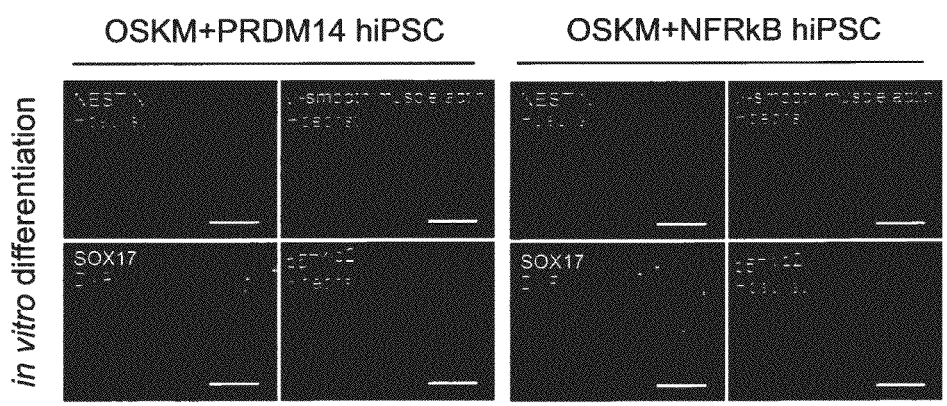
Figure 7F:
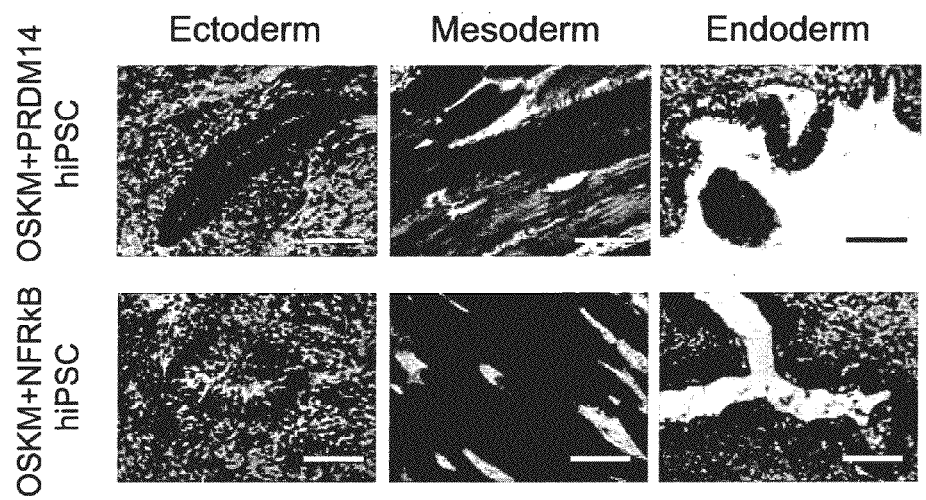
Figure 7G:
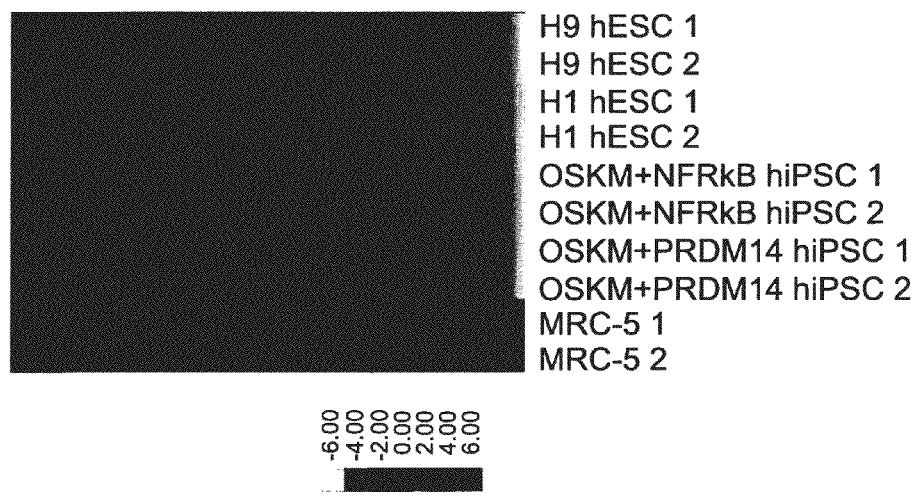
Figure 7H:
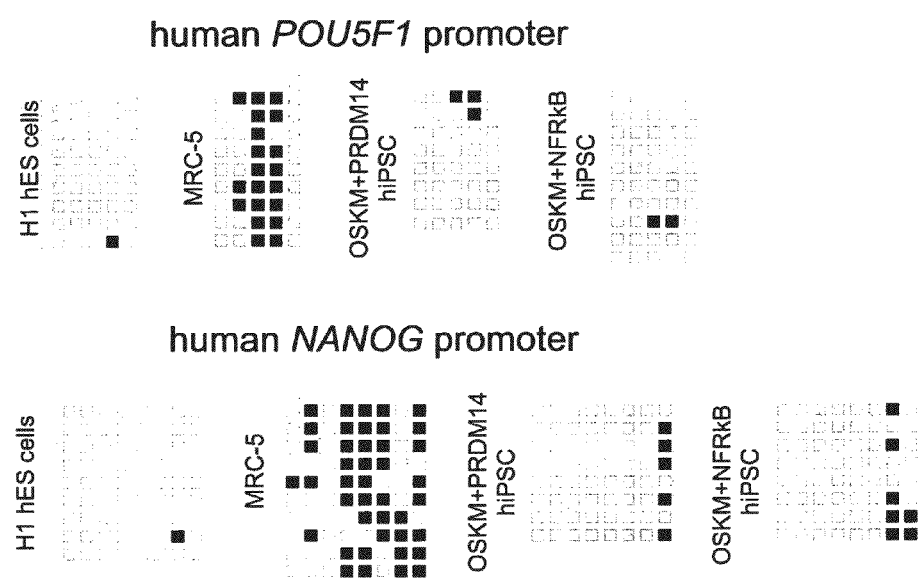

The OSKMP and OSKMN hiPSCs expressed pluripotency markers such as NANOG, TRA-1-60, TRA-1-81, SSEA-4 and alkaline phosphatase and showed normal karyotypes (FIGS. 7C and 7D). The hiPSCs are pluripotent as determined by in vitro differentiation and teratoma formation assays (FIGS. 7E and 7F). In addition, both OSKMP and OSKMN hiPSCs have a similar gene expression profile to the two hESCs lines, but not the fibroblasts (FIG. 7G) and they also showed loss of DNA methylation at the POU5F1 and NANOG promoters (FIG. 7H). The results indicate that PRDM14 and NFRKB can enhance reprogramming mediated by the OSKM combination of transcription factors. c-MYC is not necessary for reprogramming, but it can enhance the generation of iPSCs [47].

Figure 8A:
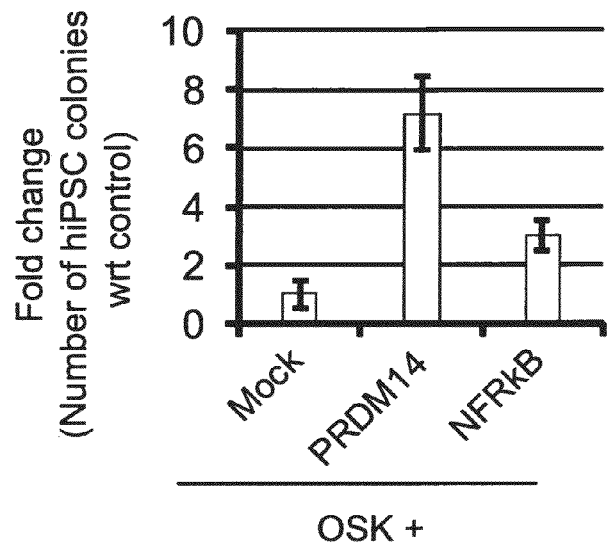
FIG. 8: Characterization of PRDM14 and NFRKB reprogrammed hiPSCs. (8A) PRDM14 and NFRKB can enhance reprogramming mediated by OCT4, SOX2 and KLF4. Graph depicts fold change of number of hESC-like iPSC colonies generated from PRDM14 or NFRKB in conjunction with OCT4, SOX2 and KLF4 (OSK) with respect to the control (OSK). Each column represents the average of 3 replicates. All values are means±s.e.m from 3 independent experiments (n=3). (8B) Both OSK+PRDM14 hiPSCs and OSK+NFRKB hiPSCs showed normal karyotype. (8C) Immuno-fluorescence staining showed the expression of hESC markers (NANOG, TRA-1-60, TRA-1-81 and SSEA-4) in hiPSCs induced by PRDM14 or NFRKB in the absence of c-MYC. These hiPSCs were also stained for alkaline phosphatase (AP). The scale bars represent 200 μm in bright field and IF images, and 2 mm in the AP staining image. (8D) In vitro differentiation of hiPSCs. Both OSK+PRDM14 hiPSCs and OSK+NFRKB hiPSCs can differentiate into different lineages via EB (embryoid body)-mediated or growth factor-induced in vitro differentiation. The hiPSCs can differentiate into ectodermal (indicated by NESTIN staining) and mesodermal cells (indicated by α-smooth muscle actin staining) using EB-mediated method. Definitive endodermal cells (as shown by staining for SOX17) derived with activin A induction and trophectodermal cells (as shown by staining for p57kip2) derived with combined BMP4 induction and FGF inhibition (PD0325901) were also obtained from these hiPSCs. The scale bars represent 200 μm. (8E) Teratoma formation assay for OSK+PRDM14 hiPSCs and OSK+NFRKB hiPSCs. Tissues derived from all three germ layers (ectoderm, mesoderm and endoderm) were obtained. Tissues shown correspond to pigmented epithelium, muscle, gut epithelium and kidney-like tissues. Bars represent 50 μm. (8F) Microarray profiling of hiPSCs. Heatmap showing the gene expression profile of 1,000 hESC-associated genes and fibroblast-associated genes in H1, H9 hESCs, two hiPSC lines and MRC-5. The selection of genes was based on the fold differences in their expression levels in hESCs and fibroblasts. The genes were sorted according to the average expression ratios and mean-centred around the fibroblasts signal. The greyscale bar indicates the gene expression normalized to fibroblasts in log 2 scale. (8G) DNA methylation analysis of hiPSCs. POU5F1 and NANOG promoter regions in H1 hESCs, MRC-5, PRDM14 or NFRKB-induced hiPSCs (in the absence of c-MYC) were analyzed by bisulfite sequencing. Each row of squares represents an individual sequencing result. Grey squares represent unmethylated CpG dinucleotides; black squares represent methylated CpG dinucleotides. (8H) PRDM14 and NFRKB can replace KLF4 to induce hiPSC in conjunction with OCT4, SOX2 and c-MYC. Immunofluorescence staining showed the expression of hESC markers (NANOG, TRA-1-60, TRA-1-81 and SSEA-4) in hiPSCs induced by PRDM14 or NFRKB in the absence of KLF4. These hiPSCs were also stained for alkaline phosphatase (AP). The scale bars represent 200 μm in bright field and IF images, and 2 mm in the AP staining image. (8I) Both OSC+ PRDM14 hiPSCs and OSC+NFRKB hiPSCs can differentiate into different lineages via EB (embryoid body)-mediated or growth factor-induced in vitro differentiation. The hiPSCs can differentiate into ectodermal (indicated by NESTIN staining) and mesodermal cells (indicated by α-smooth muscle actin staining) using EB-mediated method. Definitive endodermal cells (as shown by staining for SOX17) derived with activin A induction and trophectodermal cells (as shown by staining for p57kip2) derived with combined BMP4 induction and FGF inhibition (PD0325901) were also obtained from these hiPSCs. The scale bars represent 200 μm.
Figure 8B:
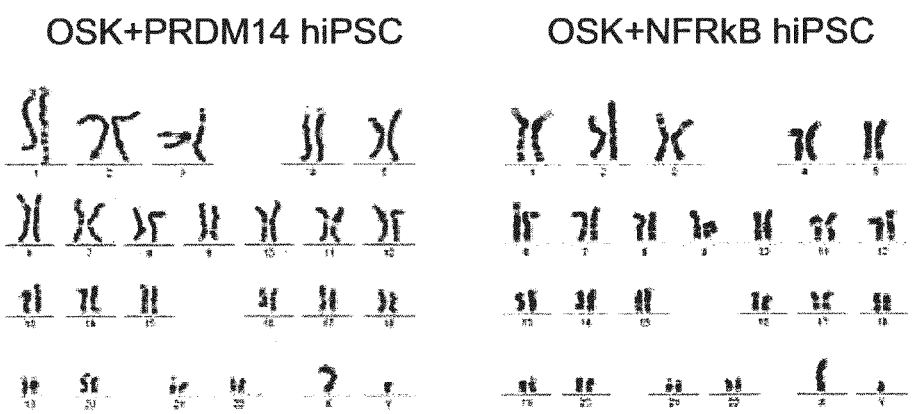
Figure 8C:
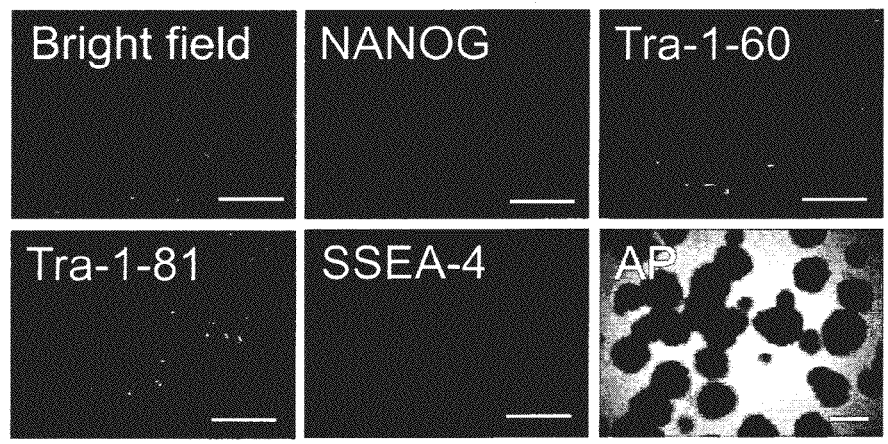
Figure 8C:
Figure 8D:
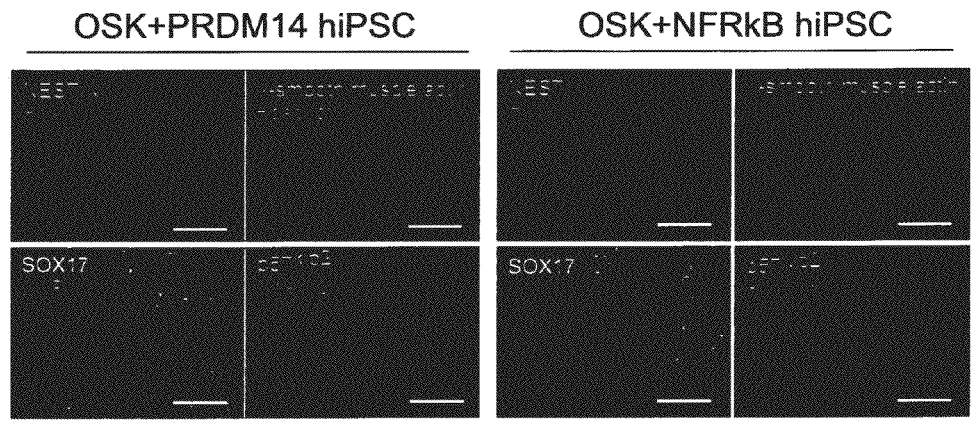
Figure 8E:
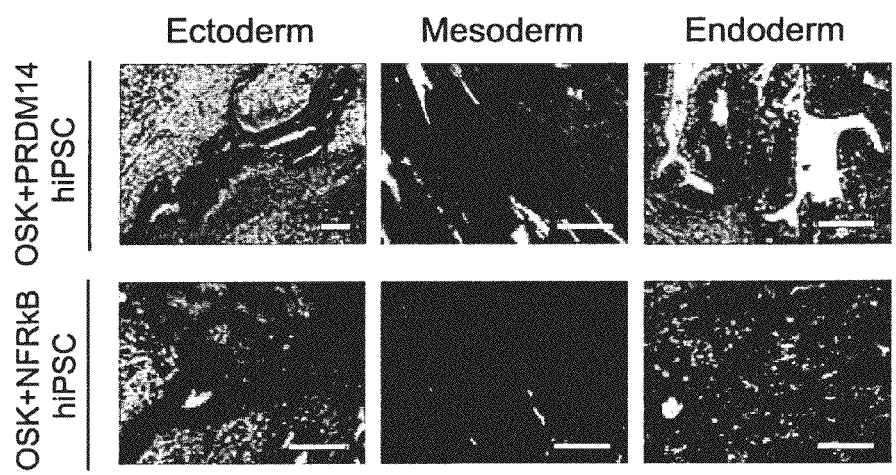
Figure 8F:
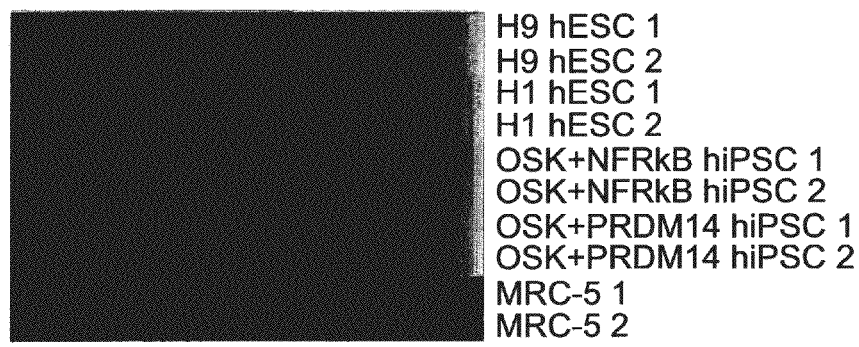
Figure 8G:
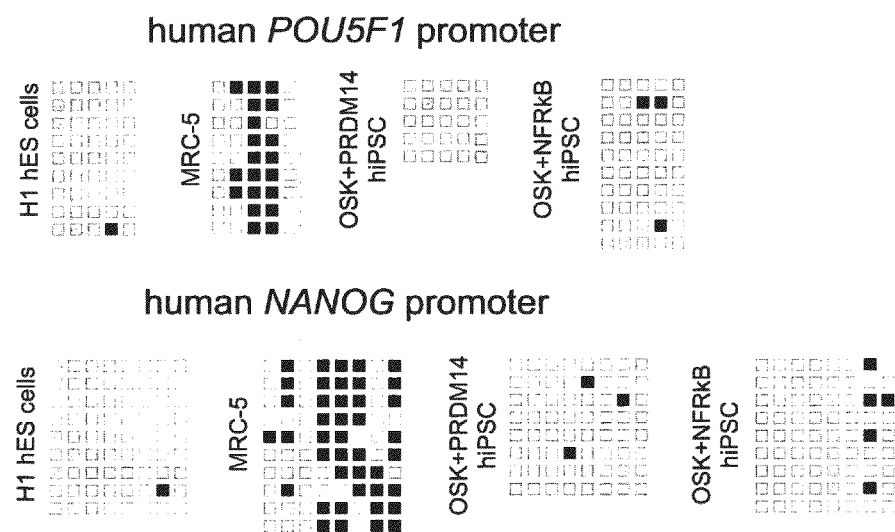

Next, it was tested whether PRDM14 and NFRKB can affect reprogramming efficiency mediated by OSK. In the absence of c-MYC (OSK transduction), only a few hiPSC colonies were recovered. However, OSKP reprogramming resulted in 7 fold more colonies than in the absence of PRDM14 (FIG. 8A). NFRKB was able to enhance reprogramming by 3 fold (FIG. 8A). The OSKP and OSKN hiPSCs are also karyotypically normal, expressed hESC markers, and are pluripotent as shown by in vitro and in vivo differentiation (FIGS. 8B-8E). These hiPSCs also showed hESC-specific gene expression pattern and loss of DNA methylation at the POU5F1 and NANOG promoters (FIGS. 8F and 8G). Hence, PRDM14 and NFRKB are able to substitute for c-MYC.

Figure 8H:
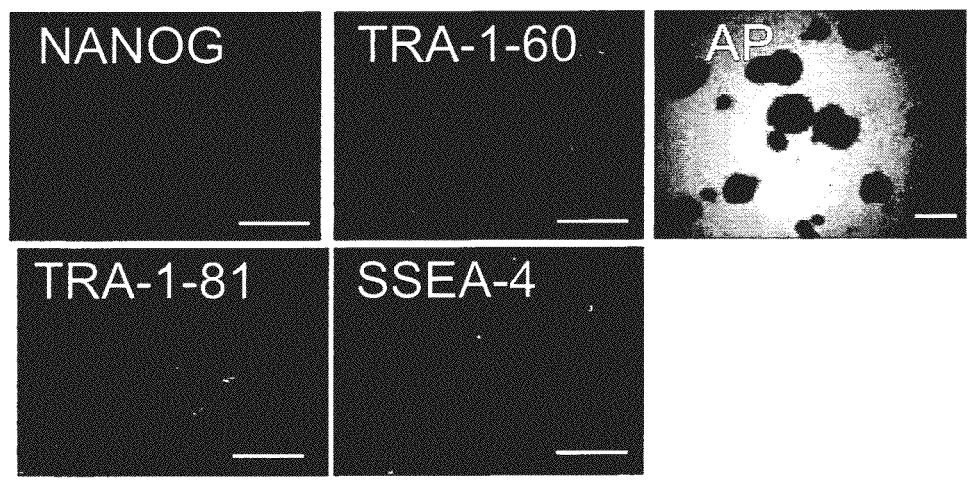
Figure 8H:
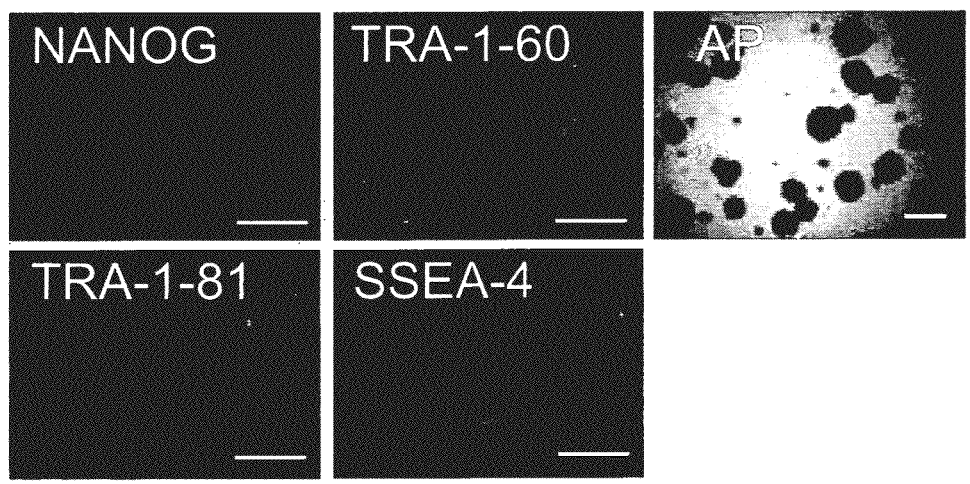
Figure 8I:
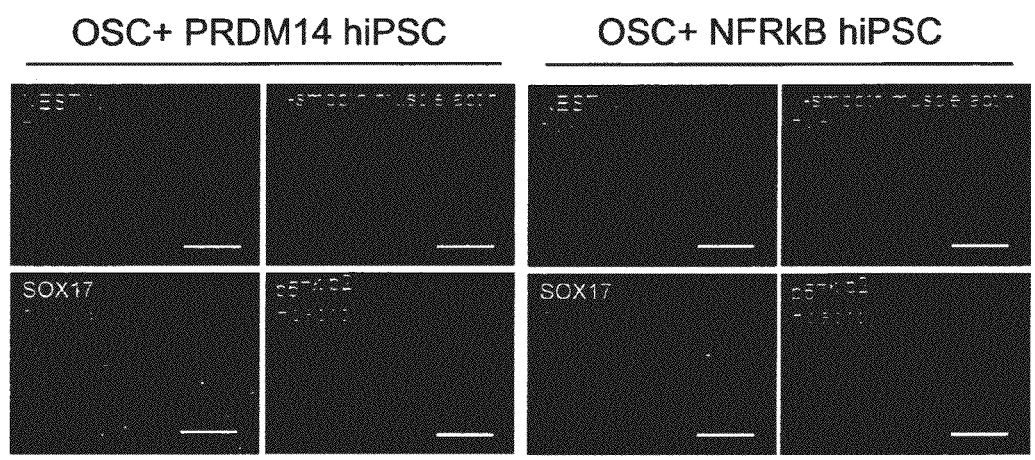

Interestingly, it was also found that PRDM14 and NFRKB can replace KLF4 since it was possible to generate hiPSCs using OSCP and OSCN (FIGS. 8H and 8I). However, in the absence of OCT4 or SOX2, no hiPSCs were obtained.

Taken together, these results demonstrate that PRDM14 and NFRKB have important functions in the acquisition of pluripotency in human cells.

PDRM14 is Important for hESC Pluripotency:

Although the genome-wide RNAi screen was effective in uncovering novel genes that are important in the maintenance of hESCs and reprogramming, their mechanisms of action remain elusive. Therefore, a candidate gene was selected for further study in order to gain new insights into its link with pluripotency in hESCs.

Depletion of PRDM14 by the pooled siRNAs resulted in a significant GFP reduction with a z-score of 3.79 (ranked $10^{th}$ in the primary screen) and it was validated in the secondary screen. Furthermore, PRDM14 is highly expressed in a variety of hESCs [48] and is a target of the core transcription factors in hESCs [8].

Therefore, to further characterize PDRM14 and to further elucidate its role in maintaining hESCs, knockdown of PDRM14 with the 4 shRNA constructs was performed in non-reporter hESCs and their loss of pluripotency was examined.

Figure 9A:
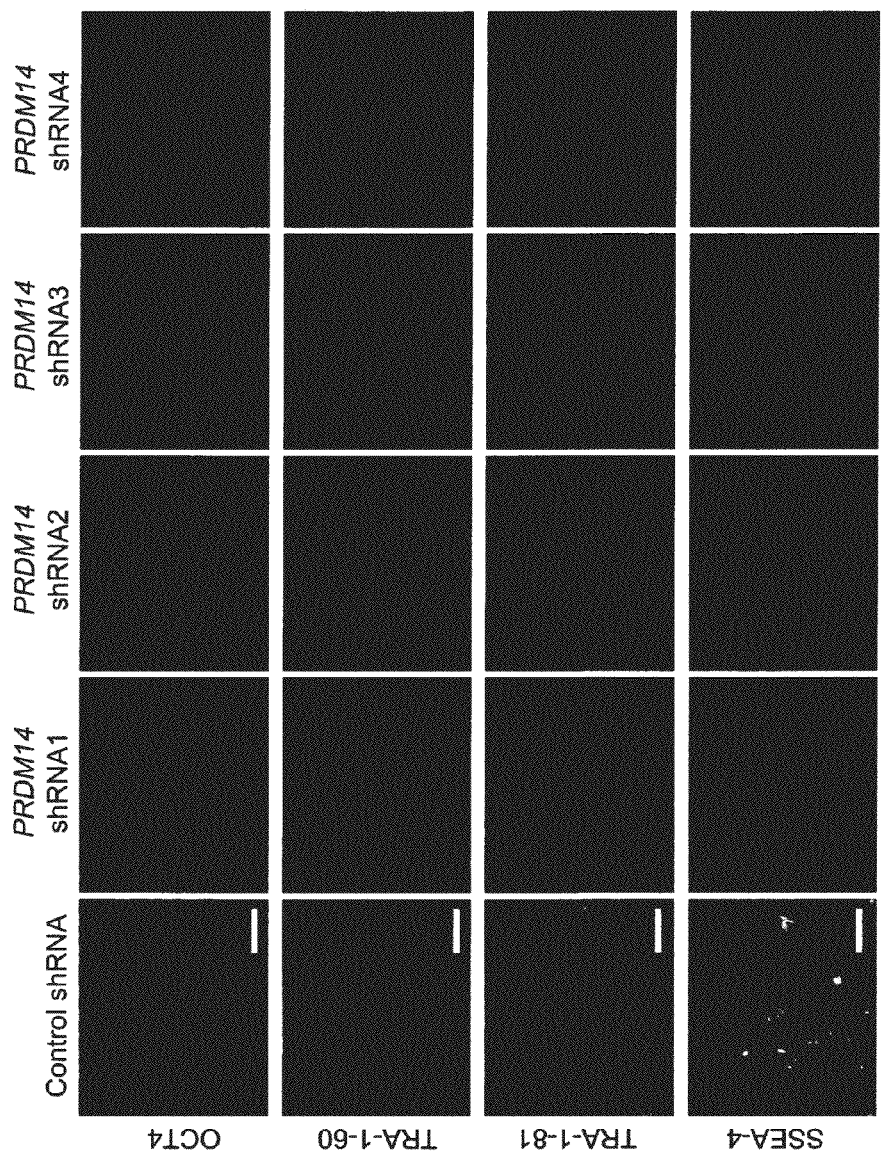
FIG. 9: PRDM14 and the maintenance of H1 hESCs. (9A) Immunofluorescence staining for stemness markers. PRDM14 and control knockdown H1 hESCs were stained for OCT4, TRA-1-60 and TRA-1-81 after 4 days of knocked down. The nuclei of the cells were counterstained with Hoechst. Scale bars represent 50 μm. (9B) Analysis of PRDM14, OCT4 and NANOG protein levels by western blot. (9C) Quantification of pluripotency-related transcript levels. Pluripotency-associated genes SOX2, HELLS and DPPA4 were quantified for mRNA expression changes by qPCR. All values are means±s.e.m from 3 independent experiments (n=3) and fold changes were normalized against control luciferase RNAi samples. (9D) Quantification of differentiation-related transcript and protein levels. RUNX1, MAFB and IGFBP5 were quantified for mRNA expression changes by qPCR. All values are means±s.e.m from 3 independent experiments (n=3) and fold changes were normalized to control RNAi samples. Immunofluorescence assays were used to detect protein expression upon PRDM14 depletion. Scale bars represent 100 μm.
Figure 9B:
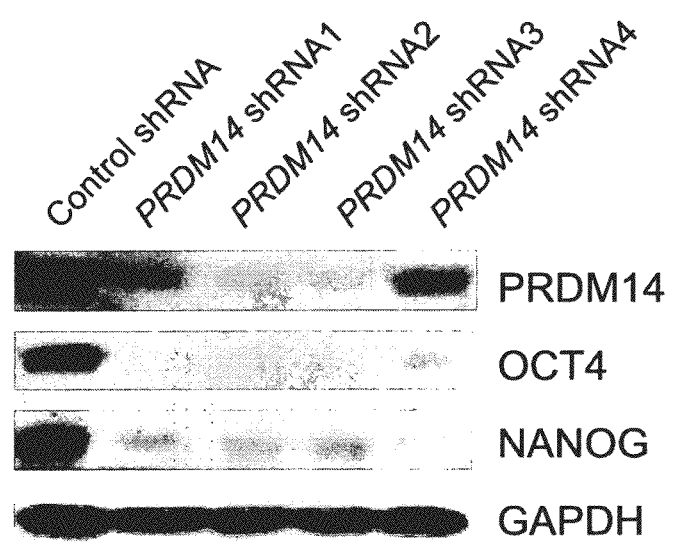
Figure 9C:
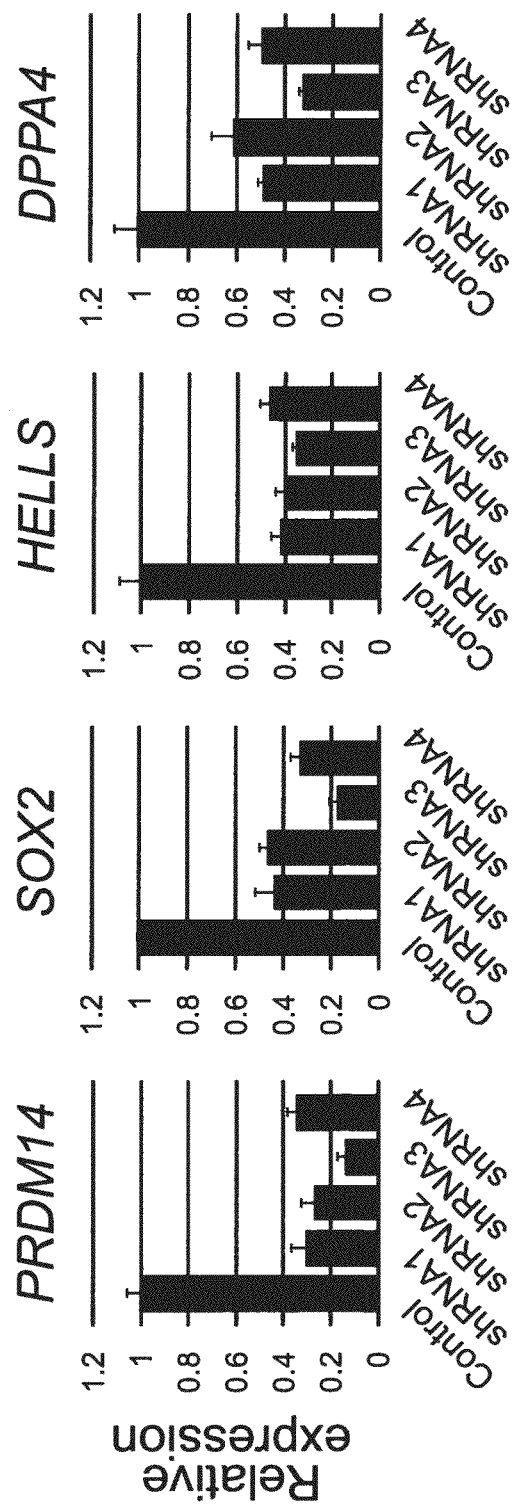
Figure 9D:
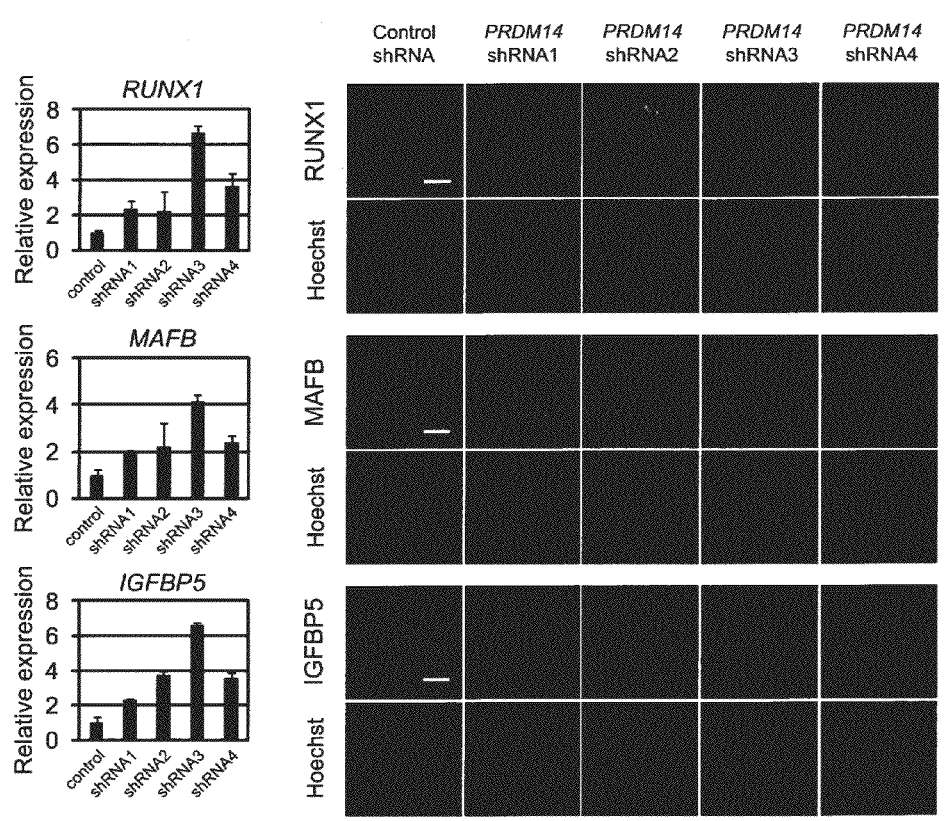
Figure 10A:
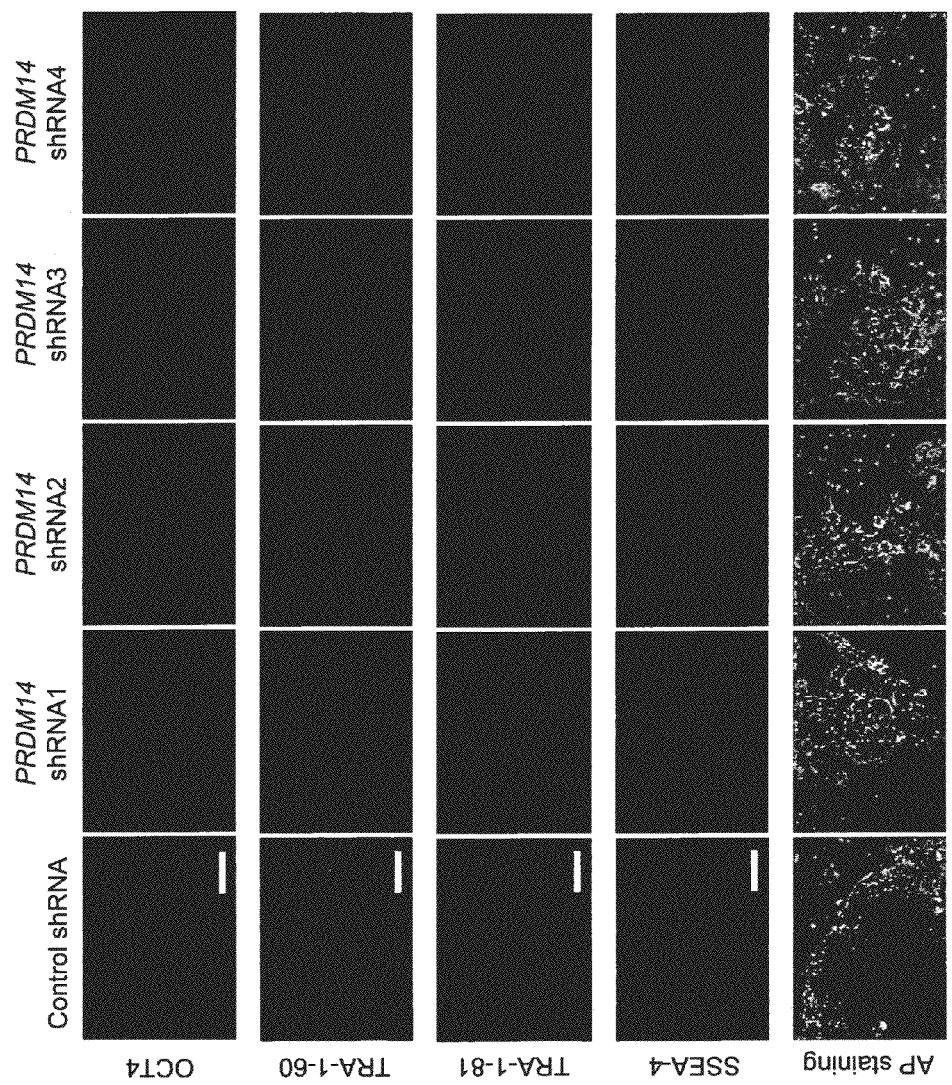
FIG. 10: Validation for PRDM14 knockdown in HES3 hESCs. (10A) PRDM14 and control knockdown HES3 hESCs were stained for hESC markers (OCT4, TRA-1-60, TRA-1-81 and SSEA-4) and alkaline phosphatase after 4 days of knockdown. The nuclei of the cells were counterstained with Hoechst. Scale bars represent 50 μm. (10B) Quantification for pluripotency-related transcript levels.
Figure 10B:
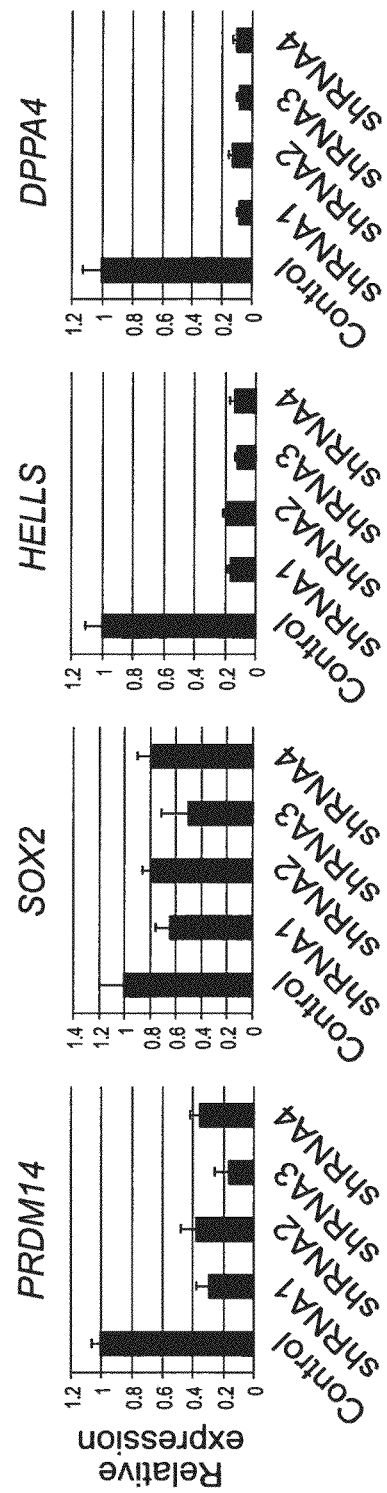
Figure 11A:
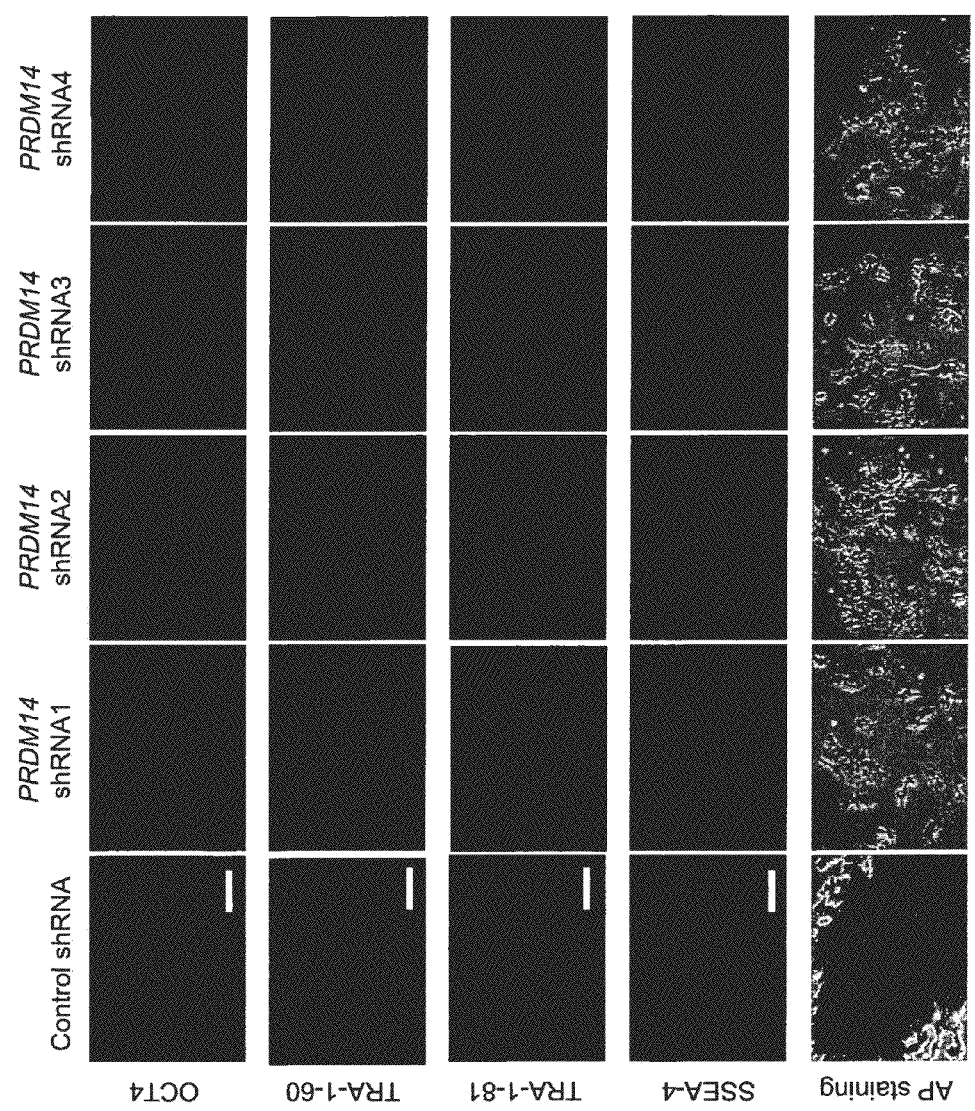
FIG. 11: Validation for PRDM14 for PRDM14 Knockdown in H9 hESCs. (11A) PRDM14 and control knockdown H9 hESCs were stained for hESC markers (OCT4, TRA-1-60, TRA-1-81 and SSEA-4) and alkaline phosphatase after 4 days of knockdown. The nuclei of the cells were counterstained with Hoechst. Scale bars represent 50 μm. (11B) Quantification for pluripotency-related transcript levels.
Figure 11B:
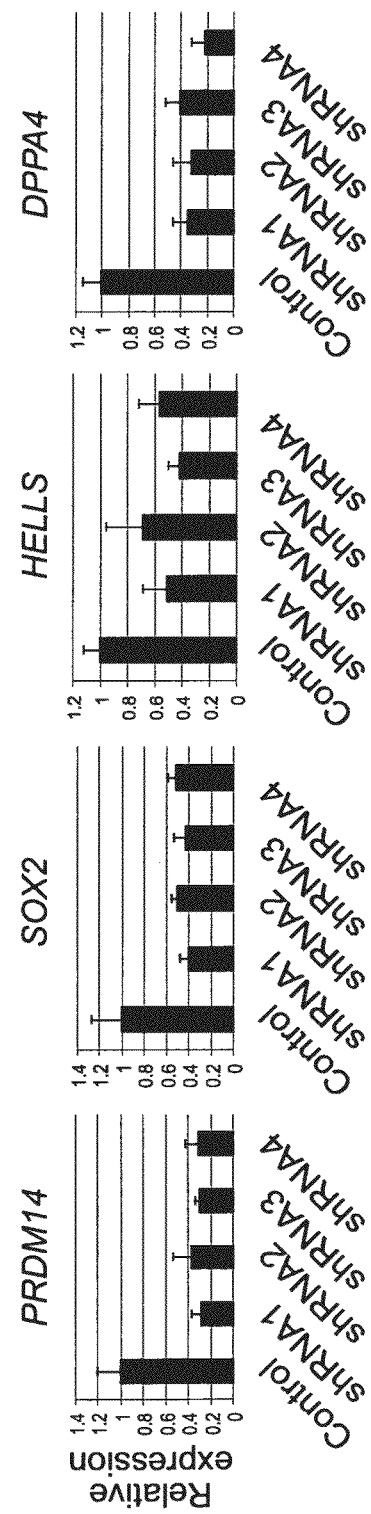

Depletion of PRDM14 resulted in a reduction in the expression of stemness markers like OCT4, TRA-1-60, TRA-1-81 and SSEA-4 in 3 different hESC lines (H1, H9 and HES3) as determined by immunofluorescence staining (FIGS. 9A, 10A and 11A). Western blot analysis also showed a downregulation of OCT4 and NANOG with PRDM14 depletion (FIG. 9B). In addition, the expression of other hESC-associated genes such as SOX2, HELLS and DPPA4 was also down-regulated (FIGS. 9C, 10B and 11B). On the other hand, proteins that are expressed in differentiated cell-types (RUNX1, MAFB and IGFBP5) were up-regulated upon PRDM14 depletion (FIG. 9D), indicating differentiation of the hESCs.

In mice, Prdm14 is highly expressed in the primordial germ cells (PGCs) and is essential for the establishment of the germ cell lineage [52]. Prdm14 is not essential for early embryonic development as the knockout mice were born with an expected Mendelian ratio.

Figure 12A:
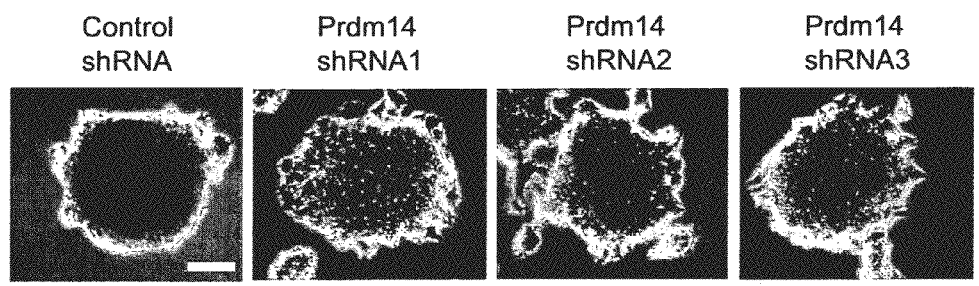
FIG. 12: Prdm14 is not required for the maintenance of mouse ESCs and is deficient in mouse EpiSCs. (12A) Knockdown of Prdm14 in mESCs with 3 different shRNA constructs did not induce differentiation as indicated by the alkaline phosphatase staining and morphology. Scale bar represents 50 uM. (12B) Knockdown of Prdm14 in mESCs does not reduce Oct4, Nanog and Sox2 expression. All qPCR values are means±s.e.m from 3 independent experiments (n=3) and fold changes were normalized to control RNAi samples. (12C) Genes expressed at high and low level in EpiSCs. All qPCR values are means±s.e.m from 3 independent experiments (n=3) and fold changes were normalized to Gapdh. (12D) Prdm14 is expressed at a very low level as compared to mouse ESC. All qPCR values are means s.e.m from 3 independent experiments (n=3) and fold changes were normalized to mouse ESC sample.
Figure 12B:
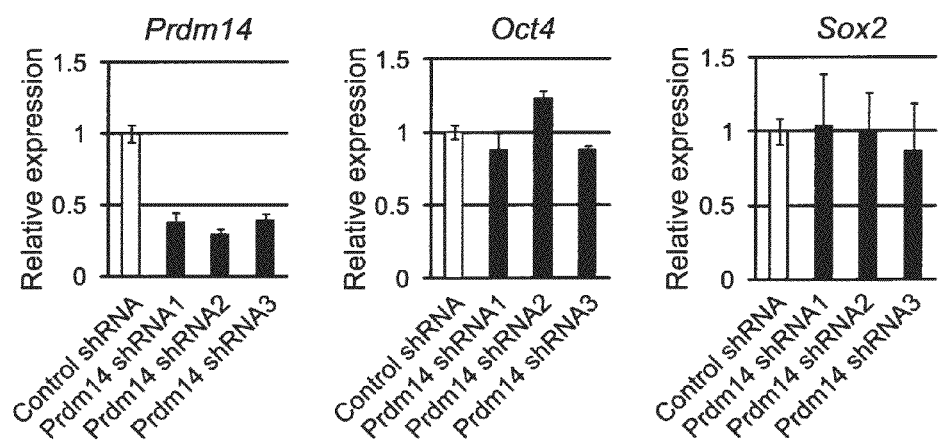
Figure 12C:
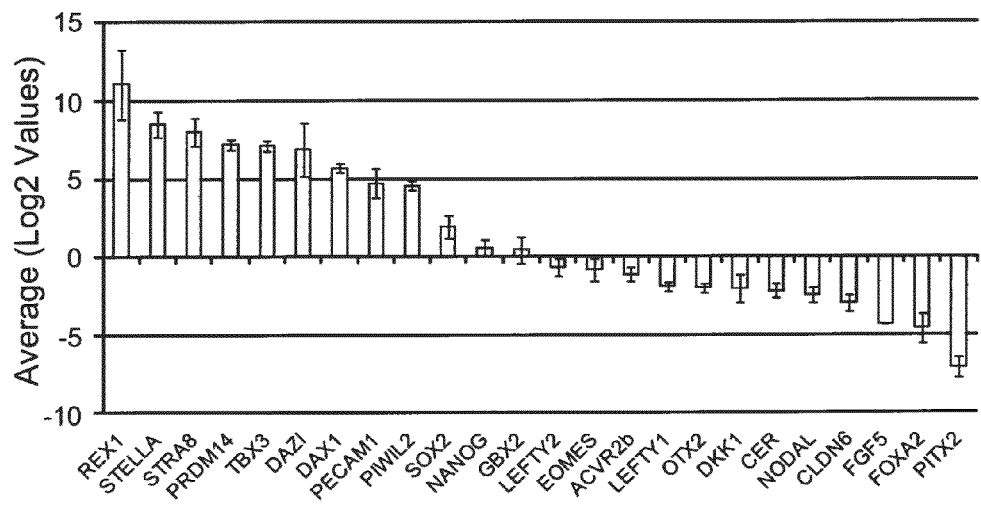
Figure 12D:
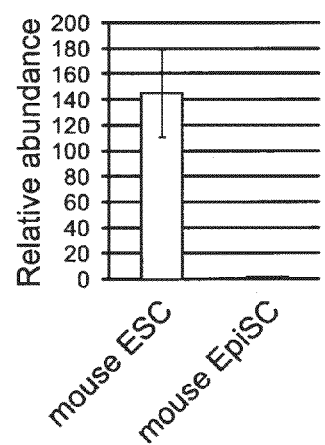

Here, the inventors have knocked down Prdm14 in mouse ESC and have found no observable phenotypic change and no significant reduction in OCT4 and SOX2 (FIGS. 12A and 12B). This result is consistent with the in vivo phenotype of Prdm14 null embryos. As mouse epiblast-derived stem cells (EpiSCs) are also pluripotent and exhibit characteristics of hESCs [21, 22], the present inventors also examined and compared Prdm14 levels against that of other genes that are characteristic of mouse EpiSCs. Surprisingly, it was found that Prdm14 is deficient in mouse EpiSCs (FIGS. 12C and 12D). Thus, Prdm14 is differentially regulated in mouse EpiSCs and may only be required for the maintenance of hESCs.

Example 3

PRDM14 Regulates the Proximal Enhancer of POU5F1

Figure 13A:
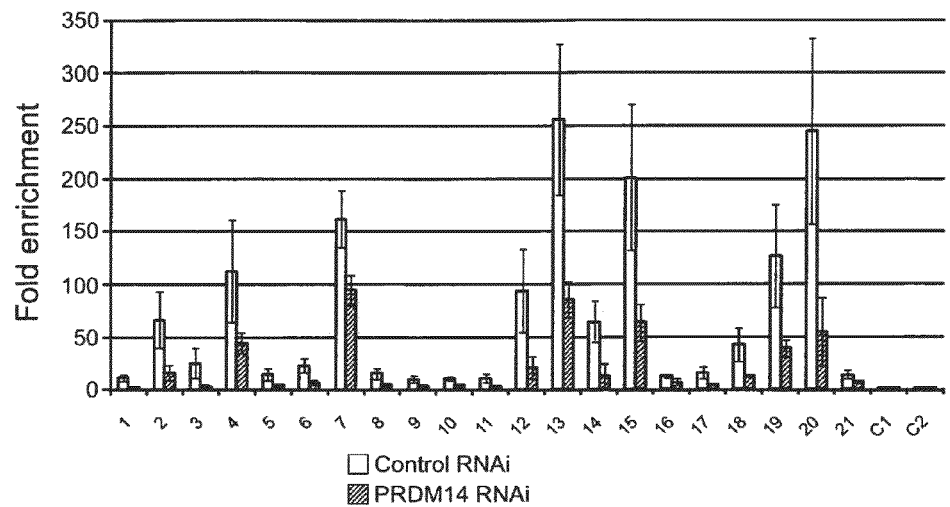
FIG. 13: Validation of PRDM14 ChIP-seq dataset. (13A) H1 hESCs were transfected with the PRDM14 or control knockdown construct and harvested 72 hrs post transfection. 21 genomic loci bound by PRDM14 from the ChIP-seq analysis were chosen for validation. C1 and C2 are control regions showing only background level of enrichment. (13B) H1 hESCs were transfected with the HA-tagged PRDM14 expression construct and harvested 72 hrs post transfection. An antibody specific for the HA tag was used in the ChIP against chromatin extracts from cells transfected with the PRDM14 expression construct and untransfected cells. C1 and C2 are control regions showing only background level of enrichment.
Figure 13B:
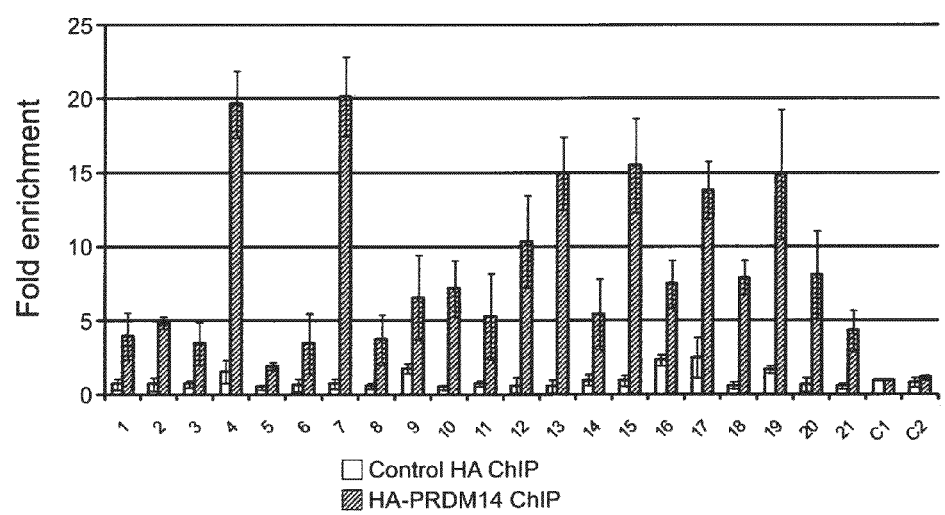

To further investigate the function of PRDM14, chromatin immunoprecipitation coupled with massively parallel short-tag-based sequencing (ChIP-seq) was used to map the in vivo binding loci using our PRDM14 antibody (data not shown). The specificity of the PRDM14 ChIP-seq data was validated with two different assays. First, PRDM14 ChIP was performed on PRDM14-depleted hESCs and a reduction of ChIP signals at 21 randomly chosen binding sites was observed (FIG. 13A). Second, HA ChIP was performed on hESCs that expressed HA-tagged PRDM14 and an enrichment at the same 21 sites was obtained (FIG. 13B). Both assays confirmed that PRDM14 is bound to the tested sites.

Figure 14A:
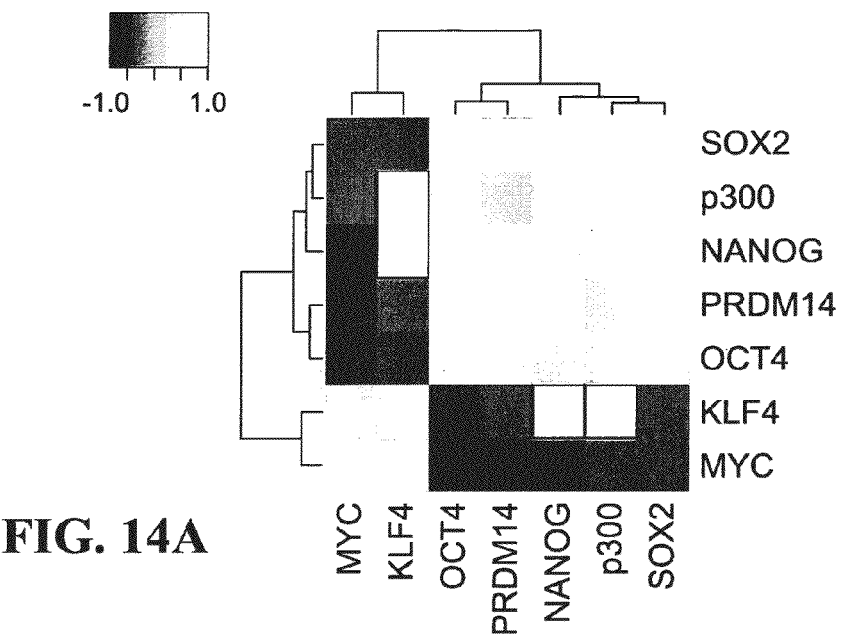
FIG. 14: PRDM14 regulates POU5F1 enhancer. (14A) PRDM14 shows co-binding with OCT4, SOX2, NANOG and co-activator p300. Greyscale intensity in the heat map reflects the co-localization frequency of each of the transcription factors (the descending frequency of localization ranges from white to grey to dark grey). (14B) PRDM14 motif predicted by the de novo motif-discovery algorithm CisFinder. (14C) ChIP-seq binding profile of PRDM14, OCT4, NANOG, CTCF at POU5F1 locus. Control ChIP-seq library was obtained from sequencing of input DNA. (14D) PRDM14 binds to CR2 probe. Probe containing putative PRDM14 motif were incubated with purified recombinant PRDM14 DNA binding domain (DBD) protein. Introduction of mutations in the putative motif disrupt the PRDM14 DBD/DNA complex. (14E) Native PRDM14 binds to CR2 probe. Probes containing putative PRDM14 motif were incubated with nuclear extract prepared from hESCs. Introduction of mutations in the putative motif disrupt the PRDM14 DBD/DNA complex. Supershift assay was performed by adding PRDM14 antibodies to the EMSA sample. (14F) PRDM14 regulates CR2 enhancer but not CR4 enhancer in hESC. CR2 and CR4 of the POU5F1 upstream regulatory region were each cloned downstream of the luciferase reporter gene driven by a POU5F1 proximal promoter (~350 bp). Each of the constructs was transfected into H1 hESCs to test for enhancer activity. PRDM14 shRNA construct was co-transfected with the reporter construct and activity was normalized against the knockdown control. All values are means±s.e.m from 3 independent experiments (n=3). (14G) PRDM14 is bound to CR2 but not CR4 region. ChIP assay was performed using a PRDM14 antibody. (14H) NANOG binds to PRDM14 in human ES cells. Co-IP using hESC whole cell lysate with anti-Nanog antibody. Western was carried out with PRDM14 antibody. Control IgG antibody was used in the control IP. (14I, 14J) NANOG binds to PRDM14 in 293 cells. 293T cells were co-transfected with cDNAs encoding HA tagged PRDM14 and NANOG protein. Whole cell lysate was used for co-IP with anti-HA and anti-Nanog antibody.

Next, an examination of the co-occupancy of PRDM14 with other transcription factors mapped by the inventors and other laboratories was examined. The inventors had previously shown that Oct4, Sox2 and Nanog co-localize with the co-activator p300 in a cluster distinct from the c-Myc containing cluster in mESCs [9]. Interestingly, the present co-occupancy analysis revealed that PRDM14 co-localizes with OCT4, SOX2, NANOG and p300 as well (FIG. 14A). Co-motif analysis of the PRDM14 binding loci revealed a significant enrichment of a joint Sox2-Oct4 motif, confirming the co-occurrence of PRDM14, OCT4 and SOX2 sites (FIG. 15). This indicates that PRDM14 is integrated into the core hESC transcriptional regulatory circuitry.

Figure 14B:
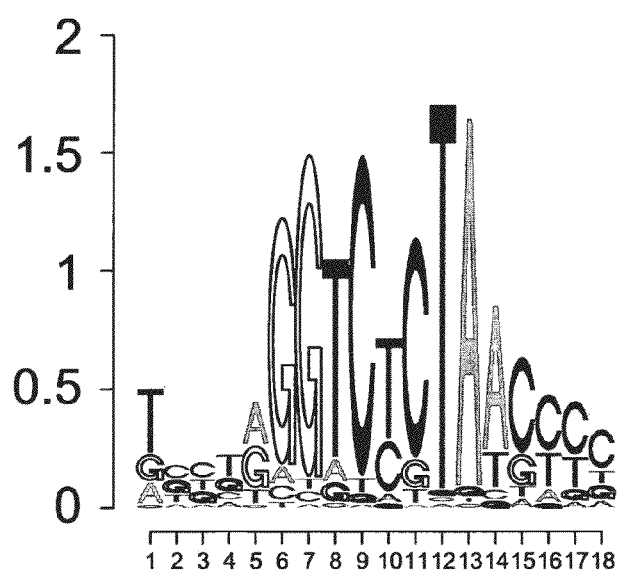

The PRDM14 protein has a putative DNA binding domain at the carboxyl-terminus. However, the DNA binding specificity of its C2H2 zinc finger is unknown. To determine the in vivo sequence specificity of PRDM14, the consensus sequence motifs were derived by using the de novo motif-discovery algorithm, CisFinder [53]. Interestingly, a motif that does not resemble any known motifs in the TRANSFAC, JASPAR or UniPROBE databases was discovered (FIG. 14B). Hence, the bona fide PRDM14 binding sites were identified through ChIP-seq analysis.

Figure 14C:
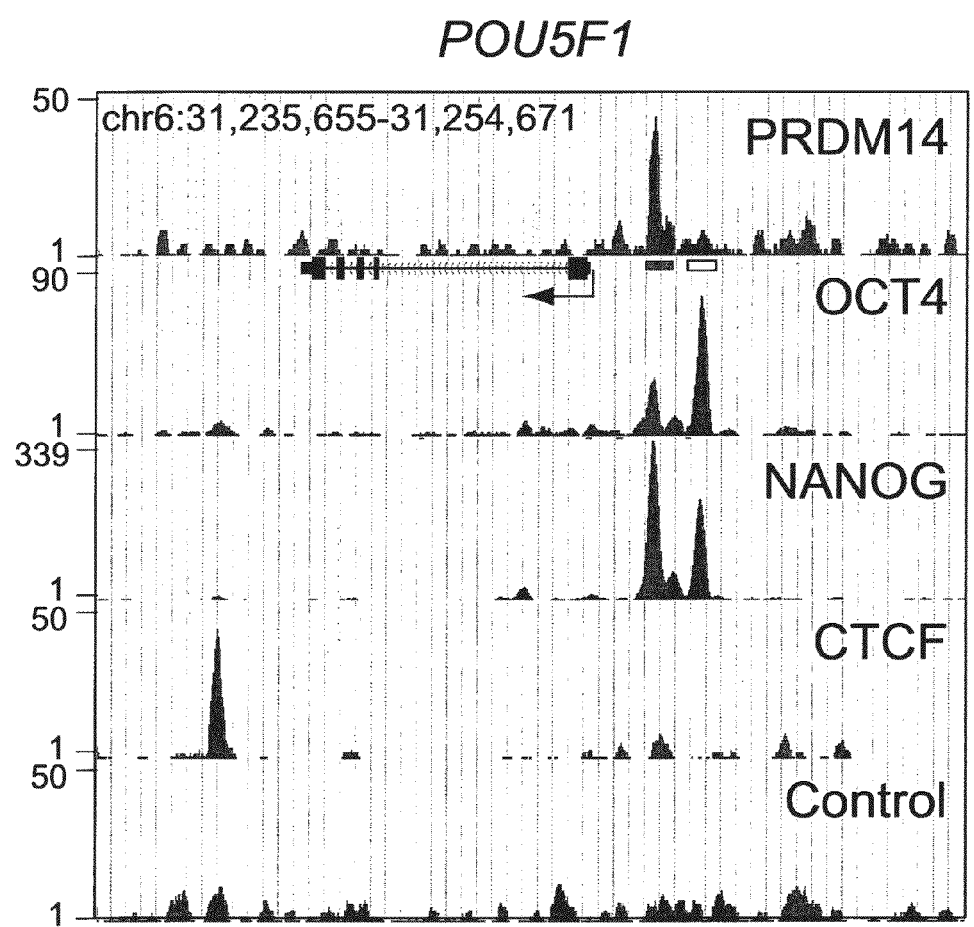
Figure 14D:
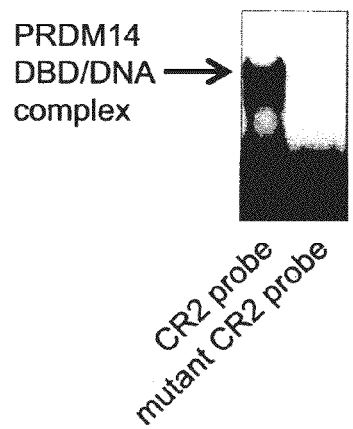
Figure 14E:
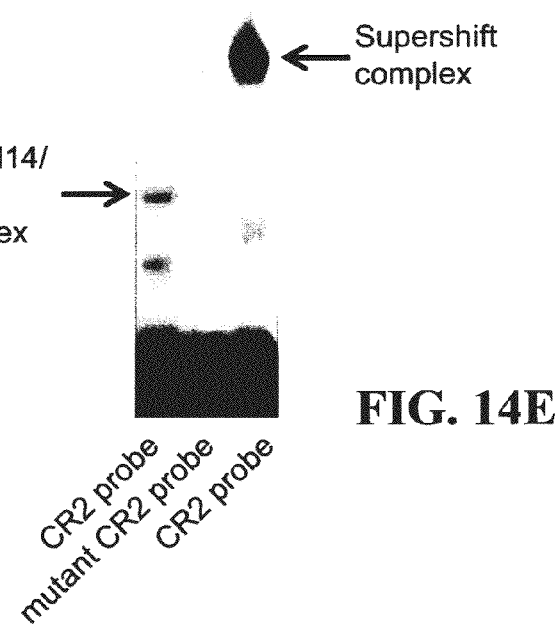

The ChIP-seq analysis identified 2,755 genes that were bound by PRDM14 (data not shown). Interestingly, a PRDM14 peak was observed at the POU5F1 upstream regulatory region (FIG. 14C). This region is known to contain a proximal enhancer and a distal enhancer [54-56]. There is differential usage of these enhancers in vivo. The distal enhancer, containing a conserved region 4 (CR4), activates Pou5f1 expression in pre-implantation embryos and in primordial germ cells but not in cells of the epiblast [56]. On the other hand, the proximal enhancer containing a conserved region 2 (CR2) is responsible for epiblast-specific Pou5f1 expression in vivo. Using EMSA, it was here confirmed that the CR2 sequence, which contains the PRDM14 motif, is indeed bound directly by recombinant PRDM14 protein (FIG. 14D) and native PRDM14 protein (FIG. 14E).

Figure 14F:
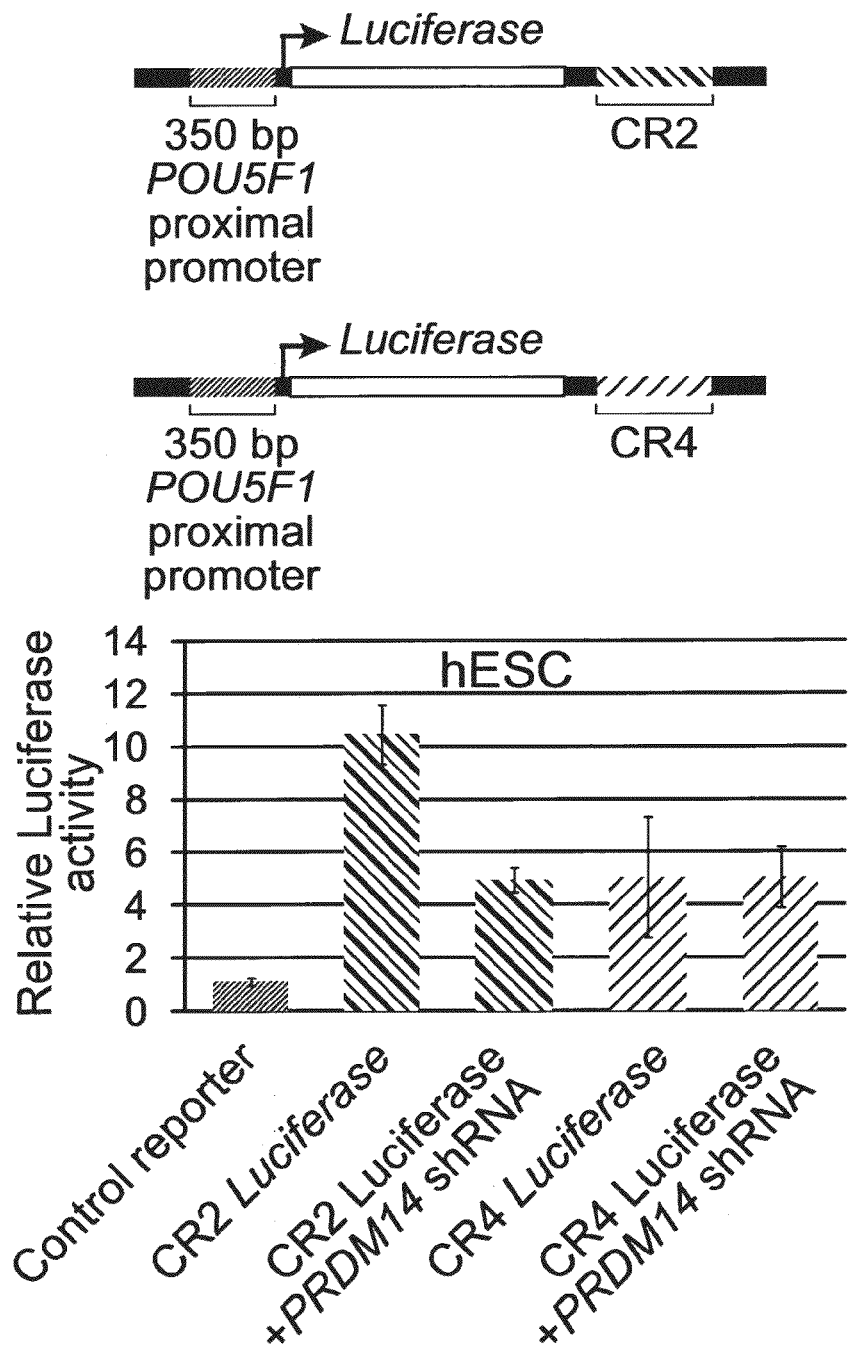
Figure 14G:
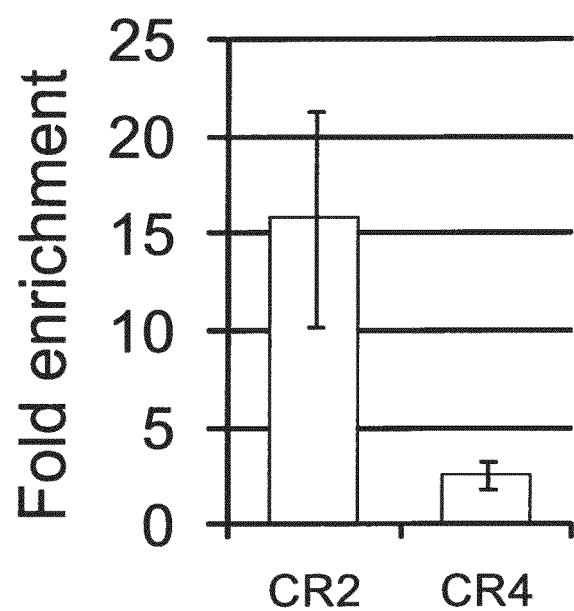
Figure 16A:
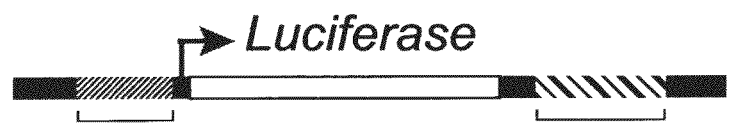
Figure 16A:
Figure 16B:
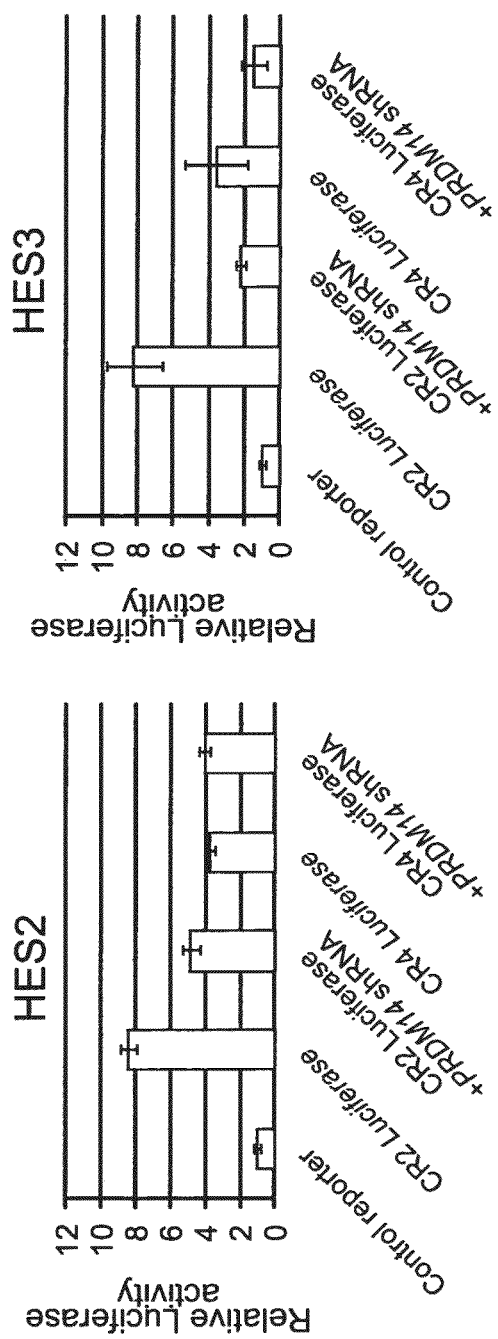
Figure 16C:
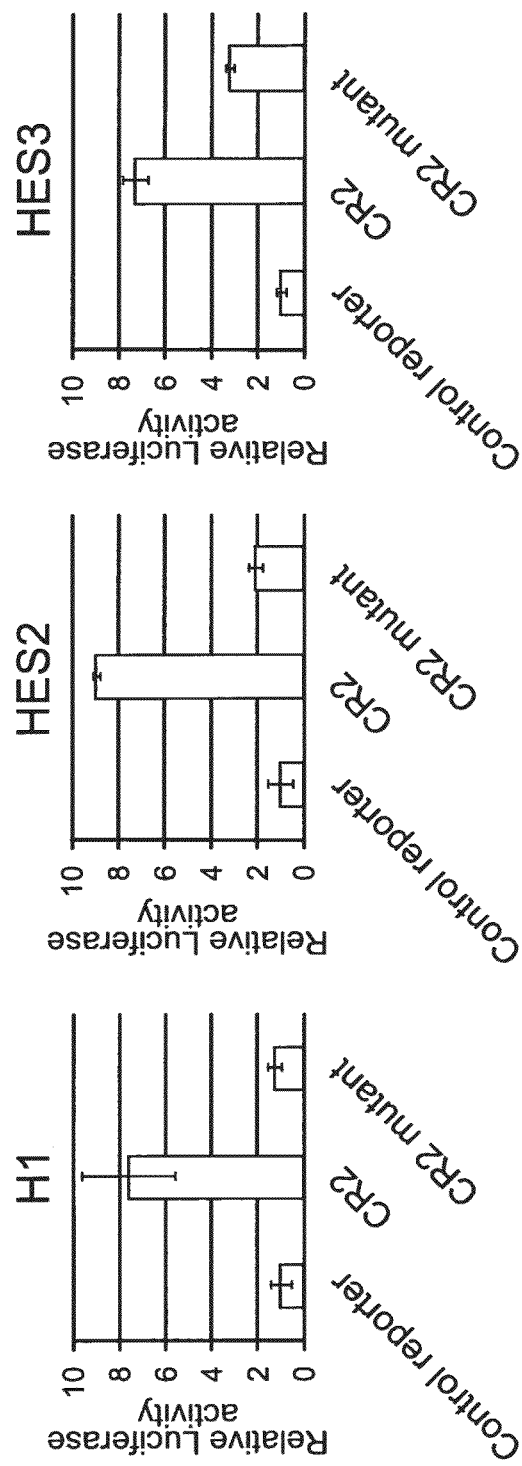

Next, the relative activity of the two CRs that were cloned downstream of a luciferase reporter and transfected into hESCs was assessed. Similar to the differential activity of the proximal and distal enhancers in mouse EpiSCs, the CR2 reporter was found to be more active than the CR4 reporter in hESCs (FIG. 14F) [22, 54]. Depletion of PRDM14 led to a downregulation of CR2 enhancer activity (FIG. 14F; FIGS. 16A and 16B). Mutation of PRDM14 site at CR2 could also reduce its activity (FIG. 16C). Using ChIP assay, it was confirmed that PRDM14 binds to CR2 but not CR4 (FIG. 14G). These data indicate that PRDM14 is regulating CR2 but not CR4 activity.

Figure 17A:
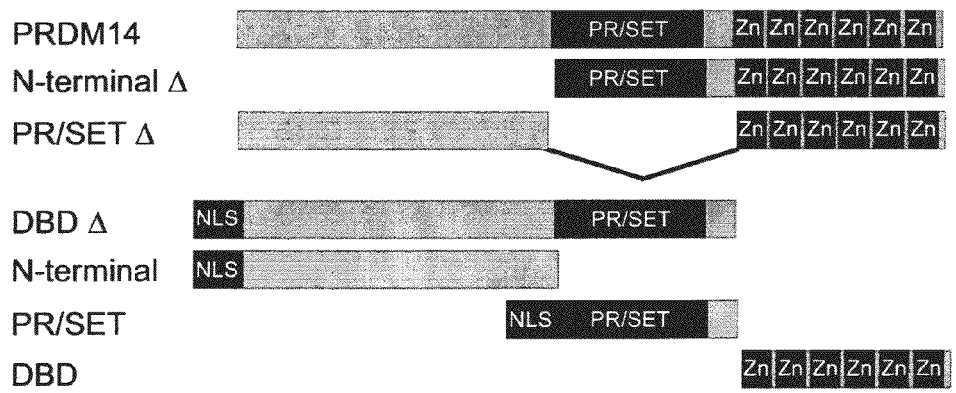
Figure 17B:
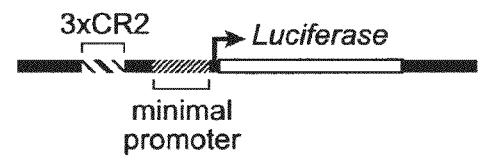
Figure 17B:
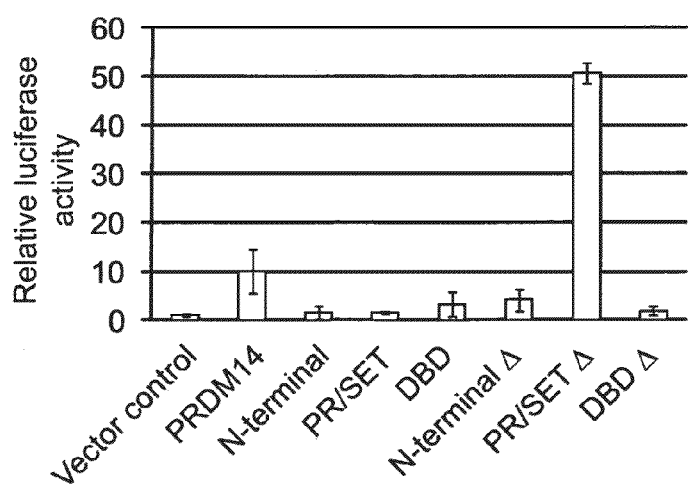
Figure 17C:
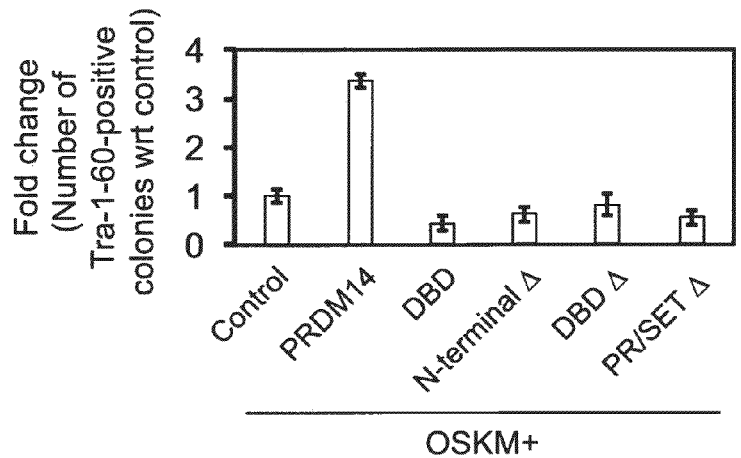
Figure 17D:
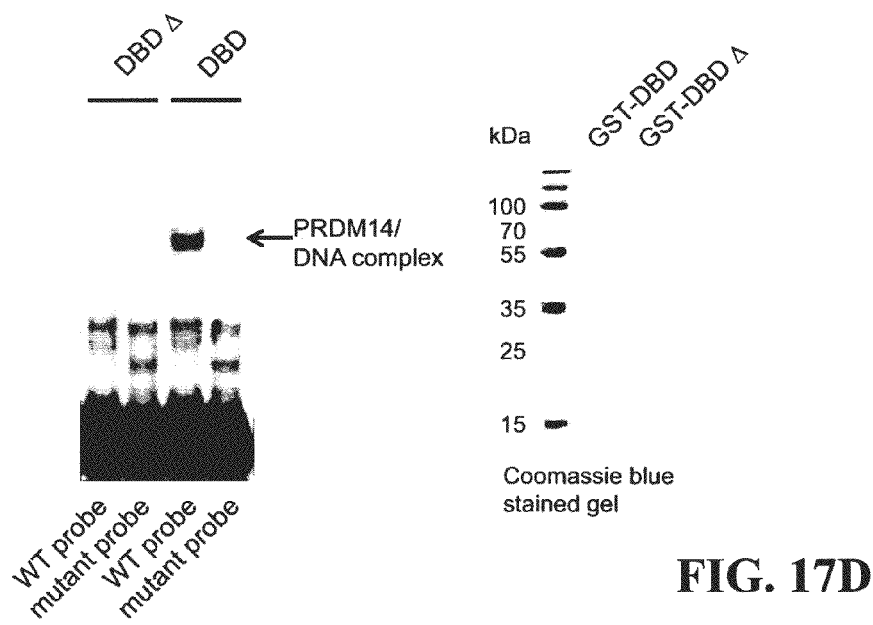
Figure 17E:
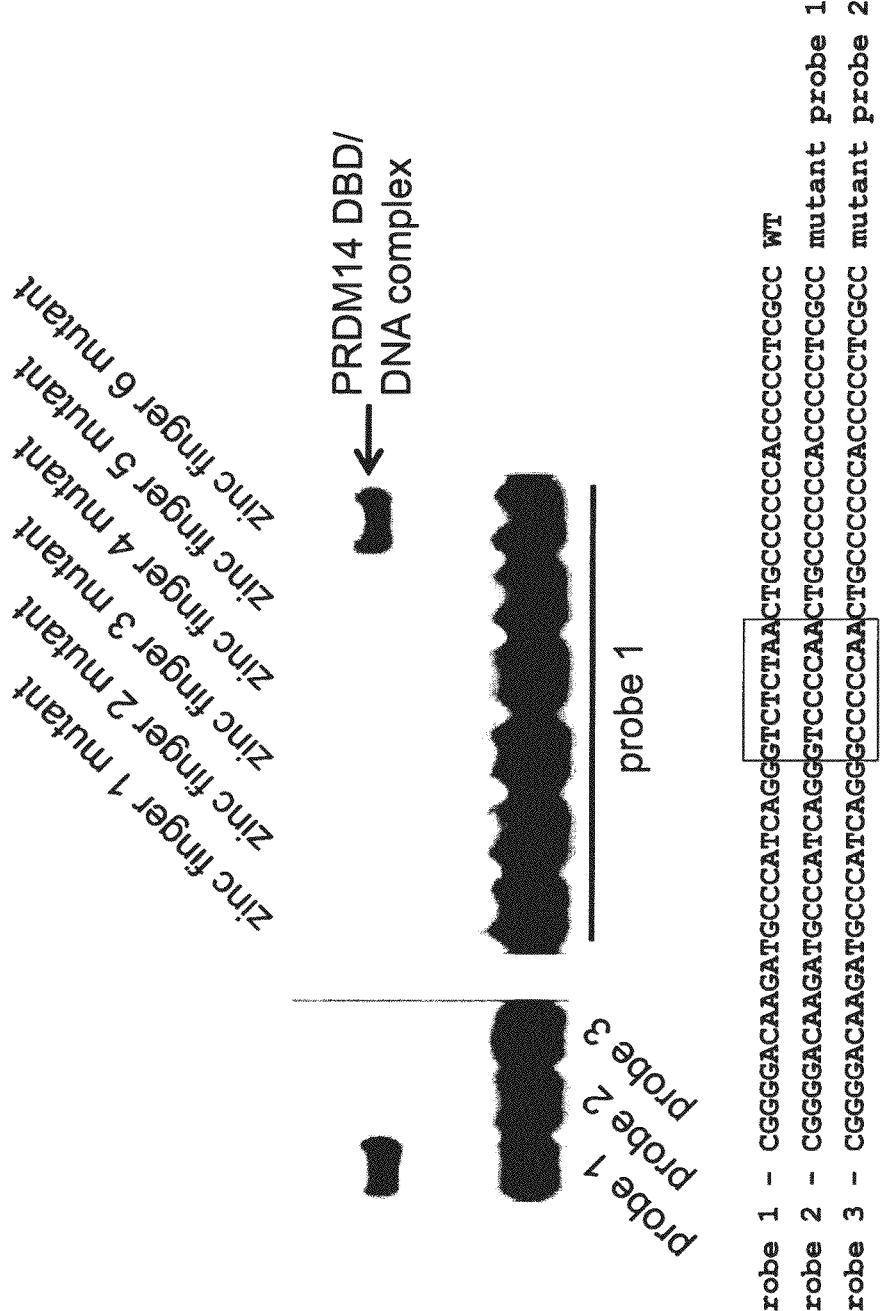
Figure 17F:
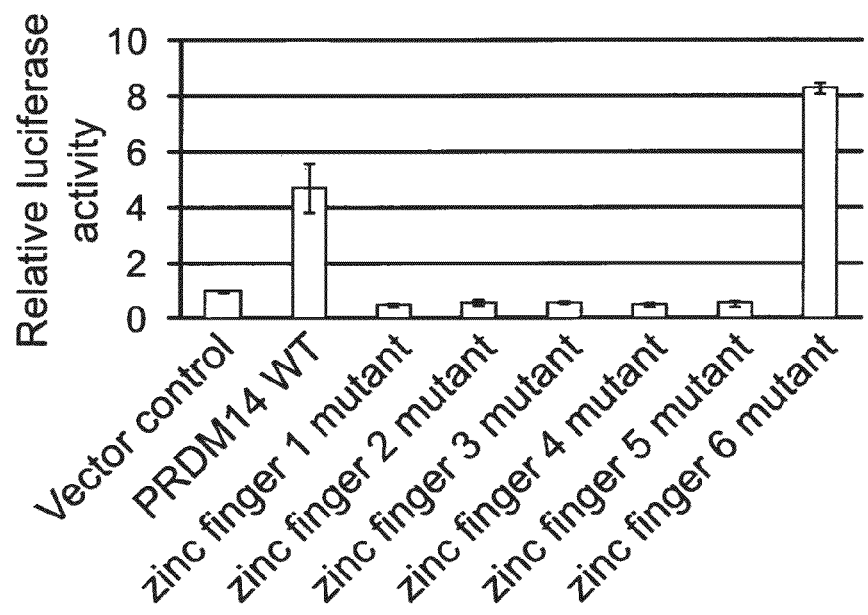

The functional domains of PRDM14 were further mapped by generating constructs expressing different fragments of the protein (FIG. 17A). These constructs were co-transfected with a CR2 reporter into 293T cells. The putative DNA binding domain (DBD) and the N-terminal region are required for transcriptional activation whereby the absence of these domains reduced the reporter activity. On the other hand, the PR/SET domain has transcriptional repression activity as deleting this domain led to a 5-fold enhancement of transcription (FIG. 17B). Importantly, it is shown that all three domains are required for the acquisition of pluripotency using the reprogramming assay (FIG. 17C). The DNA binding activity resides within the C-terminal zinc forger region as deleting this region abolished direct interaction with DNA (FIG. 17D). Five of the six zinc fingers are required for DNA binding as well as transcriptional activity (FIGS. 17E and 17F).

Figure 14H:
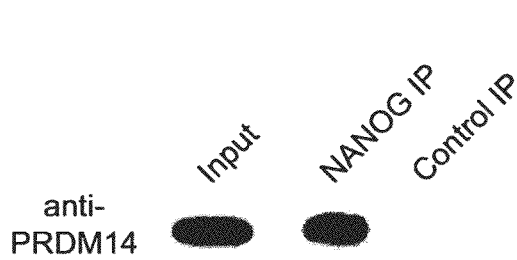
Figure 14I:
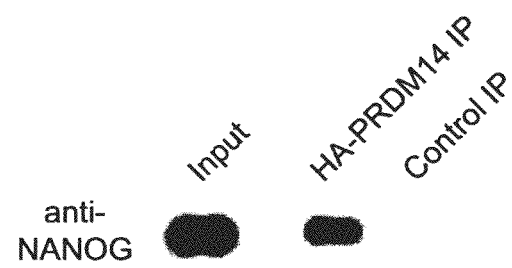
Figure 14J:
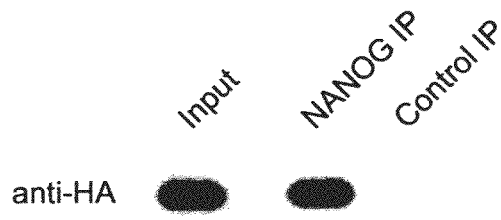
Figure 14K:
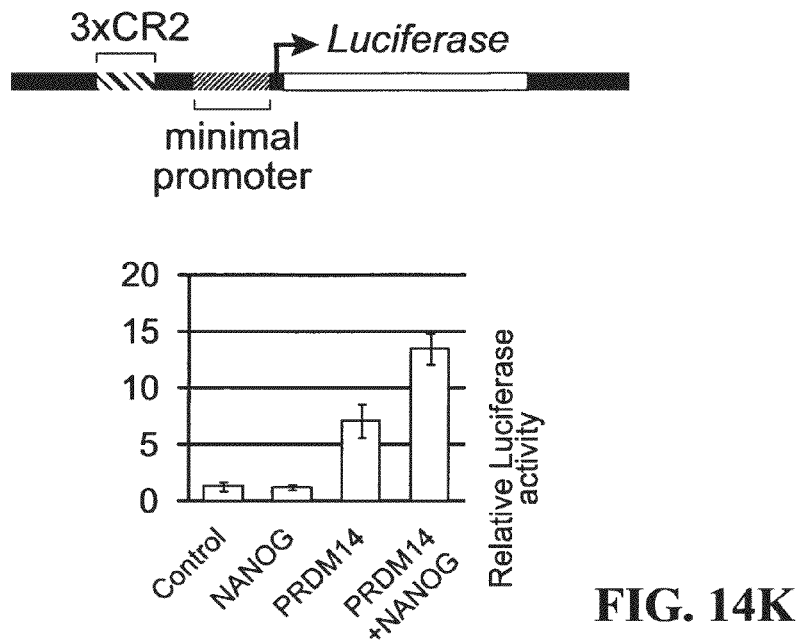
Figure 14L:
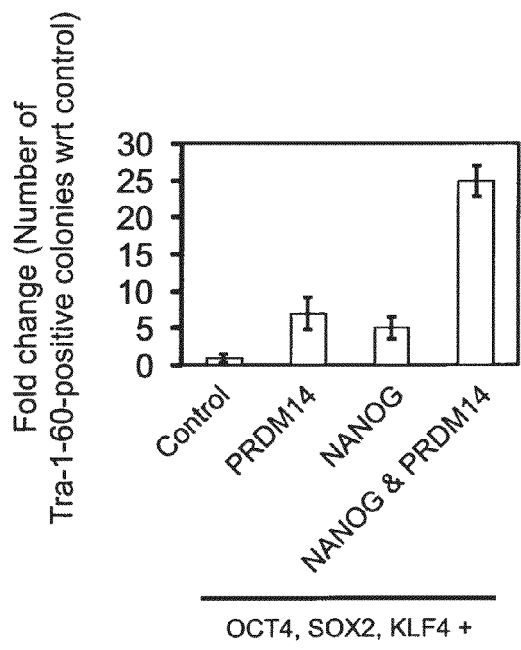

As PRDM14 showed co-localization with NANOG (FIG. 14A), the inventors sought to determine whether PRDM14 interacts with NANOG. Co-immunoprecipitation (co-IP) experiments revealed an association between the two proteins (FIGS. 14H-14J). To address whether PRDM14 can activate CR2 in somatic cells, the inventors co-transfected PRDM14 expression construct with CR2 reporter into 293T cells (FIG. 14K). Although PRDM14 could activate the CR2 reporter, NANOG can further enhance this activity in the presence of PRDM14, indicating a synergistic interaction between the two proteins (FIG. 14K). More importantly, a synergistic enhancement of reprogramming with PRDM14 and NANOG was also observed (FIG. 14L).

Taken together, it is shown that PRDM14 cooperates with NANOG to activate the CR2 enhancer of POU5F1 in hESC as well as to mediate reprogramming in human somatic cells.

Example 4

PRDM14 Recruits Polycomb Group Proteins in hESC and During Reprogramming

Figure 18A:
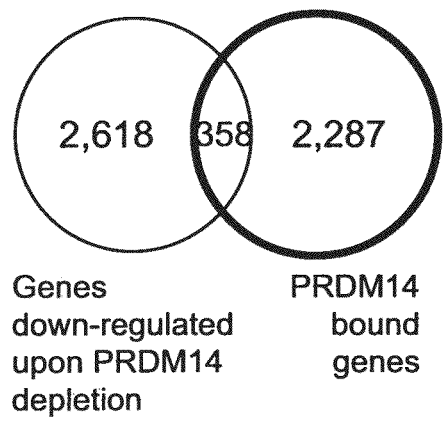

The findings above show a positive regulation of POU5F1 expression by PRDM14, which is unexpected as previous studies implicate PRDM14 as a transcriptional repressor [49, 52]. To identify the genes which are regulated by PRDM14, microarray experiments were performed to capture the transcriptome changes after the depletion of PRDM14. It is found that 358 of the 2,645 PRDM14 bound genes (13.5%) were down-regulated (FIG. 18A, Table 6). A listing of down-regulated genes is provided below in Table 6:

TABLE 6

| Genes down-regulated after depletion of PRDM14 | | |
|---|---|---|
| Gene Name | Fold change (3 d after knock-down) | q-value (%) |
| GDF3 | 0.18 | 0.4 |
| CDCA7 | 0.28 | 0.6 |
| NASP | 0.31 | 0.0 |
| HEY1 | 0.32 | 0.0 |
| PHF17 | 0.33 | 0.3 |
| SOX2 | 0.36 | 0.5 |
| C18orf56 | 0.36 | 0.0 |
| MYCN | 0.36 | 0.2 |
| TRIM71 | 0.37 | 2.6 |
| ZSCAN2 | 0.37 | 0.4 |
| PUNC | 0.37 | 0.4 |
| PRDM14 | 0.38 | 0.3 |
| IQGAP2 | 0.38 | 0.3 |
| MAP7 | 0.38 | 0.3 |
| CA4 | 0.38 | 3.5 |
| PDCD5 | 0.39 | 0.0 |
| METTL7A | 0.39 | 0.0 |
| SALL2 | 0.39 | 0.3 |
| CHCHD3 | 0.40 | 0.2 |
| STMN1 | 0.42 | 0.2 |
| GLDC | 0.42 | 1.1 |
| FZD5 | 0.43 | 0.3 |
| CHST9 | 0.43 | 0.6 |

TABLE 6-continued

Genes down-regulated after depletion of PRDM14

| Gene Name | Fold change (3 d after knockdown) | q-value (%) |
|---|---|---|
| AK3L1 | 0.43 | 0.0 |
| TGIF2 | 0.43 | 0.0 |
| ETV4 | 0.43 | 0.5 |
| RTN4IP1 | 0.43 | 0.0 |
| BCL11A | 0.44 | 2.6 |
| AXIN2 | 0.44 | 0.2 |
| ZNF649 | 0.44 | 0.6 |
| PPFIBP2 | 0.44 | 0.4 |
| SUV420H1 | 0.45 | 0.3 |
| SLC7A2 | 0.45 | 1.4 |
| HAS2 | 0.45 | 1.4 |
| KCND2 | 0.45 | 0.2 |
| GSTZ1 | 0.45 | 0.2 |
| FANCL | 0.47 | 1.4 |
| PHLPP | 0.47 | 0.8 |
| MTA3 | 0.48 | 0.2 |
| FOXO4 | 0.48 | 0.2 |
| FAM33A | 0.48 | 0.3 |
| COMTD1 | 0.48 | 3.5 |
| LRFN5 | 0.48 | 1.1 |
| SLC39A8 | 0.48 | 0.2 |
| DLG2 | 0.49 | 0.5 |
| SUOX | 0.49 | 0.3 |
| PPM1H | 0.49 | 0.0 |
| TNS3 | 0.51 | 1.1 |
| DET1 | 0.51 | 0.8 |
| LIN28 | 0.51 | 0.6 |
| SEMG1 | 0.52 | 1.9 |
| VARS | 0.52 | 1.1 |
| RIT2 | 0.52 | 1.9 |
| CCDC28B | 0.52 | 0.5 |
| ARRB1 | 0.53 | 0.2 |
| SEPHS1 | 0.53 | 0.2 |
| LAMA3 | 0.53 | 1.9 |
| DBC1 | 0.54 | 1.1 |
| TIPIN | 0.54 | 1.4 |
| RND2 | 0.54 | 0.8 |
| TCF7L1 | 0.54 | 6.0 |
| USP44 | 0.54 | 6.0 |
| MYO10 | 0.55 | 2.6 |
| TBC1D16 | 0.55 | 6.0 |
| ITPR2 | 0.56 | 0.5 |
| CDA | 0.56 | 0.5 |
| SOHLH2 | 0.56 | 0.3 |
| NOL11 | 0.56 | 0.4 |
| SDCCAG10 | 0.56 | 0.0 |
| C12orf43 | 0.56 | 0.4 |
| KAL1 | 0.56 | 0.6 |
| SRBD1 | 0.56 | 6.0 |
| MRPS28 | 0.57 | 3.5 |
| FOXO1 | 0.57 | 0.8 |
| SVOPL | 0.57 | 0.3 |
| RASL11B | 0.57 | 1.9 |
| EFHC2 | 0.57 | 0.4 |
| DNMT1 | 0.57 | 11.1 |
| HOOK2 | 0.58 | 0.5 |
| SLC35D3 | 0.58 | 0.8 |
| FOS | 0.58 | 0.8 |
| CACHD1 | 0.58 | 1.4 |
| HMMR | 0.58 | 1.4 |
| NOC4L | 0.58 | 4.5 |
| B4GALT6 | 0.58 | 3.5 |
| ZMYND8 | 0.58 | 0.3 |
| BMS1 | 0.58 | 0.6 |
| BST2 | 0.58 | 3.5 |
| SOX13 | 0.59 | 1.4 |
| CLYBL | 0.59 | 6.0 |
| C12orf35 | 0.59 | 1.9 |
| PBX1 | 0.59 | 1.1 |
| YTHDF2 | 0.60 | 8.2 |
| SNTB1 | 0.60 | 0.4 |
| HSD17B4 | 0.60 | 2.6 |
| BCOR | 0.61 | 1.9 |
| RUNX1T1 | 0.61 | 0.3 |
| WDR72 | 0.61 | 1.1 |
| SASH1 | 0.61 | 2.6 |
| WDR67 | 0.61 | 1.9 |
| AFG3L2 | 0.61 | 3.5 |
| PLCH1 | 0.61 | 3.5 |
| ITPK1 | 0.61 | 0.3 |
| MPPED2 | 0.61 | 3.5 |
| LRBA | 0.61 | 4.5 |
| GRM4 | 0.62 | 6.0 |
| SLC29A3 | 0.62 | 1.1 |
| RCOR2 | 0.62 | 8.2 |
| C17orf61 | 0.62 | 4.5 |
| LSM6 | 0.62 | 0.3 |
| INTS3 | 0.63 | 3.5 |
| FABP3 | 0.63 | 1.9 |
| EFCAB4A | 0.63 | 0.2 |
| STAP2 | 0.63 | 0.5 |
| SP3 | 0.63 | 2.6 |
| ANGPT1 | 0.63 | 0.3 |
| NOLC1 | 0.63 | 0.5 |
| NLK | 0.63 | 1.9 |
| DHX30 | 0.63 | 2.6 |
| ZFP37 | 0.63 | 0.2 |
| C14orf115 | 0.63 | 0.5 |
| LOC644096 | 0.64 | 0.2 |
| NCL | 0.64 | 3.5 |
| RASAL2 | 0.64 | 2.6 |
| SNRP70 | 0.64 | 2.6 |
| PRRT3 | 0.64 | 6.0 |
| C9orf46 | 0.65 | 1.9 |
| MSC | 0.65 | 3.5 |
| CRLF1 | 0.65 | 1.9 |
| PPARGC1B | 0.65 | 3.5 |
| LRAT | 0.65 | 8.2 |
| MTIF3 | 0.66 | 2.6 |
| TFRC | 0.66 | 2.6 |
| NLGN1 | 0.66 | 0.3 |
| ROR1 | 0.66 | 0.2 |
| ERICH1 | 0.66 | 0.4 |
| TSN | 0.66 | 8.2 |
| NMU | 0.66 | 14.8 |
| SEPT11 | 0.66 | 8.2 |
| LHFPL4 | 0.66 | 2.6 |
| ZNF219 | 0.67 | 0.4 |
| JARID2 | 0.67 | 2.6 |
| RPS7 | 0.67 | 14.8 |
| IER3IP1 | 0.67 | 3.5 |
| PRKCB1 | 0.67 | 4.5 |
| C1orf106 | 0.67 | 0.2 |
| POU5F1 | 0.67 | 14.8 |
| DEPDC2 | 0.68 | 0.6 |
| WBP4 | 0.68 | 3.5 |
| FBXL10 | 0.68 | 0.8 |
| GOLM1 | 0.68 | 4.5 |
| CCNYL1 | 0.68 | 4.5 |
| SPHK2 | 0.68 | 3.5 |
| HSD17B8 | 0.68 | 1.4 |
| CRYBA4 | 0.68 | 1.4 |
| PIAS2 | 0.68 | 6.0 |
| LARS2 | 0.69 | 0.0 |
| C3orf26 | 0.69 | 1.9 |
| C21orf59 | 0.69 | 0.3 |
| MAT2B | 0.69 | 0.8 |
| EPB41L2 | 0.69 | 0.4 |
| KIAA1576 | 0.69 | 1.1 |
| PKP4 | 0.69 | 3.5 |
| RBM17 | 0.69 | 4.5 |
| CEP110 | 0.69 | 1.9 |
| FABP6 | 0.69 | 4.5 |
| FOXD3 | 0.69 | 0.4 |

TABLE 6-continued

Genes down-regulated after depletion of PRDM14

| Gene Name | Fold change (3 d after knockdown) | q-value (%) |
|---|---|---|
| RBM23 | 0.69 | 0.3 |
| XYLT1 | 0.69 | 4.5 |
| TDGF1 | 0.69 | 4.5 |
| NICN1 | 0.70 | 1.1 |
| ACSS2 | 0.70 | 11.1 |
| FLAD1 | 0.70 | 0.6 |
| INTS10 | 0.70 | 1.1 |
| TIPRL | 0.70 | 0.8 |
| SORL1 | 0.70 | 3.5 |
| MSRA | 0.70 | 3.5 |
| SULF1 | 0.70 | 11.1 |
| ABHD12B | 0.70 | 11.1 |
| MYO5C | 0.70 | 2.6 |
| CPS1 | 0.70 | 14.8 |
| CD1D | 0.70 | 1.1 |
| CDC25A | 0.70 | 1.4 |
| DHX35 | 0.71 | 0.6 |
| TMEM144 | 0.71 | 3.5 |
| SP8 | 0.71 | 8.2 |
| PCMTD2 | 0.71 | 14.8 |
| AKR1A1 | 0.71 | 0.8 |
| TRERF1 | 0.71 | 6.0 |
| TBC1D8 | 0.71 | 1.9 |
| ZMYM6 | 0.71 | 1.9 |
| WWC1 | 0.71 | 3.5 |
| MRPL40 | 0.72 | 6.0 |
| KIAA1012 | 0.72 | 1.4 |
| POLD3 | 0.72 | 1.9 |
| SCG5 | 0.72 | 4.5 |
| C6orf70 | 0.72 | 0.8 |
| CD40 | 0.72 | 1.9 |
| DDX43 | 0.72 | 3.5 |
| ZNF23 | 0.72 | 6.0 |
| AUTS2 | 0.72 | 1.4 |
| RAB37 | 0.72 | 11.1 |
| SEPT9 | 0.72 | 6.0 |
| ARV1 | 0.72 | 2.6 |
| ALDH1A1 | 0.72 | 3.5 |
| GMPPA | 0.73 | 4.5 |
| FAM108C1 | 0.73 | 4.5 |
| GRHL2 | 0.73 | 4.5 |
| UGDH | 0.73 | 4.5 |
| POLR3GL | 0.73 | 11.1 |
| KHDRBS1 | 0.73 | 6.0 |
| CCNE2 | 0.74 | 4.5 |
| ICA1 | 0.74 | 4.5 |
| NSUN6 | 0.74 | 8.2 |
| MYO3A | 0.74 | 11.1 |
| PLXDC2 | 0.74 | 11.1 |
| FBXL6 | 0.74 | 14.8 |
| C1orf172 | 0.74 | 2.6 |
| UBE2G1 | 0.74 | 11.1 |
| RAD1 | 0.74 | 6.0 |
| CD247 | 0.74 | 0.8 |
| ZFP161 | 0.74 | 0.8 |
| MFNG | 0.75 | 6.0 |
| ZCWPW1 | 0.75 | 8.2 |
| C20orf94 | 0.75 | 6.0 |
| ZNF675 | 0.75 | 6.0 |
| KIAA0999 | 0.75 | 1.1 |
| NFATC1 | 0.75 | 14.8 |
| LYRM2 | 0.75 | 6.0 |
| HMG20A | 0.75 | 14.8 |
| RING1 | 0.75 | 8.2 |
| HPS5 | 0.75 | 0.8 |
| KIAA0644 | 0.75 | 2.6 |
| TTC4 | 0.75 | 0.2 |
| THOC1 | 0.75 | 2.6 |
| WDR59 | 0.75 | 1.9 |
| GNG2 | 0.75 | 1.9 |
| GDF11 | 0.76 | 11.1 |
| LEPREL1 | 0.76 | 3.5 |
| PITX2 | 0.76 | 3.5 |
| C21orf63 | 0.76 | 6.0 |
| PHLDB2 | 0.76 | 14.8 |
| TLN2 | 0.76 | 4.5 |
| SNCAIP | 0.76 | 6.0 |
| TMEM30B | 0.76 | 1.1 |
| AGK | 0.76 | 4.5 |
| ATP1B2 | 0.76 | 14.8 |
| ACTL6A | 0.76 | 11.1 |
| TRAF2 | 0.76 | 6.0 |
| NPTX1 | 0.76 | 6.0 |
| ZNF341 | 0.76 | 6.0 |
| PHF14 | 0.76 | 11.1 |
| BAT3 | 0.76 | 3.5 |
| GRPEL1 | 0.76 | 0.2 |
| MTX2 | 0.76 | 8.2 |
| SH2D4B | 0.77 | 1.4 |
| ARHGAP8 | 0.77 | 8.2 |
| KIAA0182 | 0.77 | 0.2 |
| SMAD6 | 0.77 | 3.5 |
| LMO3 | 0.77 | 11.1 |
| FAM125A | 0.77 | 1.9 |
| POU2F1 | 0.77 | 14.8 |
| ST6GALNAC6 | 0.77 | 6.0 |
| SRF | 0.77 | 8.2 |
| SALL3 | 0.77 | 14.8 |
| UPK1A | 0.77 | 11.1 |
| RALY | 0.77 | 1.9 |
| ZCCHC7 | 0.77 | 6.0 |
| LAPTM4B | 0.78 | 1.9 |
| PSME4 | 0.78 | 6.0 |
| C14orf118 | 0.78 | 8.2 |
| METT10D | 0.78 | 11.1 |
| SFRS12 | 0.78 | 11.1 |
| GTF3C4 | 0.78 | 4.5 |
| MMAA | 0.78 | 4.5 |
| PPP2R2B | 0.78 | 2.6 |
| ALS2CR13 | 0.78 | 8.2 |
| ZNF74 | 0.78 | 14.8 |
| GRRP1 | 0.78 | 6.0 |
| KIRREL2 | 0.79 | 11.1 |
| TAF15 | 0.79 | 6.0 |
| CCDC4 | 0.79 | 11.1 |
| ADIPOR2 | 0.79 | 4.5 |
| SP110 | 0.79 | 3.5 |
| SLC25A13 | 0.79 | 14.8 |
| TUBE1 | 0.79 | 0.4 |
| SEMA4A | 0.79 | 6.0 |
| CECR5 | 0.79 | 8.2 |
| PTCH1 | 0.79 | 8.2 |
| VPS52 | 0.79 | 1.9 |
| PVRL1 | 0.79 | 11.1 |
| PANK2 | 0.79 | 11.1 |
| SNX13 | 0.79 | 8.2 |
| ZCCHC3 | 0.79 | 11.1 |
| RFC3 | 0.79 | 14.8 |
| MMP25 | 0.79 | 2.6 |
| SOX4 | 0.79 | 6.0 |
| DSCAML1 | 0.79 | 14.8 |
| BNC2 | 0.79 | 11.1 |
| KCNQ1 | 0.79 | 14.8 |
| WDR25 | 0.79 | 14.8 |
| KIAA0406 | 0.80 | 2.6 |
| LRP2 | 0.80 | 14.8 |
| NLN | 0.80 | 11.1 |
| PDZRN3 | 0.80 | 11.1 |
| SSH3 | 0.80 | 11.1 |
| ADAMTSL1 | 0.80 | 6.0 |
| MFAP3L | 0.80 | 8.2 |
| NOSTRIN | 0.80 | 6.0 |
| CAMK1D | 0.80 | 1.9 |
| ZNF607 | 0.80 | 8.2 |

TABLE 6-continued

Genes down-regulated after depletion of PRDM14

| Gene Name | Fold change (3 d after knock-down) | q-value (%) |
|---|---|---|
| ZNF660 | 0.81 | 4.5 |
| TMEM16K | 0.81 | 8.2 |
| SH3BGRL2 | 0.81 | 8.2 |
| SEMA5B | 0.81 | 6.0 |
| E2F3 | 0.81 | 6.0 |
| ACADSB | 0.81 | 14.8 |
| ZFP90 | 0.81 | 2.6 |
| FREM2 | 0.81 | 14.8 |
| BCL9 | 0.81 | 1.1 |
| BMPR1A | 0.81 | 11.1 |
| HOXB1 | 0.81 | 8.2 |
| APC | 0.81 | 11.1 |
| RBMS1 | 0.81 | 8.2 |
| DAAM1 | 0.81 | 14.8 |
| HDGF | 0.82 | 1.4 |
| WNT3A | 0.82 | 8.2 |
| TDRD3 | 0.82 | 4.5 |
| SLCO4C1 | 0.82 | 4.5 |
| BDH1 | 0.82 | 11.1 |
| HERC1 | 0.82 | 3.5 |
| ATP4A | 0.82 | 14.8 |
| EIF4A3 | 0.82 | 3.5 |
| GPC3 | 0.82 | 8.2 |
| PCCA | 0.82 | 11.1 |
| ERCC6 | 0.82 | 11.1 |
| RSF1 | 0.82 | 6.0 |
| LRRC2 | 0.82 | 8.2 |
| ZNF429 | 0.82 | 8.2 |
| SLC44A3 | 0.82 | 14.8 |
| PGM1 | 0.82 | 8.2 |
| CDCA4 | 0.82 | 11.1 |
| LYPD6 | 0.82 | 8.2 |
| MYO5A | 0.83 | 14.8 |
| SPIRE2 | 0.83 | 14.8 |
| ORAI3 | 0.83 | 11.1 |
| GABRG2 | 0.83 | 6.0 |
| JMJD2C | 0.83 | 1.9 |
| CAB39L | 0.83 | 8.2 |
| IQCE | 0.83 | 14.8 |
| ACTL6B | 0.83 | 8.2 |
| AQP2 | 0.83 | 14.8 |
| FLJ46082 | 0.83 | 14.8 |
| CPSF6 | 0.83 | 6.0 |
| BTBD16 | 0.83 | 14.8 |
| ART3 | 0.83 | 6.0 |
| TRIM9 | 0.83 | 3.5 |
| TARBP1 | 0.83 | 11.1 |

Figure 18B:
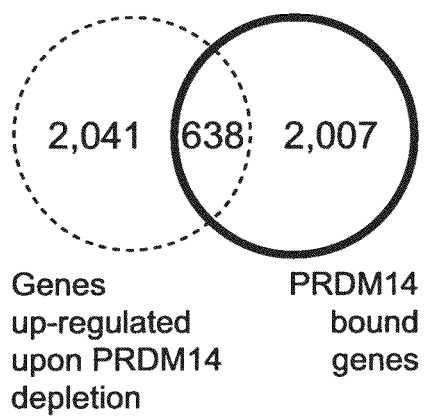

Conversely, 638 of the PRDM14 bound genes (24.1%) were induced (FIG. 18B, Table 7). A listing of induced genes is provided below in Table 7:

TABLE 7

Genes induced after depletion of PRDM14

| Gene Name | Fold change (3 days after knock-down) | q-value (%) |
|---|---|---|
| IGFBP5 | 37.31 | 0.0 |
| FOXD1 | 17.60 | 0.0 |
| FZD2 | 11.44 | 0.0 |
| CST1 | 10.06 | 0.0 |
| TIMP3 | 9.64 | 0.6 |
| PAPPA | 9.45 | 0.0 |
| MSX1 | 9.07 | 0.0 |
| ANKRD1 | 9.00 | 0.1 |
| CCDC92 | 8.77 | 0.0 |
| CADM1 | 8.60 | 0.0 |
| ALPK2 | 8.46 | 0.0 |
| PTHLH | 7.75 | 0.0 |
| PRICKLE2 | 7.45 | 0.0 |
| S100A6 | 7.41 | 0.0 |
| NOX4 | 7.38 | 0.0 |
| ITGA5 | 7.29 | 0.0 |
| F2RL1 | 7.28 | 0.1 |
| UBE2J1 | 6.98 | 0.0 |
| TBC1D9 | 6.83 | 0.1 |
| PALLD | 6.33 | 0.0 |
| PNMA2 | 6.28 | 0.0 |
| SPP1 | 6.00 | 0.2 |
| RHOB | 5.78 | 0.0 |
| MAFB | 5.76 | 0.0 |
| CAPN2 | 5.40 | 0.0 |
| UNC84B | 5.40 | 0.0 |
| PDGFB | 5.33 | 0.1 |
| S100A16 | 5.25 | 0.0 |
| NUAK2 | 4.85 | 0.2 |
| BCAR3 | 4.84 | 0.0 |
| ZFHX3 | 4.75 | 0.5 |
| PLAUR | 4.73 | 0.2 |
| OAF | 4.72 | 0.0 |
| GPR177 | 4.55 | 0.3 |
| BTG2 | 4.42 | 0.1 |
| HNT | 4.39 | 0.2 |
| ANTXR2 | 4.33 | 0.0 |
| AFAP1L2 | 4.32 | 0.0 |
| RUNX1 | 4.30 | 0.2 |
| COL1A2 | 4.15 | 0.0 |
| RGS20 | 4.14 | 0.1 |
| TNFRSF19 | 4.13 | 0.1 |
| ASS1 | 4.07 | 0.2 |
| PTRF | 4.02 | 0.0 |
| SMYD2 | 3.90 | 0.0 |
| CAMK2N1 | 3.82 | 0.3 |
| GPRC5C | 3.80 | 0.2 |
| CALCA | 3.60 | 0.0 |
| PHC2 | 3.58 | 0.1 |
| FBN2 | 3.56 | 0.4 |
| RBM24 | 3.53 | 0.0 |
| GPR87 | 3.51 | 0.8 |
| SFN | 3.47 | 0.2 |
| PAG1 | 3.45 | 0.0 |
| SEMA3C | 3.41 | 0.3 |
| CLDN11 | 3.38 | 0.2 |
| CDC42EP3 | 3.37 | 0.3 |
| USP3 | 3.37 | 0.2 |
| BMP4 | 3.33 | 0.3 |
| LHX1 | 3.31 | 0.0 |
| FRMD6 | 3.26 | 0.3 |
| NGF | 3.25 | 0.0 |
| MN1 | 3.24 | 0.0 |
| RHOBTB3 | 3.24 | 0.3 |
| BMF | 3.23 | 0.3 |
| EMILIN2 | 3.23 | 0.0 |
| ATP2B4 | 3.19 | 0.1 |
| EFNB2 | 3.17 | 0.0 |
| FGF1 | 3.17 | 0.4 |
| LPP | 3.16 | 0.2 |
| RAB31 | 3.15 | 0.1 |
| CDC42EP1 | 3.15 | 0.1 |
| CDC2L6 | 3.12 | 0.0 |
| SVIL | 3.11 | 0.0 |
| ZNF518B | 3.10 | 0.0 |
| CDH2 | 3.09 | 0.0 |
| RUNX3 | 3.05 | 0.0 |
| TMEM123 | 3.04 | 1.1 |
| CCDC50 | 3.02 | 0.0 |
| NRP2 | 2.98 | 0.2 |

TABLE 7-continued

Genes induced after depletion of PRDM14

| Gene Name | Fold change (3 days after knockdown) | q-value (%) |
|---|---|---|
| MBNL2 | 2.97 | 0.2 |
| FAM24B | 2.96 | 0.4 |
| MYH9 | 2.96 | 0.3 |
| GJB2 | 2.93 | 0.2 |
| CUEDC1 | 2.93 | 0.8 |
| LIMCH1 | 2.91 | 0.0 |
| SPON1 | 2.89 | 0.0 |
| PTPRM | 2.89 | 0.3 |
| ANXA2 | 2.86 | 0.1 |
| PEAR1 | 2.83 | 0.6 |
| SMAD3 | 2.79 | 0.1 |
| TSPAN5 | 2.77 | 1.4 |
| CYP1B1 | 2.76 | 0.5 |
| SLC1A4 | 2.75 | 0.0 |
| LIMS1 | 2.75 | 0.1 |
| IER5L | 2.73 | 0.5 |
| GSN | 2.72 | 1.1 |
| CAMK2D | 2.72 | 0.5 |
| TNFRSF10B | 2.70 | 0.1 |
| SIPA1L2 | 2.68 | 0.0 |
| FLRT2 | 2.67 | 0.6 |
| SCHIP1 | 2.66 | 0.2 |
| CALD1 | 2.66 | 0.6 |
| STEAP3 | 2.66 | 0.2 |
| MAMDC2 | 2.63 | 1.4 |
| SLC25A37 | 2.62 | 0.0 |
| IER5 | 2.61 | 0.0 |
| CPXM2 | 2.59 | 0.0 |
| CDKN2A | 2.57 | 0.8 |
| TTC3 | 2.57 | 0.2 |
| ARNTL | 2.56 | 0.2 |
| ID3 | 2.54 | 1.1 |
| PRKCA | 2.54 | 0.1 |
| GALNT10 | 2.54 | 0.5 |
| C6orf15 | 2.54 | 0.0 |
| ACTN1 | 2.52 | 0.2 |
| OLFML3 | 2.51 | 0.1 |
| FOSL1 | 2.49 | 0.1 |
| H2AFY2 | 2.48 | 0.0 |
| PQLC1 | 2.48 | 0.1 |
| SH3BGRL3 | 2.48 | 0.8 |
| TNFRSF21 | 2.46 | 0.3 |
| CHST7 | 2.46 | 0.0 |
| PGCP | 2.45 | 0.5 |
| DUSP10 | 2.45 | 0.0 |
| ODZ3 | 2.44 | 0.1 |
| LAMC1 | 2.43 | 0.3 |
| GRK5 | 2.43 | 0.2 |
| CDC42EP4 | 2.42 | 0.2 |
| C10orf59 | 2.42 | 0.0 |
| AFF3 | 2.38 | 0.2 |
| RGS16 | 2.38 | 0.0 |
| DDEF1 | 2.38 | 0.2 |
| EDEM1 | 2.37 | 0.1 |
| ANXA3 | 2.37 | 0.1 |
| ARID5B | 2.37 | 0.3 |
| COL4A2 | 2.35 | 1.4 |
| ALDH1A3 | 2.35 | 0.0 |
| H2AFY | 2.34 | 0.2 |
| APCDD1 | 2.34 | 0.1 |
| SH3PXD2A | 2.34 | 0.2 |
| DERA | 2.32 | 0.0 |
| WBP5 | 2.32 | 0.1 |
| ZHX2 | 2.32 | 0.2 |
| HERC4 | 2.30 | 1.1 |
| RTN4 | 2.29 | 0.3 |
| CES1 | 2.28 | 1.4 |
| ETV5 | 2.27 | 0.2 |
| SH3RF2 | 2.27 | 0.2 |
| WEE1 | 2.27 | 0.8 |
| EFNA1 | 2.26 | 0.3 |
| NBPF10 | 2.26 | 6.0 |
| BDNF | 2.25 | 0.3 |
| ARHGAP21 | 2.24 | 0.1 |
| S100A11 | 2.24 | 0.4 |
| RFTN1 | 2.24 | 0.0 |
| EXT1 | 2.24 | 0.2 |
| HS6ST2 | 2.23 | 0.0 |
| SULF2 | 2.23 | 0.3 |
| MEF2D | 2.23 | 0.2 |
| ST3GAL1 | 2.23 | 0.0 |
| CNTNAP1 | 2.23 | 0.2 |
| VPS37B | 2.22 | 0.4 |
| MAP1A | 2.21 | 1.1 |
| CTSL2 | 2.20 | 0.1 |
| GLIPR1L1 | 2.18 | 0.4 |
| SIRPA | 2.17 | 0.5 |
| COL4A1 | 2.16 | 0.0 |
| CDK6 | 2.16 | 0.0 |
| DACH1 | 2.15 | 0.0 |
| CUGBP2 | 2.15 | 0.2 |
| PTPN14 | 2.14 | 0.1 |
| SAMD4A | 2.14 | 0.4 |
| SETD8 | 2.14 | 1.4 |
| CDH13 | 2.13 | 0.1 |
| SPAG1 | 2.13 | 0.2 |
| EFHD1 | 2.13 | 2.6 |
| MMP2 | 2.12 | 1.9 |
| TXNRD1 | 2.11 | 2.6 |
| TMCO3 | 2.10 | 0.4 |
| LOC162073 | 2.10 | 1.4 |
| PPARG | 2.10 | 0.1 |
| IGF1R | 2.09 | 0.1 |
| FOXK1 | 2.07 | 0.4 |
| TUBA4A | 2.07 | 0.6 |
| ADAM17 | 2.06 | 0.1 |
| NBPF20 | 2.04 | 6.0 |
| MERTK | 2.04 | 0.0 |
| CMBL | 2.03 | 0.0 |
| PRDM8 | 2.03 | 1.4 |
| CPNE4 | 2.03 | 0.2 |
| HMGA2 | 2.03 | 0.0 |
| ACVR1B | 2.02 | 0.0 |
| PMP22 | 2.02 | 0.2 |
| RAI1 | 2.02 | 1.1 |
| NTNG1 | 2.02 | 0.3 |
| NECAP2 | 2.01 | 0.1 |
| ZNF532 | 2.01 | 0.1 |
| GOLGA8B | 2.01 | 0.0 |
| FILIP1L | 2.01 | 0.2 |
| BACH2 | 2.01 | 0.3 |
| MYL7 | 2.00 | 0.8 |
| CDCP1 | 2.00 | 0.3 |
| PPP1R14A | 1.99 | 0.0 |
| ZNF800 | 1.99 | 0.5 |
| SLC7A5 | 1.99 | 0.3 |
| BIN1 | 1.98 | 0.6 |
| FAM129A | 1.97 | 4.5 |
| LCOR | 1.96 | 0.2 |
| BCL2L1 | 1.96 | 0.5 |
| NOPE | 1.96 | 0.2 |
| GNG3 | 1.96 | 0.2 |
| CDX1 | 1.95 | 1.1 |
| GDPD5 | 1.95 | 0.5 |
| CORO2B | 1.94 | 0.6 |
| LSAMP | 1.94 | 0.0 |
| STARD13 | 1.93 | 0.0 |
| KCNMA1 | 1.92 | 0.0 |
| COBL | 1.92 | 0.4 |
| PKM2 | 1.92 | 0.2 |
| TSPAN14 | 1.91 | 8.2 |
| GPC6 | 1.90 | 0.3 |
| TSPAN18 | 1.89 | 8.2 |
| PKNOX2 | 1.88 | 0.6 |

TABLE 7-continued

Genes induced after depletion of PRDM14

| Gene Name | Fold change (3 days after knockdown) | q-value (%) |
|---|---|---|
| GPC1 | 1.87 | 0.8 |
| KLF9 | 1.87 | 0.6 |
| TRIO | 1.87 | 0.6 |
| CADM4 | 1.87 | 0.3 |
| PPARGC1A | 1.87 | 1.1 |
| CLEC16A | 1.86 | 0.6 |
| NUAK1 | 1.86 | 1.1 |
| SLC35F2 | 1.85 | 0.2 |
| ZAK | 1.85 | 0.5 |
| TBL2 | 1.85 | 0.4 |
| TMEM41B | 1.85 | 0.1 |
| ASXL1 | 1.84 | 0.1 |
| ELL2 | 1.84 | 0.3 |
| TBC1D19 | 1.84 | 0.6 |
| LAMB1 | 1.83 | 0.5 |
| SPRED2 | 1.83 | 0.1 |
| LEMD2 | 1.83 | 0.8 |
| PPFIBP1 | 1.81 | 0.3 |
| UFM1 | 1.81 | 0.5 |
| CDC25B | 1.81 | 0.3 |
| USP53 | 1.80 | 0.5 |
| C11orf17 | 1.80 | 1.1 |
| RRAGD | 1.80 | 0.0 |
| NT5C2 | 1.80 | 0.0 |
| PDE4D | 1.79 | 0.5 |
| COTL1 | 1.78 | 6.0 |
| ZNF823 | 1.78 | 0.4 |
| CNTNAP2 | 1.78 | 0.2 |
| ZMIZ1 | 1.76 | 0.1 |
| TMEM16F | 1.76 | 1.4 |
| GPR176 | 1.76 | 2.6 |
| EFNB1 | 1.75 | 0.3 |
| SGPL1 | 1.75 | 1.1 |
| PRKCH | 1.75 | 2.6 |
| CDH10 | 1.75 | 0.6 |
| HERPUD1 | 1.75 | 1.4 |
| DUSP12 | 1.75 | 0.6 |
| PTK7 | 1.75 | 0.8 |
| TMEM14A | 1.74 | 0.2 |
| XKR4 | 1.74 | 2.6 |
| ACTR3 | 1.74 | 2.6 |
| LASS6 | 1.74 | 3.5 |
| MTMR3 | 1.73 | 1.9 |
| UBE2H | 1.73 | 1.1 |
| RAPH1 | 1.73 | 0.0 |
| PM20D2 | 1.73 | 0.6 |
| CDS2 | 1.72 | 1.4 |
| JDP2 | 1.72 | 0.2 |
| AFAP1 | 1.71 | 1.4 |
| ADAMTS9 | 1.71 | 1.9 |
| B4GALT1 | 1.71 | 0.6 |
| RCAN2 | 1.71 | 2.6 |
| CLDN6 | 1.71 | 2.6 |
| FOXA1 | 1.71 | 0.2 |
| HIVEP1 | 1.70 | 0.5 |
| FNBP1 | 1.70 | 0.0 |
| C10orf141 | 1.70 | 0.0 |
| NANOS3 | 1.70 | 0.4 |
| PARVA | 1.69 | 0.0 |
| CNN2 | 1.69 | 0.6 |
| JUND | 1.69 | 0.3 |
| PIGG | 1.69 | 1.9 |
| JUP | 1.69 | 0.8 |
| AKAP13 | 1.69 | 0.2 |
| PXN | 1.69 | 0.2 |
| PHF19 | 1.69 | 0.3 |
| IGFBP2 | 1.68 | 0.0 |
| LHFP | 1.68 | 4.5 |
| TMEM88 | 1.68 | 1.9 |
| RRAS | 1.68 | 0.1 |
| MBOAT1 | 1.68 | 0.2 |
| C2orf18 | 1.68 | 4.5 |
| GAD1 | 1.67 | 8.2 |
| PARP3 | 1.67 | 0.2 |
| PLEKHG3 | 1.66 | 2.6 |
| RAB11A | 1.65 | 0.2 |
| DDAH1 | 1.65 | 1.4 |
| LIMS2 | 1.64 | 1.4 |
| FAM110B | 1.64 | 1.9 |
| PID1 | 1.64 | 0.3 |
| TOX3 | 1.64 | 0.8 |
| EGLN1 | 1.63 | 1.1 |
| TANC1 | 1.63 | 1.4 |
| CDYL | 1.63 | 1.4 |
| WNT5B | 1.63 | 0.6 |
| PCDH19 | 1.63 | 0.5 |
| ABTB2 | 1.63 | 8.2 |
| CENTG3 | 1.62 | 3.5 |
| JAG1 | 1.62 | 0.8 |
| SMCR7L | 1.62 | 2.6 |
| GFOD1 | 1.62 | 0.3 |
| NBPF3 | 1.62 | 2.6 |
| PICALM | 1.62 | 4.5 |
| IQCK | 1.62 | 1.9 |
| ARID3A | 1.61 | 0.5 |
| GRHL3 | 1.61 | 1.9 |
| SFRP1 | 1.61 | 0.6 |
| KCTD20 | 1.60 | 0.6 |
| NAV2 | 1.60 | 6.0 |
| PTK2 | 1.60 | 0.0 |
| LYL1 | 1.60 | 4.5 |
| CAP1 | 1.59 | 0.3 |
| KCNK1 | 1.59 | 4.5 |
| NENF | 1.59 | 8.2 |
| TNS1 | 1.59 | 0.3 |
| TCEA3 | 1.58 | 1.4 |
| ADCY9 | 1.58 | 0.4 |
| C12orf5 | 1.58 | 2.6 |
| NCOA6 | 1.58 | 0.2 |
| DENND1A | 1.57 | 1.4 |
| FYN | 1.57 | 0.2 |
| C1orf144 | 1.57 | 1.9 |
| NDFIP1 | 1.57 | 3.5 |
| DCTN5 | 1.57 | 0.0 |
| NUMB | 1.57 | 1.4 |
| HCK | 1.57 | 2.6 |
| SERPINB8 | 1.57 | 1.1 |
| MAPKAPK2 | 1.56 | 1.1 |
| RNF24 | 1.56 | 0.3 |
| TRAF5 | 1.56 | 0.3 |
| LMAN2L | 1.56 | 0.0 |
| ZNF521 | 1.56 | 0.2 |
| DLGAP4 | 1.55 | 1.1 |
| ADAMTS5 | 1.55 | 1.9 |
| KIAA1128 | 1.55 | 2.6 |
| NFIC | 1.55 | 11.1 |
| CDC42BPA | 1.55 | 1.9 |
| TMEM131 | 1.54 | 0.5 |
| MACF1 | 1.54 | 0.2 |
| MAST4 | 1.54 | 6.0 |
| IL4R | 1.54 | 0.0 |
| P2RX4 | 1.54 | 6.0 |
| ZEB2 | 1.53 | 0.3 |
| C16orf72 | 1.53 | 1.4 |
| KCTD10 | 1.53 | 1.1 |
| GARNL4 | 1.53 | 1.4 |
| ARHGEF17 | 1.53 | 4.5 |
| RNF216 | 1.53 | 3.5 |
| KIAA0922 | 1.52 | 1.4 |
| ACADL | 1.52 | 2.6 |
| MPZL1 | 1.52 | 0.2 |
| SPRYD3 | 1.52 | 8.2 |
| RARA | 1.52 | 0.8 |
| SOCS3 | 1.52 | 2.6 |

TABLE 7-continued

Genes induced after depletion of PRDM14

| Gene Name | Fold change (3 days after knock-down) | q-value (%) |
|---|---|---|
| DR1 | 1.52 | 4.5 |
| GLT25D1 | 1.52 | 0.3 |
| CRIP1 | 1.52 | 6.0 |
| ARHGEF6 | 1.51 | 0.6 |
| SLC46A1 | 1.51 | 0.8 |
| TSPAN15 | 1.51 | 0.8 |
| SH3GL3 | 1.51 | 6.0 |
| COL4A6 | 1.51 | 0.0 |
| CENTG2 | 1.51 | 2.6 |
| SRGAP1 | 1.51 | 8.2 |
| FAM125B | 1.51 | 0.2 |
| PIGH | 1.50 | 1.9 |
| DDR1 | 1.50 | 4.5 |
| CSMD2 | 1.50 | 0.6 |
| CSAD | 1.50 | 1.1 |
| CEBPG | 1.50 | 0.0 |
| PACS1 | 1.50 | 3.5 |
| NFKB2 | 1.50 | 3.5 |
| GCH1 | 1.49 | 8.2 |
| BCAT2 | 1.49 | 0.3 |
| CANT1 | 1.49 | 0.8 |
| ENDOD1 | 1.49 | 0.6 |
| CAP2 | 1.48 | 3.5 |
| PRKD1 | 1.48 | 3.5 |
| MAN1B1 | 1.48 | 2.6 |
| IRS1 | 1.48 | 0.1 |
| KIF5B | 1.48 | 8.2 |
| BASP1 | 1.48 | 2.6 |
| DHX32 | 1.47 | 4.5 |
| SLC35B3 | 1.47 | 1.1 |
| SPTAN1 | 1.46 | 6.0 |
| SFXN5 | 1.46 | 8.2 |
| KCTD1 | 1.46 | 8.2 |
| CTTN | 1.46 | 8.2 |
| C20orf43 | 1.46 | 0.8 |
| ANK1 | 1.45 | 2.6 |
| PARP6 | 1.45 | 2.6 |
| C18orf24 | 1.45 | 0.6 |
| GGH | 1.45 | 0.6 |
| GLT25D2 | 1.45 | 0.8 |
| PURA | 1.45 | 1.1 |
| C18orf1 | 1.45 | 3.5 |
| HSF2BP | 1.45 | 1.9 |
| KIAA1026 | 1.45 | 1.4 |
| RGAG4 | 1.44 | 14.8 |
| GJA3 | 1.44 | 4.5 |
| ABHD14A | 1.44 | 0.5 |
| HHAT | 1.44 | 4.5 |
| ZNF213 | 1.44 | 0.3 |
| AMMECR1L | 1.44 | 6.0 |
| GNA14 | 1.44 | 3.5 |
| SMYD3 | 1.43 | 2.6 |
| IFFO | 1.43 | 3.5 |
| SERTAD2 | 1.43 | 0.8 |
| OLIG2 | 1.43 | 3.5 |
| DNAJB5 | 1.43 | 0.8 |
| KLF13 | 1.43 | 4.5 |
| BCAS4 | 1.43 | 3.5 |
| GABBR2 | 1.43 | 3.5 |
| C11orf49 | 1.43 | 2.6 |
| TGIF1 | 1.43 | 0.4 |
| RFFL | 1.42 | 8.2 |
| MLL | 1.42 | 0.0 |
| TBC1D20 | 1.42 | 1.4 |
| SPCS3 | 1.42 | 11.1 |
| TRIM44 | 1.42 | 0.8 |
| CHD9 | 1.42 | 1.9 |
| COG5 | 1.42 | 1.4 |
| TRIP4 | 1.42 | 6.0 |
| CNOT6 | 1.42 | 3.5 |
| SLMO1 | 1.41 | 2.6 |
| GPC4 | 1.41 | 3.5 |
| GLRX2 | 1.41 | 8.2 |
| DSCR6 | 1.41 | 1.4 |
| SLC29A4 | 1.41 | 2.6 |
| GTF2IRD2B | 1.41 | 2.6 |
| ZNF503 | 1.41 | 1.1 |
| FAM116A | 1.40 | 6.0 |
| ITFG1 | 1.40 | 3.5 |
| ZNF154 | 1.40 | 0.4 |
| RHOG | 1.40 | 3.5 |
| ATN1 | 1.40 | 8.2 |
| MGC24039 | 1.40 | 4.5 |
| RABL5 | 1.40 | 8.2 |
| YPEL2 | 1.40 | 3.5 |
| FAM62B | 1.40 | 0.4 |
| TCF12 | 1.39 | 14.8 |
| HP1BP3 | 1.39 | 0.5 |
| ANP32B | 1.39 | 4.5 |
| FBXW7 | 1.39 | 4.5 |
| STX12 | 1.39 | 6.0 |
| SSR2 | 1.39 | 11.1 |
| CALN1 | 1.39 | 1.9 |
| BCL7C | 1.39 | 0.4 |
| PTPLB | 1.38 | 8.2 |
| ZDHHC14 | 1.38 | 2.6 |
| GAB2 | 1.38 | 1.9 |
| TRH | 1.38 | 4.5 |
| CLDN3 | 1.38 | 2.6 |
| RAB25 | 1.37 | 0.5 |
| YWHAQ | 1.37 | 0.4 |
| EEF1G | 1.37 | 8.2 |
| NBPF1 | 1.37 | 6.0 |
| IGF2BP2 | 1.37 | 4.5 |
| SLC35C1 | 1.37 | 11.1 |
| KRT8 | 1.37 | 2.6 |
| RNF130 | 1.36 | 6.0 |
| AVEN | 1.36 | 8.2 |
| CCKBR | 1.36 | 11.1 |
| MAP3K7 | 1.36 | 1.4 |
| TLN1 | 1.36 | 1.9 |
| PLAC8 | 1.36 | 1.4 |
| MGC70863 | 1.36 | 11.1 |
| NKTR | 1.35 | 8.2 |
| AADACL1 | 1.35 | 8.2 |
| SMAD5 | 1.35 | 11.1 |
| CACNA2D3 | 1.35 | 14.8 |
| TEGT | 1.35 | 0.3 |
| HKDC1 | 1.35 | 4.5 |
| MAP4K4 | 1.35 | 1.1 |
| ITGA11 | 1.35 | 4.5 |
| RP9 | 1.35 | 8.2 |
| LHX2 | 1.35 | 6.0 |
| DYSF | 1.35 | 14.8 |
| AIG1 | 1.35 | 4.5 |
| SYT7 | 1.35 | 3.5 |
| ROR2 | 1.35 | 8.2 |
| FAT | 1.34 | 11.1 |
| WDR51B | 1.34 | 4.5 |
| DOCK3 | 1.34 | 1.9 |
| MEIS1 | 1.34 | 0.3 |
| GOLSYN | 1.34 | 8.2 |
| ARF5 | 1.34 | 1.1 |
| SUPT3H | 1.33 | 6.0 |
| IL1RAPL1 | 1.33 | 3.5 |
| RNF4 | 1.33 | 0.8 |
| FXR2 | 1.33 | 4.5 |
| MEX3B | 1.33 | 1.4 |
| CPEB4 | 1.33 | 6.0 |
| UBE2E2 | 1.32 | 3.5 |
| ODF2L | 1.32 | 6.0 |
| TTYH3 | 1.32 | 3.5 |
| CLASP2 | 1.32 | 14.8 |
| PMAIP1 | 1.32 | 6.0 |

TABLE 7-continued

Genes induced after depletion of PRDM14

| Gene Name | Fold change (3 days after knock-down) | q-value (%) |
|---|---|---|
| C10orf116 | 1.32 | 6.0 |
| TMOD3 | 1.32 | 14.8 |
| STK24 | 1.32 | 1.4 |
| YWHAZ | 1.32 | 4.5 |
| IL1RAP | 1.32 | 6.0 |
| RGS9 | 1.31 | 6.0 |
| MGST3 | 1.31 | 3.5 |
| GOT1 | 1.31 | 2.6 |
| CSHL1 | 1.31 | 0.6 |
| MEX3D | 1.31 | 2.6 |
| CYP26B1 | 1.31 | 6.0 |
| ARHGEF2 | 1.31 | 6.0 |
| UNC5A | 1.31 | 11.1 |
| SLC15A4 | 1.31 | 6.0 |
| ARHGAP30 | 1.31 | 4.5 |
| DLX5 | 1.31 | 0.3 |
| KIAA0746 | 1.31 | 1.4 |
| RHEB | 1.30 | 0.1 |
| TACSTD2 | 1.30 | 1.4 |
| NAG | 1.30 | 14.8 |
| SNAP25 | 1.30 | 3.5 |
| DACT1 | 1.30 | 8.2 |
| SLC4A2 | 1.30 | 2.6 |
| GBF1 | 1.30 | 11.1 |
| UHRF2 | 1.30 | 2.6 |
| CCDC109A | 1.30 | 14.8 |
| MICAL2 | 1.30 | 14.8 |
| ARAF | 1.30 | 4.5 |
| PLLP | 1.30 | 4.5 |
| PPP1R14C | 1.30 | 8.2 |
| THRA | 1.29 | 6.0 |
| TEAD3 | 1.29 | 6.0 |
| MYO1D | 1.29 | 0.3 |
| ACOX3 | 1.29 | 3.5 |
| PHF21A | 1.29 | 1.9 |
| MTA2 | 1.29 | 14.8 |
| SCUBE3 | 1.29 | 4.5 |
| MAGED1 | 1.29 | 11.1 |
| RRAS2 | 1.29 | 11.1 |
| MLL5 | 1.28 | 8.2 |
| STARD3 | 1.28 | 0.8 |
| TOMM34 | 1.28 | 11.1 |
| WDR51A | 1.28 | 3.5 |
| CCDC126 | 1.28 | 3.5 |
| NELL1 | 1.28 | 1.4 |
| DPF3 | 1.28 | 1.9 |
| MAN1A1 | 1.28 | 6.0 |
| MEMO1 | 1.28 | 4.5 |
| FSCN1 | 1.28 | 4.5 |
| RAPGEF1 | 1.28 | 14.8 |
| SORCS1 | 1.28 | 1.9 |
| AATF | 1.28 | 2.6 |
| MEIS2 | 1.28 | 4.5 |
| CCNG2 | 1.28 | 14.8 |
| ANXA11 | 1.28 | 1.1 |
| DDAH2 | 1.28 | 11.1 |
| SLFN13 | 1.28 | 3.5 |
| LCP1 | 1.27 | 14.8 |
| SERP1 | 1.27 | 0.5 |
| TSPAN9 | 1.27 | 11.1 |
| MKX | 1.27 | 1.4 |
| ZNF436 | 1.27 | 3.5 |
| SEC11A | 1.27 | 4.5 |
| SH3GL1 | 1.27 | 8.2 |
| CD58 | 1.27 | 6.0 |
| ENO1 | 1.27 | 11.1 |
| PHGDH | 1.26 | 11.1 |
| ANGPT2 | 1.26 | 8.2 |
| KIAA1217 | 1.26 | 1.4 |
| DIP2C | 1.26 | 8.2 |
| ACCN1 | 1.26 | 6.0 |
| SOCS5 | 1.26 | 0.8 |
| IGF2R | 1.26 | 6.0 |
| CSK | 1.26 | 4.5 |
| ADCY6 | 1.26 | 8.2 |
| TSC22D4 | 1.26 | 14.8 |
| C7orf10 | 1.26 | 6.0 |
| HIPK2 | 1.25 | 11.1 |
| FAIM3 | 1.25 | 6.0 |
| FAM135A | 1.25 | 6.0 |
| SERAC1 | 1.25 | 2.6 |
| CRK | 1.25 | 14.8 |
| CACNA1C | 1.25 | 3.5 |
| ARID5A | 1.25 | 8.2 |
| EMD | 1.25 | 6.0 |
| INADL | 1.25 | 8.2 |
| F13A1 | 1.24 | 14.8 |
| DNAJC15 | 1.24 | 8.2 |
| STON1 | 1.24 | 14.8 |
| AMOT | 1.24 | 2.6 |
| INTS7 | 1.24 | 4.5 |
| FAM70A | 1.24 | 14.8 |
| COL9A2 | 1.23 | 14.8 |
| HMBOX1 | 1.23 | 11.1 |
| ZFR | 1.23 | 14.8 |
| RALA | 1.23 | 8.2 |
| EVI1 | 1.23 | 1.9 |
| SOAT1 | 1.23 | 11.1 |
| FOXP4 | 1.23 | 14.8 |
| TGFA | 1.23 | 0.8 |
| OSBPL6 | 1.23 | 11.1 |
| SKAP2 | 1.23 | 6.0 |
| SNX2 | 1.23 | 8.2 |
| HES2 | 1.23 | 11.1 |
| SBF2 | 1.23 | 2.6 |
| DCLK1 | 1.22 | 8.2 |
| MCTP1 | 1.22 | 4.5 |
| SLC35F3 | 1.22 | 11.1 |
| PLD1 | 1.22 | 11.1 |
| UAP1L1 | 1.22 | 14.8 |
| PTP4A2 | 1.22 | 8.2 |
| MAP6 | 1.22 | 14.8 |
| SLC10A7 | 1.21 | 2.6 |
| UNC5B | 1.21 | 11.1 |
| GFRA1 | 1.21 | 8.2 |
| TMEM41A | 1.21 | 14.8 |
| C14orf101 | 1.21 | 11.1 |
| CBFA2T2 | 1.21 | 3.5 |
| FOSL2 | 1.21 | 2.6 |
| DYM | 1.21 | 6.0 |
| ABHD10 | 1.20 | 14.8 |
| PTPRJ | 1.20 | 8.2 |
| BPTF | 1.20 | 8.2 |
| C20orf194 | 1.20 | 6.0 |
| SLC35D1 | 1.20 | 14.8 |
| CTBS | 1.20 | 14.8 |

Figure 18C:
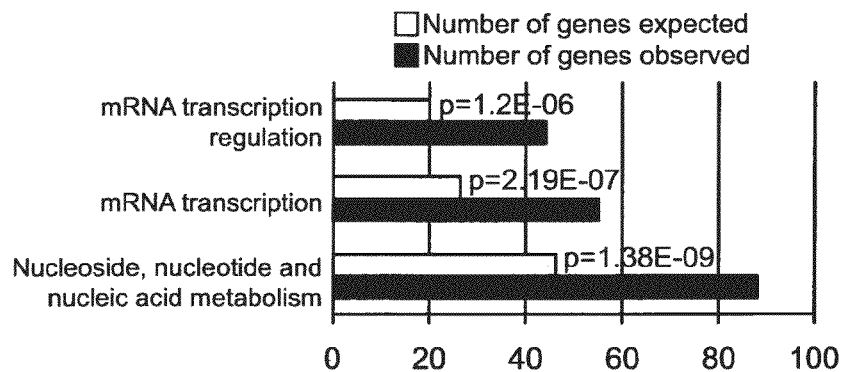
Figure 18D:
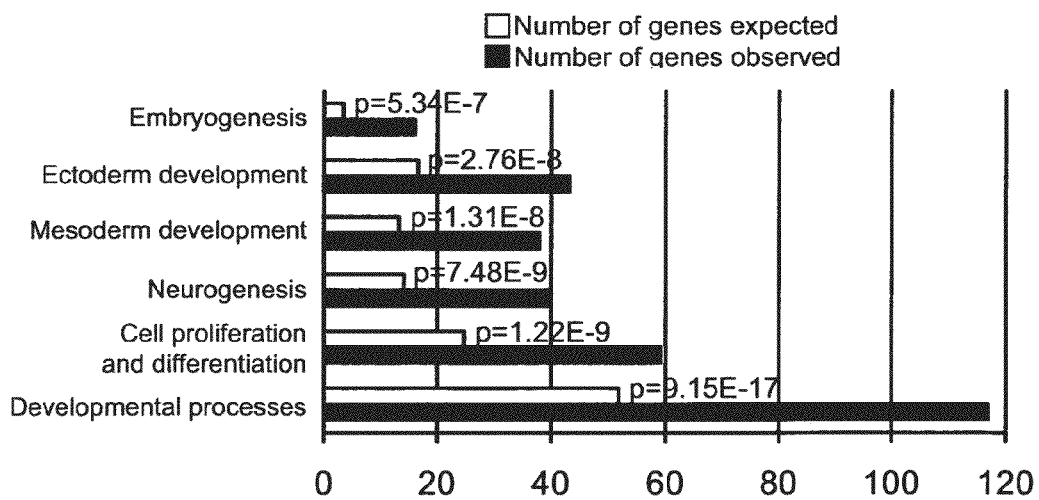
Figure 19A:
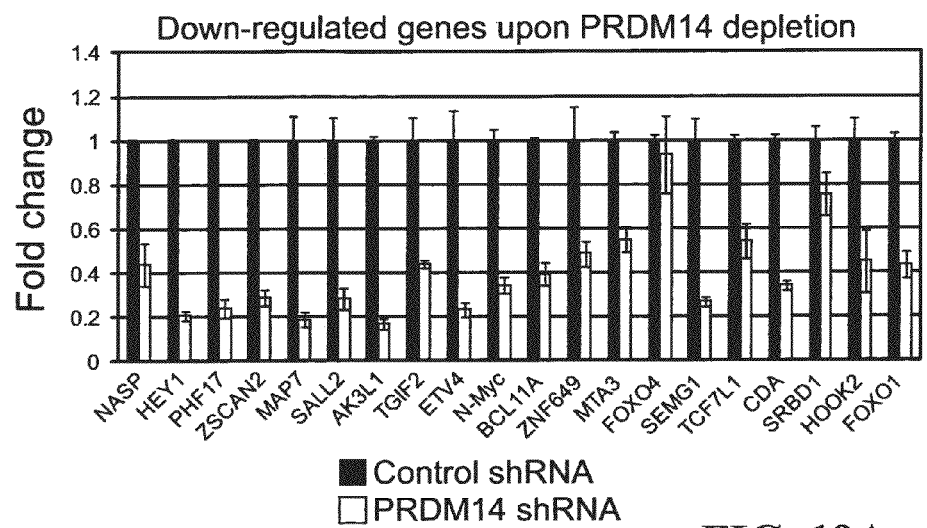
Figure 19B:
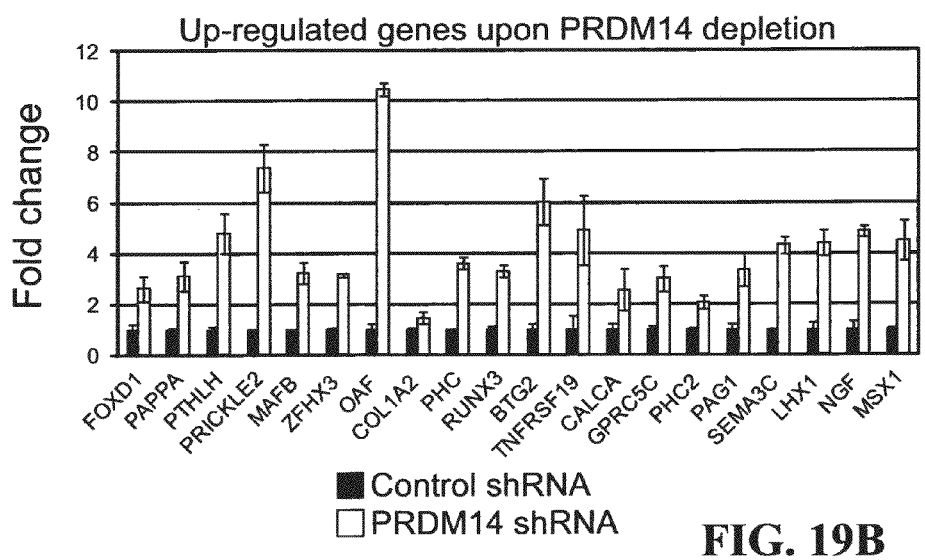

GO analysis of the PRDM14-activated genes showed that they are enriched for biological processes such as nucleic acid metabolism and mRNA transcription (FIGS. 18C and 19A). In contrast, GO analysis of PRDM14-repressed genes showed enrichment for GO categories such as developmental processes, neurogenesis, mesoderm development, ectoderm development and embryogenesis (FIGS. 18D and 19B). This finding suggests that PRDM14 can play both positive and negative roles on transcription.

Figures 20A, 20B:
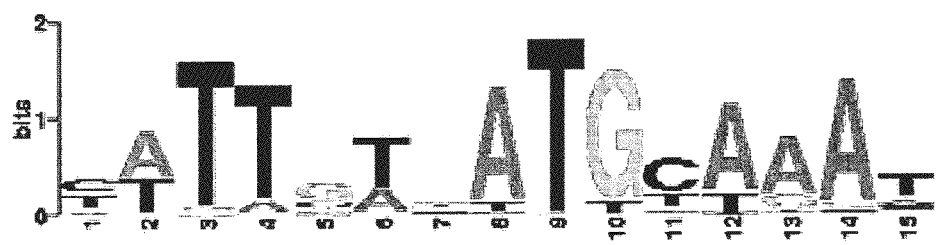

To investigate the other transcription factors that co-bind with PRDM14 at the PRDM14 regulated genes, 953 vertebrate position weight matrices (PWMs) were scanned for enrichment proximal to PRDM14 sites. An OCT4 PWM was among the top 20 significantly enriched PWMs (FIG. 20A).

Figure 20D:
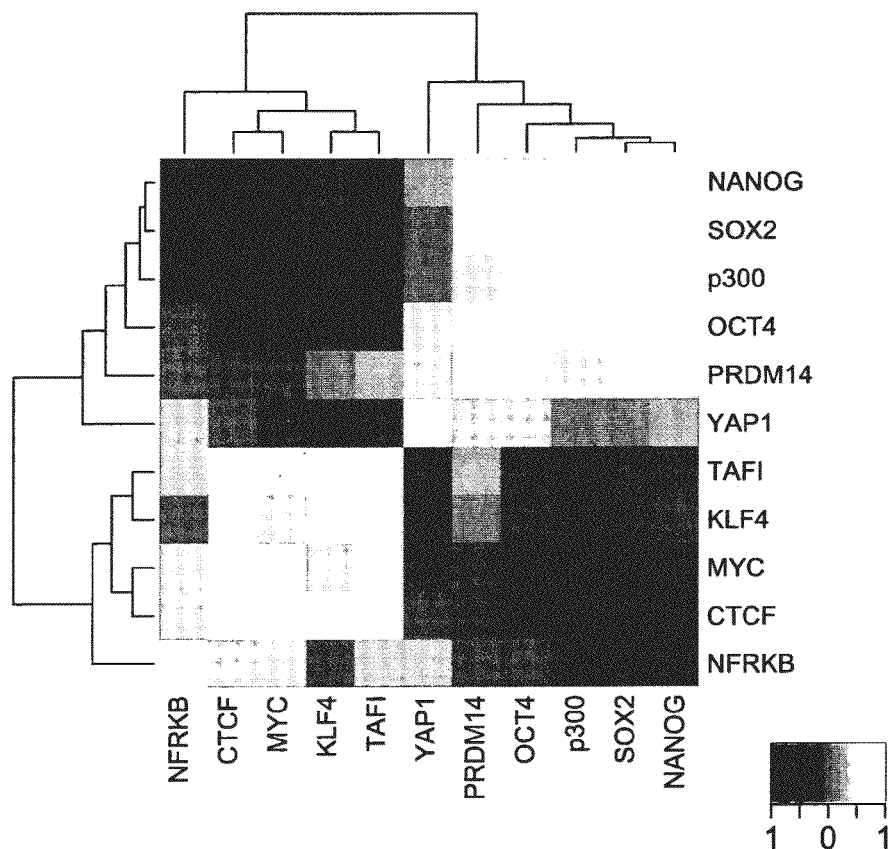

The OCT4 PWM, which is a joint Sox2 and Oct4 motif (FIG. 20B), was derived from previous ChIP-seq datasets for Oct4, Sox2 and Nanog in mouse ES cells. Of note, not all PWMs are enriched at PRDM14 sites (FIG. 20C). Next, co-localization analysis was performed with 10 other ChIP-seq datasets. Again, significant co-localization of PRDM14 with OCT4, SOX2 and NANOG was observed (FIG. 20D).

Figure 18E:
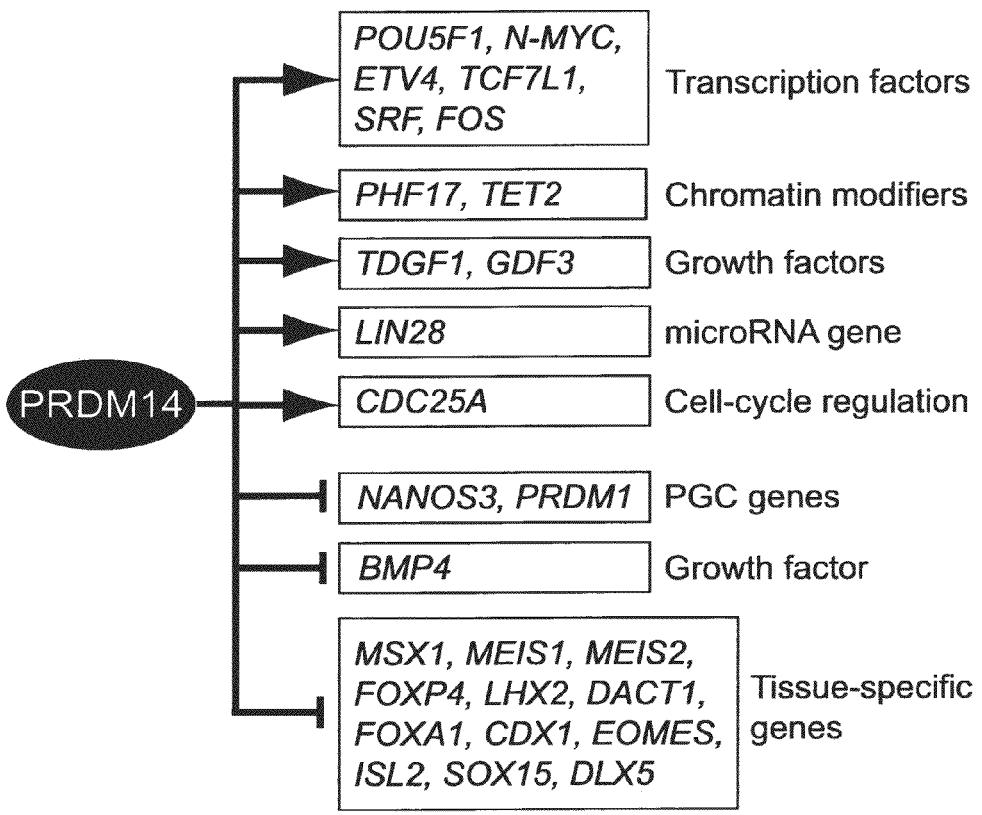

Hence, the genome-wide PRDM14 binding site profiling data and expression analysis unveiled that the target genes of PRDM14 are involved in diverse cellular processes. Genes coding for transcription factors (POU5F1, N-MYC, ETV4, TCF7L1), chromatin modifiers (TET2), growth factors (TDGF1, GDF3), microRNA biogenesis factor (LIN28) and cell cycle regulator (CDC25A) are positively regulated by PRDM14 (FIG. 18E). On the other hand, genes coding for tissue-specific transcription factors and certain growth factor (BMP4) are negatively regulated by PRDM14.

Figure 21A:
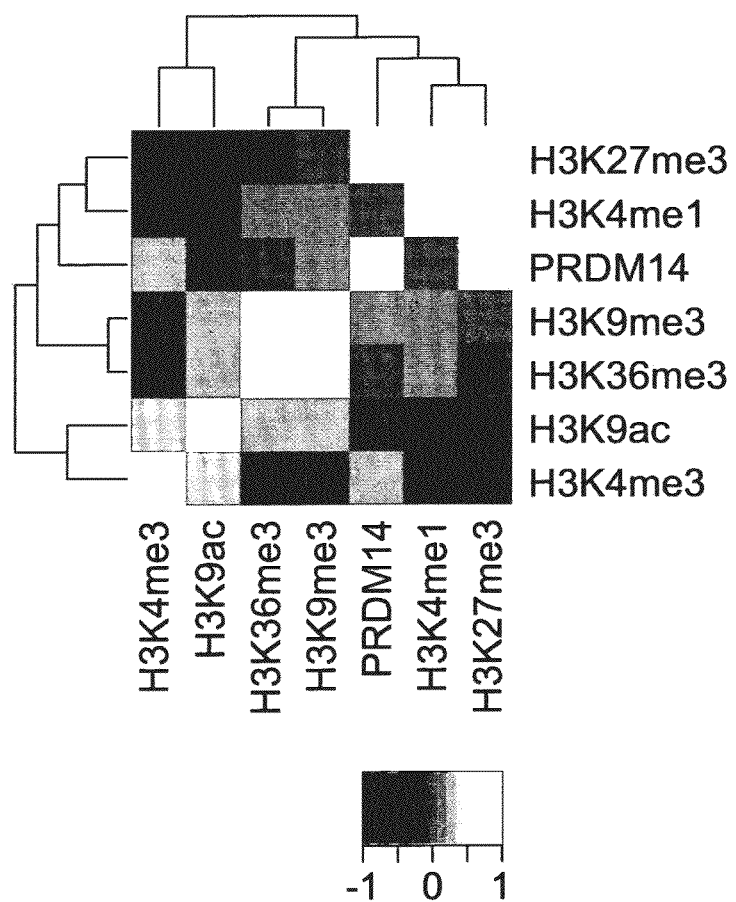
Figure 21B:
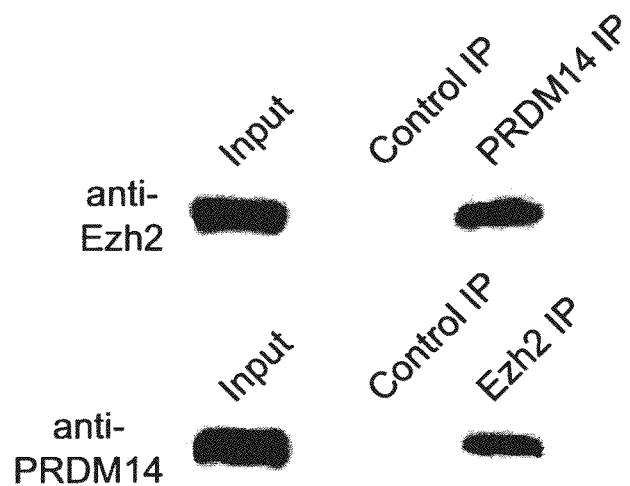
Figure 21C:
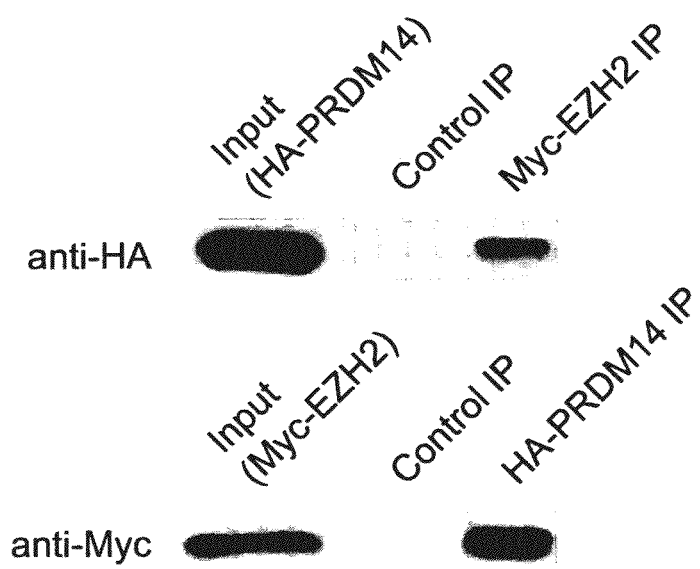
Figure 21D:
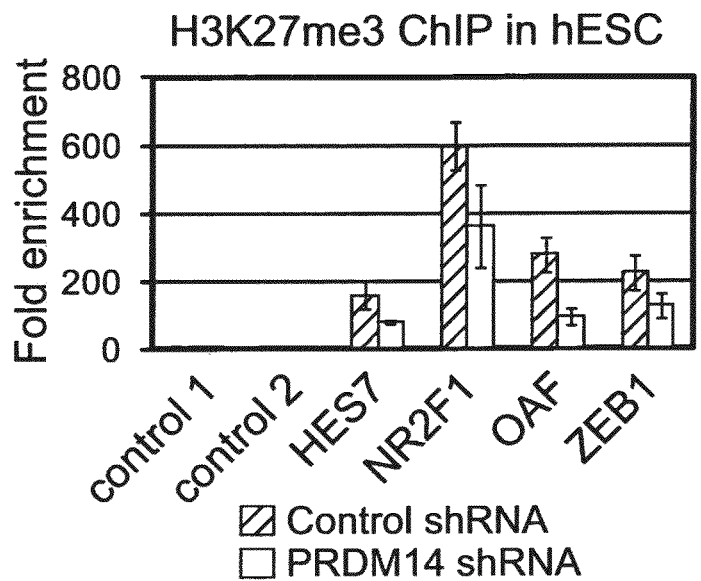
Figure 21E:
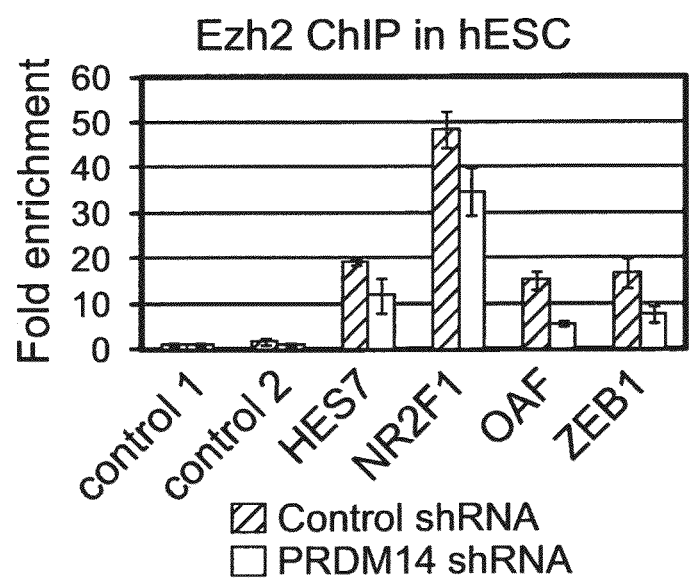
Figure 21F:
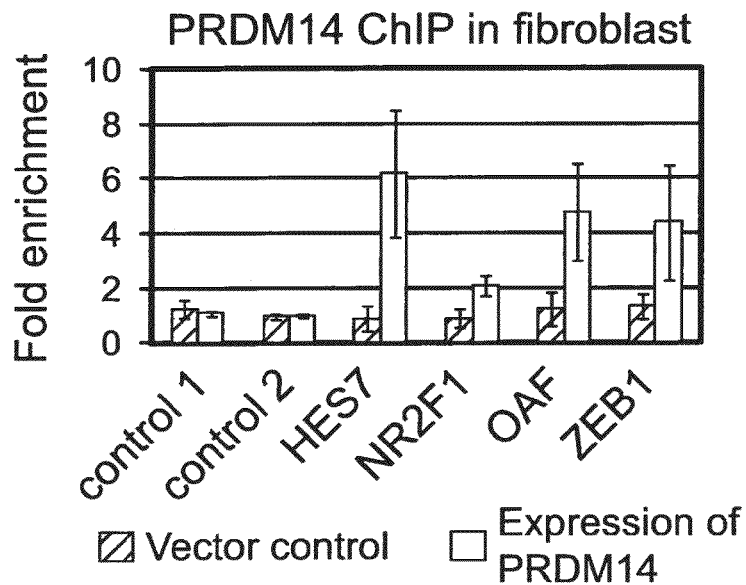
Figure 21G:
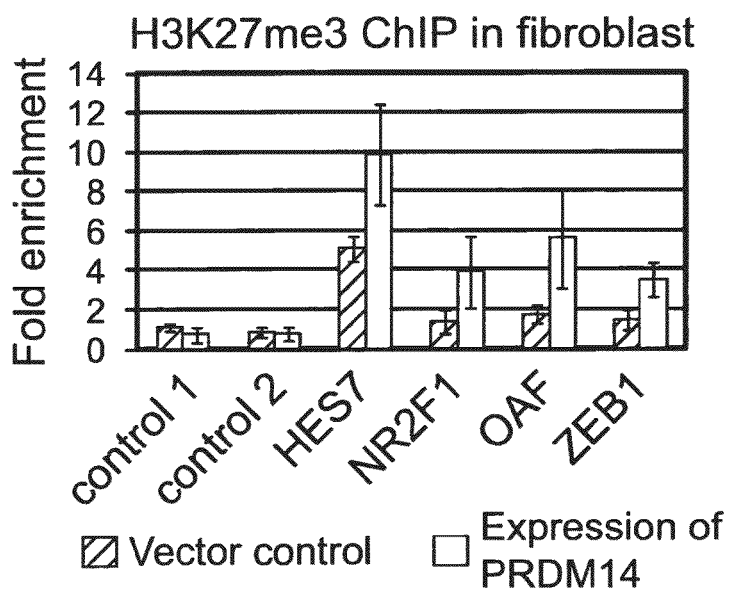
Figure 21H:
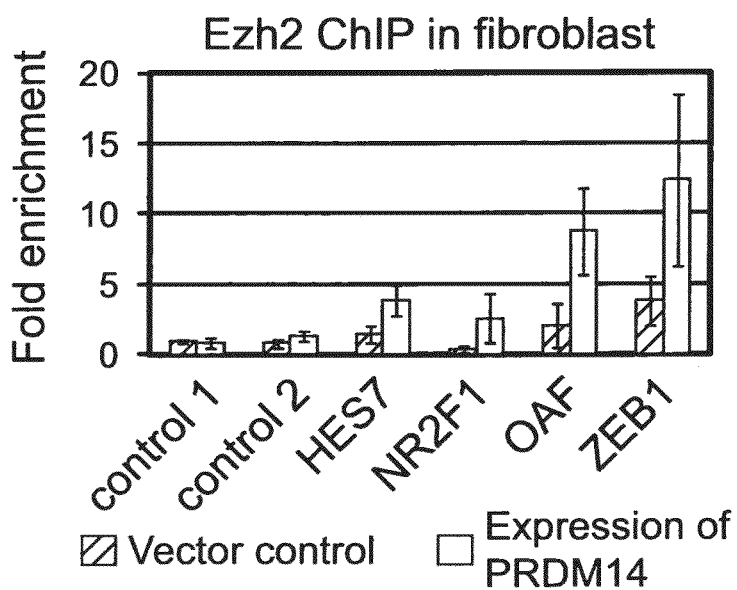
Figure 21I:
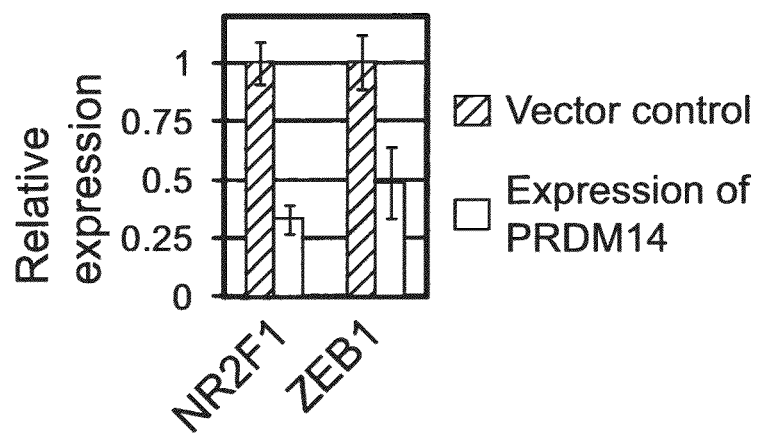
Figure 21J:
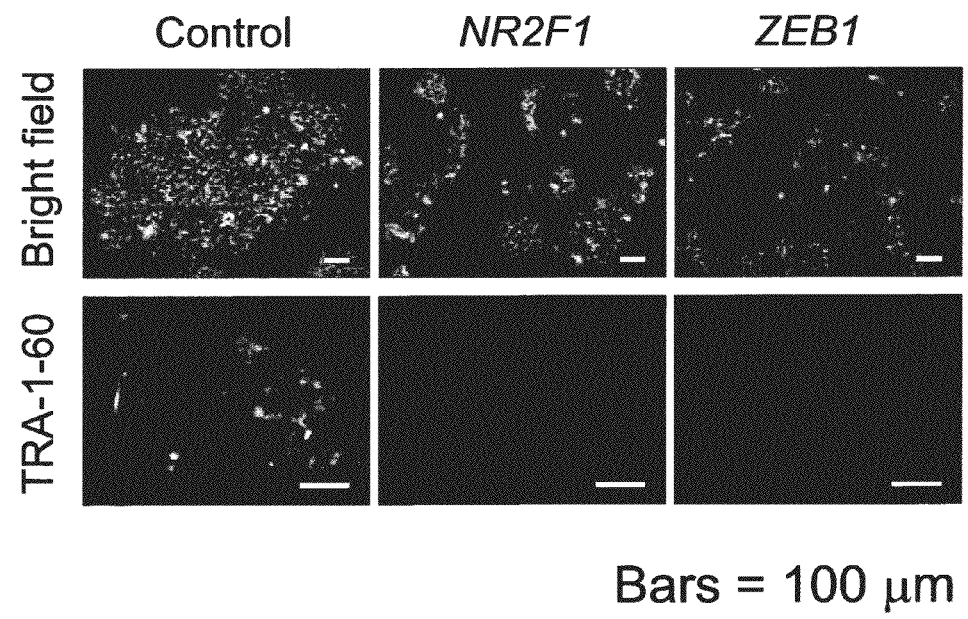

To further investigate the mechanism in which PRDM14 regulates transcription, the PRDM14 ChIP-seq data was analyzed with publicly available histone modification ChIP-seq datasets generated from hESC. Interestingly, co-occurrence of PRDM14 and H3K27me3, a histone mark associated with transcriptional repression, was observed (FIG. 21A). This raises the possibility that PRDM14 may recruit the polycomb repressive complex to mediate H3K27 methylation. Indeed, it was found that PRDM14 associates with Ezh2, a component of polycomb repressive complex 2 (FIGS. 21B and 21C). Upon depletion of PRDM14, the levels of H3K27me3 and Ezh2 at PRDM14 bound targets (HES7, NR2F1, OAF, ZEB1) were reduced (FIGS. 21D and 21E). As it has been shown here that PRDM14 has a role in the conversion of human fibroblasts into hiPSCs, the effect of expression of PRDM14 in human fibroblasts was examined. Ectopic expression of PRDM14 led to the induction of H3K27me3 and recruitment of Ezh2 to these PRDM14 targets (FIGS. 21F, 21G and 21H). NR2F1 and ZEB1 are highly expressed in fibroblasts, but these genes are silenced in hESCs. The expression of NF2F1 and ZEB1 were also downregulated by PRDM14 (FIG. 21I). As over-expression of these genes induced differentiation of hESCs (FIG. 21J), silencing of these genes in fibroblasts will be required for the conversion of somatic cells into iPSCs.

Together, the results demonstrate that PRDM14 can mediate the recruitment of polycomb group proteins in hESCs and fibroblasts.

Materials and Methods

Cell Culture and Generation of POU5F1-GFP Reporter Cell Line:

The hESC lines H1 (WA-01, passage 28), H9 (WA-09, passage 26), HES2 (ES-02, passage 79), HES3 (ES-03, passage 97) and H1 POU5F1-GFP reporter cells (passage 56) were used for the genome-wide RNAi screen [1, 59]. They were cultured feeder-free on matrigel (BD) [60]. Condition medium used for culturing hESCs contained 20% KO serum replacement, 1 mM L-glutamine, 1% non-essential amino acids and 0.1 mM 2-mercaptoethanol and an additional 8 ng/ml of basic fibroblast growth factor (Invitrogen) supplemented to the hESCs unconditioned medium. Medium was changed daily. The hESCs were subcultured with 1 mg/ml collagenase IV (Gibco) every 5-7 days.

A 3064 bp upstream region of human POU5F1 gene was cloned upstream of a GFP reporter gene into a N-EGFP plasmid with Geneticin (Gibco) drug selection marker. 2 µg of the POU5F1-GFP construct was transfected into the hESCs using 6 µl of Fugene (Roche). Drug resistant colonies appeared after 2 weeks of drug selection.

Transfection, Staining and Imaging in 384-Well Plates:

The 384-well plates (Grenier) were coated with 10 µl of matrigel for 30 mins at 37° C. before removing the excess matrigel. 5 µl of 500 nM pooled siRNAs (siGenome, Dharmacon) or 5 ul of 500 nM individual siRNAs were printed onto the plate and frozen at −20° C. before use. During reverse transfection, a master mix of 0.05 µl of Dharmafect1 (Dharmacon) transfection reagent and 4.95 µl of OptiMEM (Invitrogen) mix was added to siRNA plates and incubated for 20 mins. Subsequently, 3,000 cells in 40 µl of conditioned medium with 10 µM Rock inhibitor (Calbiochem) were seeded in each well. Reagents and cells were added to the plate using a multidrop (Thermoscientific) and the above mentioned volume refers to the amount added to each well.

For the genome-wide screen, the cells were fixed and stained after 4 days of transfection. Medium from the cells was replaced with 30 µl of 4% paraformaldehyde (Sigma). Cells were fixed for 15 mins before washing with PBS. Hoechst 3342 (1:10,000, Invitrogen) in 0.1% Triton-X/1% BSA was added to each well and stained for 30 mins. The cells were then washed once with PBS and covered in 30 µl of PBS.

Cells were imaged with IXU ultra confocal microscope (Research Instruments) at 20× magnification and 4 frames per well were taken. Integrated fluorescent intensity and number of nuclei were quantitated using MetaXpress Image Acquisition and Analysis software V1.7. Z' factor was calculated for the primary screen based on the formula $Z'=1-3(\sigma p+\sigma n)/(\mu p-\mu n)$ where $\sigma p$=standard deviation of the positive control, $\sigma n$=standard deviation of the negative control, $\mu p$=mean of the positive control and $\mu n$=mean of the negative controls. z-score was calculated using the formula $z=(X-\mu)/SD$ where g is the mean of the negative controls and SD is the standard deviation of the whole population. X is the sample value calculated based on the integrated fluorescent intensity/number of cells. For the secondary assays, the screen was carried out in duplicate for the different stemness marker of analysis in the 3 different hESCs (H1 GFP reporter line, HES2 and HES3). The average of the duplicate data was taken and the value was normalized to the wells transfected with non-targeting siRNA. The value for each well is a relative expression to that of the average of the negative control wells. The antibodies used for staining are OCT4 antibody (ab19857, Abcam, 0.6 mg/ml), NANOG antibody (AF1997, R&D), Alexa Fluor 647 anti-goat IgG and Alexa Fluor 594 anti-rabbit IgG (Invitrogen). All antibodies are added in the dilution of 1:600.

Informatics Analysis—Gene Ontology (GO) Analysis:

GO analysis was performed with Panther classification (www.pantherdb.org) for the molecular functions and biological processes.

Informatics Analysis—Reactome Analysis:

A web-resource Reactome (www.reactome.org) is used for the analysis of reactions and/or pathways that are statistically over-represented from the 566 genes with z-score>2 submitted. The Entrez gene ID of the hits were input as gene-identifiers using "sky-painter tool" which calculates a one-tailed. Fisher's exact test for the probability of observing at least N genes from an event if the event is not over-represented among the 566 genes. Events with p-value<0.05 are statistically significant and over-represented. These events are highlighted in the map with the accompanying genes listed.

Informatics Analysis—STRING Network Analysis:

Protein-protein interaction network is generated using STRING database which comprises a database of known and predicted protein interactions (http://string.embl.de/). 566 genes were input into STRING and 263 genes formed interactions among themselves. A medium confidence score criterion is set for the building of the protein network. Active prediction methods used are experiments, databases and text-mining. The resulting network is imported into cytoscape. Stem cells and transcription related genes based on Gene Ontology prediction are indicated in green in the cytoscape. The rest of the genes are indicated in pink. A high confidence score criterion is set for the individual protein complexes; INO80 complex, mediator complex, TAF complex, COP9 signalosome, eukaryotic initiation factor complex and spliceosome complex. Active prediction methods used for these smaller protein-protein network networks are the same as that for the 263 genes protein-protein network. The protein complexes are imported into pathway studio for further text-mining and additional interactions. Pathway studio highlights the entities that have a z-score of greater than 2 in red.

Informatics Analysis—Peak Calling:

Peak calling of the PRDM14 ChIP-seq data (12,824,267 uniquely mapped tags) was carried out using MACS [65] with a P value cutoff of 1e-10. 7,002 peaks were called. The control ChIP-seq library (sequencing of input DNA) contained 15,975,557 uniquely mapped tags.

Enriched sequence motifs were identified by de novo motif discovery programs Weeder, MEME [66] and CisFinder [53]. These programs identified the most overrepresented motif in PRDM14 ChIP-seq peak regions. All three programs identified a motif with the core 9-mer GGTCTCTAA as the most or second most enriched motif. The logo shown in FIG. 14B is an extended motif identified by CisFinder using as input the sequences of the top 2000 PRDM14 ChIP-seq peaks (peak summit+/−100 bp.). In running CisFinder, we applied clustering of the initial candidate motifs using a match threshold of 0.5.

A novel method was used for assessing the enrichment of known motif in ChIP-seq peaks based on the distribution of motif matches around the peak center (Chang et al., manuscript in preparation). Sequences around ChIP-seq peaks were scored using position weight matrices (PWM) from TRANSFAC 11.4 [67] and a match of the PWM to the sequence was recorded if the score exceeded the 99.99 percentile score as observed across the whole genome (this is equivalent to one match in 10 kbp). The distributions of such matches in a flanking region+/−5000 bp from the peak center were used to calculate a score which reflects the enrichment of the PWM in windows around the peak centers.

Co-occurrence analysis to study the overlap of PRDM14 with other transcription factors binding sites was performed as described previously [12]. CTCF, OCT4 and NANOG ChIP-seq datasets were generated and processed in the same way as the PRDM14 dataset. KLF4, MYC, p300, SOX2 and histone modifications ChIP-seq data were obtained from GEO (GSE18292, GSE17917 and GSE16256) [17]. Peak calling for these external ChIP-seq datasets was done using MACS with the same parameters and corresponding hESC sequencing background data. To avoid bias in background sequencing we used an in-house control sequencing library of the same tag length (25 nt). Gene ontology analysis was done using PANTHER DB [68].

Knockdown of Genes with shRNA Constructs:

Prior to transfection, cells were trypsinized for 30 secs at 37° C. Cells subcultured from one well of a 6-well dish were plated to nine wells one day in advance at 70% confluency. Individual shRNA for each gene were designed using WI siRNA selection program (http://jura.wi.mit.edu/bioc/siRNAext/). 1.5 µg of shRNA construct (pSuper, Oligoengine) and 4.5 µl of Fugene HD (Roche) were used for transfection. 0.8 µg/ml of puromycin was added to the condition medium 24 hrs after transfection. Cells were harvested for alkaline phosphatase staining (according to manufacturer's protocol) and RNA extraction was performed using Trizol (Invitrogen) after 4 days of knock down. 500 ng RNA was reverse transcribed using superscript II (Invitrogen) utilizing oligo $(dT)_{18}$ primer. mRNA expression changes were quantitated from qPCR using Kappa Sybr green enzyme. Measured transcript was normalized to GAPDH and samples were run in triplicate.

Immunofluorescence:

Human ESCs, iPSCs or differentiation culture were fixed with 4% paraformaldehyde in PBS. After permeablization in 1% triton X-100/PBS for 30 min, immunostaining was performed using the following primary antibodies: NANOG (AF1997, R&D system), OCT4 (ab19857, Abcam), TRA-1-60 (sc-21705, Santa Cruz), TRA-1-81 (sc-21706, Santa Cruz), SSEA-4 (sc-21704, Santa Cruz), NESTIN (ab5968, Abcam), cardiac actin (10R-C116a, Fitzgerald), SOX17 (sc-17355, Santa Cruz), $p57^{kip2}$ (RB-1637-P, Neomarkers), anti-α-Smooth Muscle Actin (ab18460, Abcam), RUNX1 (ab61753, Abcam), MAFB (sc-22830, Santa Cruz) and IGFBP5 (sc-6006, Santa Cruz). Secondary antibodies used are Alexa Fluor 488/546 anti-mouse IgM, and Alexa Fluor 488/546 anti-mouse or anti-rabbit IgG (Invitrogen). DAPI or Hoechst (Invitrogen) was used for staining the nuclei.

Teratoma Formation:

hESCs or hiPSCs were treated with type IV collagenase and resuspended in 0.9% normal saline at a concentration of $1 \times 10^7$ cells/ml. 100 µl of the cell suspension was injected into the dorsal flanks of SCID mice that were anesthetized with Avertin. Teratomas were formed after 6 to 8 weeks and they were surgically dissected, fixed in Bouin's solution and embedded in paraffin. They were sectioned and analyzed with Mallory's Tetrachrome staining.

Retroviral Production and Human iPSC Induction:

pMXs retroviral plasmids that carry cDNA of human OCT4, SOX2, KLF4 and c-MYC genes were obtained from Addgene (plasmids 17217, 17218, 17219 and 17220) [27]. cDNA of human PRDM14 gene was cloned into pMX vector for retrovirus mediated over-expression. Retroviruses were packaged using Pantropic Retroviral Expression System (Clontech) and concentrated with centrifugal filter devices (Millipore). MRC-5 cells obtained from ATCC were cultured in 15% FBS/DMEM. Confluent MRC-5 cells were split into 24 wells at one day before being transduced with equal amount of the retroviruses stock in presence of 4 µg/ml polybrene (Sigma). After 24 hours, the cells were changed to fresh 15% FBS/DMEM medium, and then split from a single 24-well into two 6-wells with pre-seeded CF-1 feeders in the next day. The cultures were then maintained in human ESC culture medium and fed every two days. To expand and characterize hiPSCs, each emerged hESC-like colony was mechanically dissociated to small clamps and transferred into one 6-well with CF-1 feeder.

In Vitro Differentiation:

For spontaneous differentiation through embryoid body formation, hiPSCs were dissociated by collagenase IV treatment and transferred to low attachment 10 cm dishes. After 1 week, embryoid bodies were transferred to gelatin-coated plates and cultured in the same medium for another 6 days. For growth factor-induced differentiation, hiPSCs were dissociated by collagenase IV treatment and seeded on Matrigel, then induced for definitive endoderm differentiation using 100 ng/ml Activin A [61], or for trophectoderm differentiation using 100 ng/ml BMP4 and 1 µM PD0325901 [62].

Karyotyping:

Cells were treated with colcemid for mitotic arrest and harvested by standard hypotonic treatment and methanol: acetic acid (3:1) fixation. Slides were prepared by standard air drying method and G-band karyotyping was performed.

Bisulfite Sequencing:

Bisulfite treatment of DNA was performed with the Imprint™ DNA Modification Kit (Sigma) according to manufacturer's instructions. Amplified products were cloned into the pGEM-T easy vector (Promega), and sequenced with M13 forward and reverse primers.

Primers used for amplifying POU5F1 promoter are:

```
                                         (SEQ ID NO: 7)
5'-ATTTGTTTTTTGGGTAGTTAAAGGTTG;

(SEQ ID NO: 8)
5'-ACCAACTATCTTCATCTTAATAACATCCA [63].
```

Primers used for amplifying NANOG promoter are:

```
                                         (SEQ ID NO: 9)
5'-TGGTTAGGTTGGTTTTAAATTTTTG;

(SEQ ID NO: 10)
5'-AACCCACCCTTATAAATTCTCAATTA [63].
```

Genotyping:

PCR amplification was carried out using 500 ng of genomic DNA extracted from MRC-5, H1 hESC and reprogrammed cells for each reaction.

Sense primer used for amplifying:

```
                                         (SEQ ID NO: 11)
5'-GACGGCATCGCAGCTTGGATACAC
```

Antisense primers used for amplifying

```
PRDM14:
                                         (SEQ ID NO: 12)
5'-TCGTAGAGAGGCTCCCTCTGTAGGC

OCT4:
                                         (SEQ ID NO: 13)
5'-CAGGTCCGAGGATCAACCCAGC

SOX2:
                                         (SEQ ID NO: 14)
5'-GGGTTCTCCTGGGCCATCTTGC

KLF4:
                                         (SEQ ID NO: 15)
5'-TCCCGCCAGCGGTTATTCGG c-MYC:
                                         (SEQ ID NO: 16)
5'-CCTCCTCGTCGCAGTAGAAATACGG

NFRKB:
                                         (SEQ ID NO: 17)
5'-GCAGAAACTGCTGGAGGTGTTCACG
```

Western Analysis:

After 48 h transfection, 293-T cells were lysed with RIPA buffer (Pierce) supplemented with protease inhibitor cocktail (Roche). Protein concentration was measured with a Bradford assay kit (Bio-Rad). 50 μg of cell lysate was resolved on a 10% SDS-polyacrylamide gel and transferred to a polyvinylidine difluoride membrane (Millipore). The membrane was blocked with 5% skim milk. After blocking, the blot was incubated with either anti-PRDM14 (1:2000, Home-made), anti-Oct4 (1:5000, Abcam), anti-Nanog (1:800, R&D) or anti-Gapdh (1:5000, Santa-Cruz) primary antibodies for 1 h, washed with PBST and incubated with either horse-radish peroxidase (HRP)-conjugated anti-rabbit IgG (1:5000, Santa Cruz), HRP-conjugated anti-goat IgG (1:5000, Santa Cruz) or HRP-conjugated anti-mouse IgG (1:5000, Santa Cruz), respectively. After washing with PBST, signals were detected using the Western Blotting Luminol Reagents (Santa Cruz).

Reporter Assays:

A minimal pou5f1 proximal promoter region (350 bp) was cloned into the PGL3 basic vector (Promega), driving the luciferase gene via the cloning site BglII and NcoI. The CR2 and CR4 fragments (550 and 500 bp, respectively) were cloned into the PGL3-Pou5f1 pp vector downstream of the luciferase gene via the cloning sites BamHI and SalI. For the cloning of reporter vector used to test the functional domains of PRDM14, 3 copies of 30 bp CR2 consensus motif was synthesized and cloned into XhoI and BglII site in front of the minimal promoter of pGL4.23 vector (Promega) in tandem. H1, HES2 and HES3 hESCs were transfected with the reporter constructs using Fugene (Roche) and E14 mESCs and 293T cells using Lipofectamine 2000 (Invitrogen). Cells were harvested 48-60 hrs after transfection and the luciferase activities were quantified using the Dual-luciferase Reporter Assay System (Promega).

Electrophorectic Mobility Shift Assay:

Recombinant PRDM14 DNA binding domain (His tagged) was used in the gel shift assays. Briefly, a cDNA encoding 179 amino acids of the C terminus of PRDM14 was cloned into the pET42b (Novagen) vector using cloning sites NdeI and XhoI. The fusion construct was transformed into BL21 competent cells (Strategene) according to the supplier's instructions. Purified proteins were dialyzed against a dialysis buffer (10 mM Tris-HCl, pH 7.4, 100 mM NaCl, 10 mM $ZnCl_2$ and 10% glycerol) at 4° C. for 6 hr. Oligonucleotides (Proligo) labeled with biotin at the 5' end of the sense strands were annealed with the antisense strands in the annealing buffer (10 mM Tris-HCl, pH8.0, 50 mM NaCl, 1 mM EDTA) and purified with agarose gel DNA extraction kit (Qiagen). DNA concentrations were determined by the NanoDrop ND-1000 spectrophotometer. The gel shift assays were performed using a LightShift Chemiluminescent EMSA kit (Pierce Biotechnologies). 100 ng of protein was added to a 5 μl reaction mixture (final) containing 1 μg of poly(dI-dC) (Amersham), 1 ng of biotin-labeled oligonucleotide in the binding buffer (12 mM HEPES, pH7.9, 10% glycerol, 60 mM KCl, 0.25 mM EDTA, 1 mM DTT, 10 mM $ZnCl_2$). Binding reaction mixtures were incubated for 20 min at room temperature. Binding reaction mixtures were resolved on pre-run 6% native polyacrylamide gels in 0.5× Tris-buffered EDTA ($1^{st}$ Base). Gels were transferred to Biodyne B nylon membranes (Pierce Biotechnologies) using western blot techniques and detected using chemiluminescence. Probe sequences for FIGS. 14D and 14E:

```
CR2 probe:
                                         (SEQ ID NO: 18)
CAGCTCTAACCCTAAACAAGTGCTCAACCCTTGAATGGGCCTGGATGGCT CR2 Mutant:
                                         (SEQ ID NO: 19)
CATTTTTAACCCTAAACAAGTTTTTAACCCTTGAATGGGCCTGGATGGCT
```

ChIP assay. ChIP assays were performed as described previously [64]. In short, cells were crosslinked with 1% formaldehyde for 10 min at room temperature and the formaldehyde was quenched with 125 mM glycine. Cell lysates were sonicated and chromatin extracts were immunoprecipitated by using the respective antibodies. Quantitative PCR analyses were performed as previously described.

Microarray Analysis:

mRNAs derived from hESCs, hiPSCs and human MRC-5 fibroblasts were reverse transcribed, labeled and analyzed on Illumina microarray platform (HumanRef-8 v3.0 Expression BeadChips). Arrays were processed according to manufacturer's instructions. For each cell type or cell line, biological replicate microarray data were generated. Rank invariant normalization was used to normalize the microarrays. For PRDM14 knockdown, mRNAs derived from PRDM14 shRNA and luciferase shRNA-treated H1 hESCs were reverse transcribed, labeled and similarly analyzed on Illumina microarray platform (HumanRef-8_v3.0 Expression BeadChips). Biological triplicates were included in the profiling of PRDM14-depleted H1 cells. Cluster 3.0 was used for hierarchical clustering and Java Treeview for visualization.

PRDM14 associated genes (data not shown) were defined by PRDM14 ChIP-seq peak location in +/−20 Kbp distance to RefSeq gene borders (either to 5' or 3' end) or in gene. 2,645 genes of 2,755 PRDM14 associated genes were presented on Illumina microarray platform. SAM software [69] was used to define sets of gene up- and down-regulated genes in triplicate data on gene expression in hESC after PRDM14 siRNA knockdown. A 1.2 fold change threshold and q-values less than 15% were used to detect differentially expressed genes: 358 RefSeq genes were defined as down-regulated and 638 RefSeq genes as up-regulated at 3 days after PRDM14 knockdown (see Tables 6 and 7, above); FIGS. 18A and 18B).

1,458 PRDM14 sites (ChIP-seq peaks) associated with 996 PRDM14 regulated genes (+/−20 Kb to the gene borders) were analyzed for co-occurring PWMs found in the TRANSFAC database (158 transcription factor families with 953 vertebrate PWM) (FIG. 20). The frequency of these TRANSFAC PWM occurring within 200 bp from these PRDM14 sites were counted. The p-values were calculated with statistics of binomial distribution using StatXact software.

Co-Immunoprecipitation:

H1 hESCs and transfected 293T cells were lysed in the cell lysis buffer (50 mM Tris-HCl, pH 8.0, 150 mM NaCl, 10 uM ZnCl, 0.5% Nonidet P-40, 5% glycerol with protease inhibitor) for 1 h. The whole cell lysate was precleared, collected and incubated overnight with beads coated with antibodies at 4° C. The beads were washed 4 times with the cell lysis buffer and boiled 10 mins for elution. The interacting protein bands are resolved with 10% SDS-PAGE gel and transferred to the PVDF membrane, followed by detection with an appropriate primary antibody, an HRP-conjugated second antibody, and an ECL reagent. Antibodies used in Co-IP: Anti-GST (sc-469, Santa Cruz), anti-PRDM14 (custom-made), anti-NANOG (AF1997, R&D), anti-HA (sc-7392, Santa Cruz), anti-cMyc (sc-40, Santa Cruz) and anti-EZH2 (Active motif) antibodies were used to pull down the protein complexes.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

As used in this specification and the appended claims, the singular forms "a," "an," and "the" include plural reference unless the context clearly dictates otherwise. Unless defined otherwise all technical and scientific terms used herein have the same meaning as commonly understood to one of ordinary skill in the art to which this invention belongs.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

REFERENCES

1. Thomson, J. A. et al. Embryonic stem cell lines derived from human blastocysts. *Science* 282, 1145-7 (1998).
2. Evans, M. J. & Kaufman, M. H. Establishment in culture of pluripotential cells from mouse embryos. *Nature* 292, 154-6 (1981).
3. Martin, G. R. Isolation of a pluripotent cell line from early mouse embryos cultured in medium conditioned by teratocarcinoma stem cells. *Proc Natl Acad Sci USA* 78, 7634-8 (1981).
4. Yu, J. & Thomson, J. A. Pluripotent stem cell lines. *Genes Dev* 22, 1987-97 (2008).
5. Wei, C. L. et al. Transcriptome profiling of human and murine ESCs identifies divergent paths required to maintain the stem cell state. *Stem Cells* 23, 166-85 (2005).
6. Sun, Y. et al. Cross-species transcriptional profiles establish a functional portrait of embryonic stem cells. *Genomics* 89, 22-35 (2007).
7. Kim, J., Chu, J., Shen, X., Wang, J. & Orkin, S. H. An extended transcriptional network for pluripotency of embryonic stem cells. *Cell* 132, 1049-61 (2008).
8. Boyer, L. A. et al. Core transcriptional regulatory circuitry in human embryonic stem cells. *Cell* 122, 947-56 (2005).
9. Chen, X. et al. Integration of external signaling pathways with the core transcriptional network in embryonic stem cells. *Cell* 133, 1106-17 (2008).
10. Scholer, H. R., Ruppert, S., Suzuki, N., Chowdhury, K. & Gruss, P. New type of POU domain in germ line-specific protein Oct-4. *Nature* 344, 435-9 (1990).
11. Chambers, I. et al. Nanog safeguards pluripotency and mediates germline development. *Nature* 450, 1230-4 (2007).
12. Scholer, H. R., Dressler, G. R., Balling, R., Rohdewohld, H. & Gruss, P. Oct-4: a germline-specific transcription factor mapping to the mouse t-complex. *EMBO J* 9, 2185-95 (1990).
13. Mitsui, K. et al. The homeoprotein Nanog is required for maintenance of pluripotency in mouse epiblast and ES cells. *Cell* 113, 631-42 (2003).
14. Niwa, H., Miyazaki, J. & Smith, A. G. Quantitative expression of Oct-3/4 defines differentiation, dedifferentiation or self-renewal of ES cells. *Nat Genet* 24, 372-6 (2000).
15. Chambers, I. et al. Functional expression cloning of Nanog, a pluripotency sustaining factor in embryonic stem cells. *Cell* 113, 643-55 (2003).
16. Heintzman, N. D. et al. Histone modifications at human enhancers reflect global cell-type-specific gene expression. *Nature* 459, 108-12 (2009).
17. Lister, R. et al. Human DNA methylomes at base resolution show widespread epigenomic differences. *Nature* 462, 315-22 (2009).
18. Ying, Q. L. et al. The ground state of embryonic stem cell self-renewal. *Nature* 453, 519-23 (2008).

19. Xu, R. H. et al. NANOG is a direct target of TGFbeta/activin-mediated SMAD signaling in human ESCs. *Cell Stem Cell* 3, 196-206 (2008).
20. Vallier, L. et al. Signaling pathways controlling pluripotency and early cell fate decisions of human induced pluripotent stem cells. *Stem Cells* 27, 2655-66 (2009).
21. Brons, I. G. et al. Derivation of pluripotent epiblast stem cells from mammalian embryos. *Nature* 448, 191-5 (2007).
22. Tesar, P. J. et al. New cell lines from mouse epiblast share defining features with human embryonic stem cells. *Nature* 448, 196-9 (2007).
23. Ding, L. et al. A genome-scale RNAi screen for Oct4 modulators defines a role of the Paf1 complex for embryonic stem cell identity. *Cell Stem Cell* 4, 403-15 (2009).
24. Ivanova, N. et al. Dissecting self-renewal in stem cells with RNA interference. *Nature* 442, 533-8 (2006).
25. Hu, G. et al. A genome-wide RNAi screen identifies a new transcriptional module required for self-renewal. *Genes Dev* 23, 837-48 (2009).
26. Fazzio, T. G., Huff, J. T. & Panning, B. An RNAi screen of chromatin proteins identifies Tip60-p400 as a regulator of embryonic stem cell identity. *Cell* 134, 162-74 (2008).
27. Takahashi, K. et al. Induction of pluripotent stem cells from adult human fibroblasts by defined factors. *Cell* 131, 861-72 (2007).
28. Park, I. H. et al. Disease-specific induced pluripotent stem cells. *Cell* 134, 877-86 (2008).
29. Dimos, J. T. et al. Induced pluripotent stem cells generated from patients with ALS can be differentiated into motor neurons. *Science* 321, 1218-21 (2008).
30. Raya, A. et al. Disease-corrected haematopoietic progenitors from Fanconi anaemia induced pluripotent stem cells. *Nature* 460, 53-9 (2009).
31. Maehr, R. et al. Generation of pluripotent stem cells from patients with type 1 diabetes. *Proc Natl Acad Sci USA* 106, 15768-73 (2009).
32. Chew, J. L. et al. Reciprocal transcriptional regulation of Pou5f1 and Sox2 via the Oct4/Sox2 complex in embryonic stem cells. *Mol Cell Biol* 25, 6031-46 (2005).
33. Watanabe, K. et al. A ROCK inhibitor permits survival of dissociated human embryonic stem cells. *Nat Biotechnol* 25, 681-6 (2007).
34. Joshi-Tope, G. et al. Reactome: a knowledgebase of biological pathways. *Nucleic Acids Res* 33, D428-32 (2005).
35. Conaway, R. C. & Conaway, J. W. The INO80 chromatin remodeling complex in transcription, replication and repair. *Trends Biochem Sci* 34, 71-7 (2009).
36. Casamassimi, A. & Napoli, C. Mediator complexes and eukaryotic transcription regulation: an overview. *Biochimie* 89, 1439-46 (2007).
37. Chamovitz, D. A. Revisiting the COP9 signalosome as a transcriptional regulator. *EMBO Rep* 10, 352-8 (2009).
38. Albright, S. R. & Tjian, R. TAFs revisited: more data reveal new twists and confirm old ideas. *Gene* 242, 1-13 (2000).
39. Jackson; R. J., Hellen, C. U. & Pestova, T. V. The mechanism of eukaryotic translation initiation and principles of its regulation. *Nat Rev Mol Cell Biol* 11, 113-27.
40. Rino, J. & Carmo-Fonseca, M. The spliceosome: a self-organized macromolecular machine in the nucleus? *Trends Cell Biol* 19, 375-84 (2009).
41. Takahashi, K. & Yamanaka, S. Induction of pluripotent stem cells from mouse embryonic and adult fibroblast cultures by defined factors. *Cell* 126, 663-76 (2006).
42. Park, I. H. et al. Reprogramming of human somatic cells to pluripotency with defined factors. *Nature* 451, 141-6 (2008).
43. Lowry, W. E. et al. Generation of human induced pluripotent stem cells from dermal fibroblasts. *Proc Natl Acad Sci USA* 105, 2883-8 (2008).
44. Yu, J. et al. Induced pluripotent stem cell lines derived from human somatic cells. *Science* 318, 1917-20 (2007).
45. Zhao, Y. et al. Two supporting factors greatly improve the efficiency of human iPSC generation. *Cell Stem Cell* 3, 475-9 (2008).
46. Tsubooka, N. et al. Roles of Sall4 in the generation of pluripotent stem cells from blastocysts and fibroblasts. *Genes Cells* 14, 683-94 (2009).
47. Nakagawa, M. et al. Generation of induced pluripotent stem cells without Myc from mouse and human fibroblasts. *Nat Biotechnol* 26, 101-6 (2008).
48. Assou, S. et al. A meta-analysis of human embryonic stem cells transcriptome integrated into a web-based expression atlas. *Stem Cells* 25, 961-73 (2007).
49. Tsuneyoshi, N. et al. PRDM14 suppresses expression of differentiation marker genes in human embryonic stem cells. *Biochem Biophys Res Commun* 367, 899-905 (2008).
50. Huang, S. Histone methyltransferases, diet nutrients and tumour suppressors. *Nat Rev Cancer* 2, 469-76 (2002).
51. Derunes, C. et al. Characterization of the PR domain of RIZ1 histone methyltransferase. *Biochem Biophys Res Commun* 333, 925-34 (2005).
52. Yamaji, M. et al. Critical function of Prdm14 for the establishment of the germ cell lineage in mice. *Nat Genet* 40, 1016-22 (2008).
53. Sharov, A. A. & Ko, M. S. Exhaustive search for overrepresented DNA sequence motifs with CisFinder. *DNA Res* 16, 261-73 (2009).
54. Hanna, J. et al. Metastable pluripotent states in NOD-mouse-derived ESCs. *Cell Stem Cell* 4, 513-24 (2009).
55. Nordhoff, V. et al. Comparative analysis of human, bovine, and murine Oct-4 upstream promoter sequences. *Mamm Genome* 12, 309-17 (2001).
56. Yeom, Y. I. et al. Germline regulatory element of Oct-4 specific for the totipotent cycle of embryonal cells. *Development* 122, 881-94 (1996).
57. Nichols, J. et al. Formation of pluripotent stem cells in the mammalian embryo depends on the POU transcription factor Oct4. *Cell* 95, 379-91 (1998).
58. Silva, J. et al. Nanog is the gateway to the pluripotent ground state. *Cell* 138, 722-37 (2009).
59. Richards, M., et al. The transcriptome profile of human embryonic stem cells as defined by SAGE. *Stem Cells* 22, 51-64 (2004).
60. Xu, C., et al. Feeder-free growth of undifferentiated human embryonic stem cells. *Nat Biotechnol* 19, 971-4 (2001).
61. D'Amour, K. A., et al. Efficient differentiation of human embryonic stem cells to definitive endoderm. *Nat Biotechnol* 23, 1534-41 (2005).
62. Xu, R. H., et al. BMP4 initiates human embryonic stem cell differentiation to trophoblast. *Nat Biotechnol* 20, 1261-4 (2002).
63. Hockemeyer, D., et al. A drug-inducible system for direct reprogramming of human somatic cells to pluripotency. *Cell Stem Cell* 3, 346-53 (2008).
64. Loh, Y. H., et al. The Oct4 and Nanog transcription network regulates pluripotency in mouse embryonic stem cells. *Nat Genet* 38, 431-40 (2006).
65. Zhang, Y., et al. Model-based analysis of ChIP-Seq (MACS). *Genome Biol* 9, R137 (2008).
66. Bailey, T. L., et al. MEME SUITE: tools for motif discovery and searching. *Nucleic Acids Res* 37(Web Server issue), W202-8 (2009).

67. Matys, V., et al. TRANSFAC and its module TRANSCompel: transcriptional gene regulation in eukaryotes. *Nucleic Acids Res* 34(Database issue), D108-10 (2006).
68. Mi, H., et al. The PANTHER database of protein families, subfamilies, functions and pathways. *Nucleic Acids Res* 33(Database issue), D284-8 (2005).
69. Tusher, V. G., Tibshirani R., and Chu G. Significance analysis of microarrays applied to the ionizing radiation response. *Proc Natl Acad Sci USA* 98, 5116-21 (2001).
70. Fumasoni, I., et al. Family expansion and gene rearrangements contributed to the functional specialization of PRDM genes in vertebrates. *BMC Evol Biol* 7, 187 (2007).
71. Takeda, J., Seino, S., and Bell, G. I. Human Oct3 gene family: cDNA sequences, alternative splicing, gene organization, chromosomal location, and expression at low levels in adult tissues. *Nucleic Acids Res* 20, 4613-20 (1992).
72. Bowles, J., Schepers, G. and Koopman, P. Phylogeny of the Sox family of developmental transcription factors based on sequence and structural indicators. *Dev Biol* 227, 239-55 (2000).
73. Ryan, A. K. and Rosenfield, M. G. POU domain family values: flexibility, partnerships, and developmental codes. *Genes & Dev* 11, 1207-25 (1997).
74. Wegner, M. From head to toes: the multiple facets of Sox proteins. *Nucleic Acid Res* 27, 1409-20 (1999).
75. Badis, G. et al. Diversity and complexity in DNA recognition by transcription factors. *Science* 324, 1720-3 (2009).
76. Evans, P. M., et al. Kruppel-like factor 4 is acetylated by p300 and regulates gene transcription via modulation of histone acetylation. *J Biol Chem* 10, 1074 (2007).
77. Adams, B. S., et al. Localization of the gene encoding R kappa B (NFRKB, a tissue-specific DNA binding protein, to chromosome 11q24-q25. *Genomics* 14, 270-4 (1992).

---

What is claimed is:

1. A method of inducing pluripotency in a human somatic cell, the method comprising: transducing the human somatic cell with one or more retroviral expression vectors encoding (i) OCT4 and SOX2; (ii) at least one of KLF4 and c-MYC; and (iii) NFRKB to thereby co-express the OCT4, SOX2, the at least one of KLF4 and c-MYC and the NFRKB in the human somatic cell; and culturing the human somatic cell in human embryonic stem cell culture medium in the presence of feeder cells to produce induced pluripotent stem cells.

2. The method of claim 1 wherein the one or more retroviral expression vectors encodes NFRKB, OCT4, SOX2 and KLF4.

3. The method of claim 2 wherein the one or more retroviral expression vectors also encodes c-MYC.

4. The method of claim 1 wherein the one or more retroviral expression vectors encodes NFRKB, OCT4, SOX2 and c-MYC.

5. The method of claim 1 wherein the human somatic cell is fully differentiated prior to said culturing.

6. The method of claim 1 wherein the human somatic cell is a human fibroblast prior to said culturing.

7. An isolated human somatic cell comprising one or more retroviral expression vectors encoding (i) OCT4 and SOX2; (ii) at least one of KLF4 and c-MYC; and (iii) NFRKB.

8. The isolated human somatic cell of claim 7, wherein the one or more retroviral expression vectors encodes OCT4, SOX2, KLF4 and NFRKB.

9. The isolated human somatic cell of claim 7, wherein the one or more retroviral expression vectors encodes OCT4, SOX2, c-MYC and NFRKB.

10. The isolated human somatic cell of claim 8, wherein the one or more retroviral expression vectors also encodes c-MYC.

11. The isolated human somatic cell of claim 7 in which pluripotency has been induced.

12. The isolated human somatic cell of claim 7, wherein said isolated human somatic cell is a fibroblast.

13. A method of maintaining pluripotency of a human embryonic stem cell (hESC) transduced with one or more retroviral expression vectors encoding (i) OCT4 and SOX2; (ii) at least one of KLF4 and c-MYC; and (iii) NFRKB, the method comprising: culturing the hESC in human embryonic stem cell culture medium in the presence of feeder cells to thereby co-express the OCT4, the SOX2, the at least one of KLF4 and c-MYC and the NFRKB in the hESC, wherein pluripotency is maintained in the hESC.

14. The method of claim 1 wherein the one or more retroviral expression vectors further encodes PRDM14.

15. The isolated human somatic cell of claim 7, wherein the one or more retroviral expression vectors further encodes PRDM14.

16. The method of claim 13 wherein the one or more retroviral expression vectors encodes NFRKB, OCT4, SOX2 and KLF4.

17. The method of claim 16 wherein the one or more retroviral expression vectors also encodes c-MYC.

18. The method of claim 13 wherein the one or more retroviral expression vectors encodes NFRKB, OCT4, SOX2 and c-MYC.

19. The method of claim 13 wherein the one or more retroviral expression vectors further encodes PRDM14.

* * * * *

SEQUENCE LISTING

```
<160> NUMBER OF SEQ ID NOS: 19

<210> SEQ ID NO 1
<211> LENGTH: 360
<212> TYPE: PRT
<213> ORGANISM: Homo sapiens

<400> SEQUENCE: 1

Met Ala Gly His Leu Ala Ser Asp Phe Ala Phe Ser Pro Pro Pro Gly
1               5                   10                  15

Gly Gly Gly Asp Gly Pro Gly Gly Pro Glu Pro Gly Trp Val Asp Pro
            20                  25                  30

Arg Thr Trp Leu Ser Phe Gln Gly Pro Pro Gly Gly Pro Gly Ile Gly
        35                  40                  45

Pro Gly Val Gly Pro Gly Ser Glu Val Trp Gly Ile Pro Pro Cys Pro
    50                  55                  60

Pro Pro Tyr Glu Phe Cys Gly Gly Met Ala Tyr Cys Gly Pro Gln Val
65                  70                  75                  80

Gly Val Gly Leu Val Pro Gln Gly Gly Leu Glu Thr Ser Gln Pro Glu
                85                  90                  95

Gly Glu Ala Gly Val Gly Val Glu Ser Asn Ser Asp Gly Ala Ser Pro
            100                 105                 110

Glu Pro Cys Thr Val Thr Pro Gly Ala Val Lys Leu Glu Lys Glu Lys
        115                 120                 125

Leu Glu Gln Asn Pro Glu Glu Ser Gln Asp Ile Lys Ala Leu Gln Lys
    130                 135                 140

Glu Leu Glu Gln Phe Ala Lys Leu Leu Lys Gln Lys Arg Ile Thr Leu
145                 150                 155                 160

Gly Tyr Thr Gln Ala Asp Val Gly Leu Thr Leu Gly Val Leu Phe Gly
                165                 170                 175

Lys Val Phe Ser Gln Thr Thr Ile Cys Arg Phe Glu Ala Leu Gln Leu
            180                 185                 190

Ser Phe Lys Asn Met Cys Lys Leu Arg Pro Leu Leu Gln Lys Trp Val
        195                 200                 205

Glu Glu Ala Asp Asn Asn Glu Asn Leu Gln Glu Ile Cys Lys Ala Glu
    210                 215                 220

Thr Leu Val Gln Ala Arg Lys Arg Lys Arg Thr Ser Ile Glu Asn Arg
225                 230                 235                 240

Val Arg Gly Asn Leu Glu Asn Leu Phe Leu Gln Cys Pro Lys Pro Thr
                245                 250                 255
```

```
Leu Gln Gln Ile Ser His Ile Ala Gln Gln Leu Gly Leu Glu Lys Asp
                260                 265                 270

Val Val Arg Val Trp Phe Cys Asn Arg Arg Gln Lys Gly Lys Arg Ser
            275                 280                 285

Ser Ser Asp Tyr Ala Gln Arg Glu Asp Phe Glu Ala Ala Gly Ser Pro
        290                 295                 300

Phe Ser Gly Gly Pro Val Ser Phe Pro Leu Ala Pro Gly Pro His Phe
305                 310                 315                 320

Gly Thr Pro Gly Tyr Gly Ser Pro His Phe Thr Ala Leu Tyr Ser Ser
                325                 330                 335

Val Pro Phe Pro Glu Gly Glu Ala Phe Pro Pro Val Ser Val Thr Thr
            340                 345                 350

Leu Gly Ser Pro Met His Ser Asn
        355                 360

<210> SEQ ID NO 2
<211> LENGTH: 317
<212> TYPE: PRT
<213> ORGANISM: Homo sapiens

<400> SEQUENCE: 2

Met Tyr Asn Met Met Glu Thr Glu Leu Lys Pro Pro Gly Pro Gln Gln
1               5                   10                  15

Thr Ser Gly Gly Gly Gly Asn Ser Thr Ala Ala Ala Ala Gly Gly
                20                  25                  30

Asn Gln Lys Asn Ser Pro Asp Arg Val Lys Arg Pro Met Asn Ala Phe
            35                  40                  45

Met Val Trp Ser Arg Gly Gln Arg Arg Lys Met Ala Gln Glu Asn Pro
    50                  55                  60

Lys Met His Asn Ser Glu Ile Ser Lys Arg Leu Gly Ala Glu Trp Lys
65                  70                  75                  80

Leu Leu Ser Glu Thr Glu Lys Arg Pro Phe Ile Asp Glu Ala Lys Arg
                85                  90                  95

Leu Arg Ala Leu His Met Lys Glu His Pro Asp Tyr Lys Tyr Arg Pro
            100                 105                 110

Arg Arg Lys Thr Lys Thr Leu Met Lys Lys Asp Lys Tyr Thr Leu Pro
        115                 120                 125

Gly Gly Leu Leu Ala Pro Gly Gly Asn Ser Met Ala Ser Gly Val Gly
    130                 135                 140

Val Gly Ala Gly Leu Gly Ala Gly Val Asn Gln Arg Met Asp Ser Tyr
145                 150                 155                 160

Ala His Met Asn Gly Trp Ser Asn Gly Ser Tyr Ser Met Met Gln Asp
                165                 170                 175

Gln Leu Gly Tyr Pro Gln His Pro Gly Leu Asn Ala His Gly Ala Ala
            180                 185                 190

Gln Met Gln Pro Met His Arg Tyr Asp Val Ser Ala Leu Gln Tyr Asn
        195                 200                 205

Ser Met Thr Ser Ser Gln Thr Tyr Met Asn Gly Ser Pro Thr Tyr Ser
    210                 215                 220

Met Ser Tyr Ser Gln Gln Gly Thr Pro Gly Met Ala Leu Gly Ser Met
225                 230                 235                 240

Gly Ser Val Val Lys Ser Glu Ala Ser Ser Ser Pro Pro Val Val Thr
                245                 250                 255

Ser Ser Ser His Ser Arg Ala Pro Cys Gln Ala Gly Asp Leu Arg Asp
```

```
                   260                 265                 270
Met Ile Ser Met Tyr Leu Pro Gly Ala Glu Val Pro Glu Pro Ala Ala
                275                 280                 285

Pro Ser Arg Leu His Met Ser Gln His Tyr Gln Ser Gly Pro Val Pro
            290                 295                 300

Gly Thr Ala Ile Asn Gly Thr Leu Pro Leu Ser His Met
305                 310                 315

<210> SEQ ID NO 3
<211> LENGTH: 513
<212> TYPE: PRT
<213> ORGANISM: Homo sapiens

<400> SEQUENCE: 3

Met Arg Gln Pro Pro Gly Glu Ser Asp Met Ala Val Ser Asp Ala Leu
1               5                   10                  15

Leu Pro Ser Phe Ser Thr Phe Ala Ser Gly Pro Ala Gly Arg Glu Lys
                20                  25                  30

Thr Leu Arg Gln Ala Gly Ala Pro Asn Asn Arg Trp Arg Glu Glu Leu
            35                  40                  45

Ser His Met Lys Arg Leu Pro Pro Val Leu Pro Gly Arg Pro Tyr Asp
        50                  55                  60

Leu Ala Ala Ala Thr Val Ala Thr Asp Leu Glu Ser Gly Gly Ala Gly
65                  70                  75                  80

Ala Ala Cys Gly Gly Ser Asn Leu Ala Pro Leu Pro Arg Arg Glu Thr
                85                  90                  95

Glu Glu Phe Asn Asp Leu Leu Asp Leu Asp Phe Ile Leu Ser Asn Ser
            100                 105                 110

Leu Thr His Pro Pro Glu Ser Val Ala Ala Thr Val Ser Ser Ser Ala
        115                 120                 125

Ser Ala Ser Ser Ser Ser Ser Pro Ser Ser Gly Pro Ala Ser Ala
130                 135                 140

Pro Ser Thr Cys Ser Phe Thr Tyr Pro Ile Arg Ala Gly Asn Asp Pro
145                 150                 155                 160

Gly Val Ala Pro Gly Gly Thr Gly Gly Gly Leu Leu Tyr Gly Arg Glu
                165                 170                 175

Ser Ala Pro Pro Pro Thr Ala Pro Phe Asn Leu Ala Asp Ile Asn Asp
            180                 185                 190

Val Ser Pro Ser Gly Gly Phe Val Ala Glu Leu Leu Arg Pro Glu Leu
        195                 200                 205

Asp Pro Val Tyr Ile Pro Pro Gln Gln Pro Gln Pro Pro Gly Gly Gly
    210                 215                 220

Leu Met Gly Lys Phe Val Leu Lys Ala Ser Leu Ser Ala Pro Gly Ser
225                 230                 235                 240

Glu Tyr Gly Ser Pro Ser Val Ile Ser Val Ser Lys Gly Ser Pro Asp
                245                 250                 255

Gly Ser His Pro Val Val Val Ala Pro Tyr Asn Gly Gly Pro Pro Arg
            260                 265                 270

Thr Cys Pro Lys Ile Lys Gln Glu Ala Val Ser Ser Cys Thr His Leu
        275                 280                 285

Gly Ala Gly Pro Pro Leu Ser Asn Gly His Arg Pro Ala Ala His Asp
    290                 295                 300

Phe Pro Leu Gly Arg Gln Leu Pro Ser Arg Thr Thr Pro Thr Leu Gly
305                 310                 315                 320
```

```
Leu Glu Glu Val Leu Ser Ser Arg Asp Cys His Pro Ala Leu Pro Leu
                325                 330                 335

Pro Pro Gly Phe His Pro His Pro Gly Pro Asn Tyr Pro Ser Phe Leu
            340                 345                 350

Pro Asp Gln Met Gln Pro Gln Val Pro Pro Leu His Tyr Gln Gly Gln
                355                 360                 365

Ser Arg Gly Phe Val Ala Arg Ala Gly Glu Pro Cys Val Cys Trp Pro
        370                 375                 380

His Phe Gly Thr His Gly Met Met Leu Thr Pro Ser Ser Pro Leu
385                 390                 395                 400

Glu Leu Met Pro Pro Gly Ser Cys Met Pro Glu Glu Pro Lys Pro Lys
                405                 410                 415

Arg Gly Arg Arg Ser Trp Pro Arg Lys Arg Thr Ala Thr His Thr Cys
            420                 425                 430

Asp Tyr Ala Gly Cys Gly Lys Thr Tyr Thr Lys Ser Ser His Leu Lys
        435                 440                 445

Ala His Leu Arg Thr His Thr Gly Glu Lys Pro Tyr His Cys Asp Trp
    450                 455                 460

Asp Gly Cys Gly Trp Lys Phe Ala Arg Ser Asp Glu Leu Thr Arg His
465                 470                 475                 480

Tyr Arg Lys His Thr Gly His Arg Pro Phe Gln Cys Gln Lys Cys Asp
                485                 490                 495

Arg Ala Phe Ser Arg Ser Asp His Leu Ala Leu His Met Lys Arg His
            500                 505                 510

Phe

<210> SEQ ID NO 4
<211> LENGTH: 439
<212> TYPE: PRT
<213> ORGANISM: Homo sapiens

<400> SEQUENCE: 4

Met Pro Leu Asn Val Ser Phe Thr Asn Arg Asn Tyr Asp Leu Asp Tyr
1               5                   10                  15

Asp Ser Val Gln Pro Tyr Phe Tyr Cys Asp Glu Glu Asn Phe Tyr
                20                  25                  30

Gln Gln Gln Gln Gln Ser Glu Leu Gln Pro Pro Ala Pro Ser Glu Asp
            35                  40                  45

Ile Trp Lys Lys Phe Glu Leu Leu Pro Thr Pro Pro Leu Ser Pro Ser
    50                  55                  60

Arg Arg Ser Gly Leu Cys Ser Pro Ser Tyr Val Ala Val Thr Pro Phe
65                  70                  75                  80

Ser Leu Arg Gly Asp Asn Asp Gly Gly Gly Ser Phe Ser Thr Ala
                85                  90                  95

Asp Gln Leu Glu Met Val Thr Glu Leu Leu Gly Gly Asp Met Val Asn
            100                 105                 110

Gln Ser Phe Ile Cys Asp Pro Asp Asp Glu Thr Phe Ile Lys Asn Ile
    115                 120                 125

Ile Ile Gln Asp Cys Met Trp Ser Gly Phe Ser Ala Ala Ala Lys Leu
    130                 135                 140

Val Ser Glu Lys Leu Ala Ser Tyr Gln Ala Ala Arg Lys Asp Ser Gly
145                 150                 155                 160

Ser Pro Asn Pro Ala Arg Gly His Ser Val Cys Ser Thr Ser Ser Leu
                165                 170                 175
```

```
Tyr Leu Gln Asp Leu Ser Ala Ala Ser Glu Cys Ile Asp Pro Ser
                180                 185                 190

Val Val Phe Pro Tyr Pro Leu Asn Asp Ser Ser Pro Lys Ser Cys
            195                 200                 205

Ala Ser Gln Asp Ser Ser Ala Phe Ser Pro Ser Ser Asp Ser Leu Leu
    210                 215                 220

Ser Ser Thr Glu Ser Ser Pro Gln Gly Ser Pro Glu Pro Leu Val Leu
225                 230                 235                 240

His Glu Glu Thr Pro Pro Thr Thr Ser Ser Asp Ser Glu Glu Glu Gln
                245                 250                 255

Glu Asp Glu Glu Glu Ile Asp Val Val Ser Val Glu Lys Arg Gln Ala
            260                 265                 270

Pro Gly Lys Arg Ser Glu Ser Gly Ser Pro Ser Ala Gly Gly His Ser
        275                 280                 285

Lys Pro Pro His Ser Pro Leu Val Leu Lys Arg Cys His Val Ser Thr
        290                 295                 300

His Gln His Asn Tyr Ala Ala Pro Pro Ser Thr Arg Lys Asp Tyr Pro
305                 310                 315                 320

Ala Ala Lys Arg Val Lys Leu Asp Ser Val Arg Val Leu Arg Gln Ile
                325                 330                 335

Ser Asn Asn Arg Lys Cys Thr Ser Pro Arg Ser Ser Asp Thr Glu Glu
            340                 345                 350

Asn Val Lys Arg Arg Thr His Asn Val Leu Glu Arg Gln Arg Arg Asn
        355                 360                 365

Glu Leu Lys Arg Ser Phe Phe Ala Leu Arg Asp Gln Ile Pro Glu Leu
        370                 375                 380

Glu Asn Asn Glu Lys Ala Pro Lys Val Val Ile Leu Lys Lys Ala Thr
385                 390                 395                 400

Ala Tyr Ile Leu Ser Val Gln Ala Glu Glu Gln Lys Leu Ile Ser Glu
                405                 410                 415

Glu Asp Leu Leu Arg Lys Arg Arg Glu Gln Leu Lys His Lys Leu Glu
            420                 425                 430

Gln Leu Arg Asn Ser Cys Ala
        435

<210> SEQ ID NO 5
<211> LENGTH: 571
<212> TYPE: PRT
<213> ORGANISM: Homo sapiens

<400> SEQUENCE: 5

Met Ala Leu Pro Arg Pro Ser Glu Ala Val Pro Gln Asp Lys Val Cys
1               5                   10                  15

Tyr Pro Pro Glu Ser Ser Pro Gln Asn Leu Ala Ala Tyr Tyr Thr Pro
                20                  25                  30

Phe Pro Ser Tyr Gly His Tyr Arg Asn Ser Leu Ala Thr Val Glu Glu
            35                  40                  45

Asp Phe Gln Pro Phe Arg Gln Leu Glu Ala Ala Ala Ser Ala Ala Pro
    50                  55                  60

Ala Met Pro Pro Phe Pro Phe Arg Met Ala Pro Pro Leu Leu Ser Pro
65                  70                  75                  80

Gly Leu Gly Leu Gln Arg Glu Pro Leu Tyr Asp Leu Pro Trp Tyr Ser
                85                  90                  95

Lys Leu Pro Pro Trp Tyr Pro Ile Pro His Val Pro Arg Glu Val Pro
                100                 105                 110
```

```
Pro Phe Leu Ser Ser His Glu Tyr Ala Gly Ala Ser Ser Glu Asp
        115                 120                 125

Leu Gly His Gln Ile Ile Gly Asp Asn Glu Ser Gly Pro Cys Cys
130                 135                 140

Gly Pro Asp Thr Leu Ile Pro Pro Pro Ala Asp Ala Ser Leu Leu
145                 150                 155                 160

Pro Glu Gly Leu Arg Thr Ser Gln Leu Leu Pro Cys Ser Pro Ser Lys
                165                 170                 175

Gln Ser Glu Asp Gly Pro Lys Pro Ser Asn Gln Glu Gly Lys Ser Pro
                180                 185                 190

Ala Arg Phe Gln Phe Thr Glu Asp Leu His Phe Val Leu Tyr Gly
                195                 200                 205

Val Thr Pro Ser Leu Glu His Pro Ala Ser Leu His His Ala Ile Ser
    210                 215                 220

Gly Leu Leu Val Pro Pro Asp Ser Ser Gly Ser Asp Ser Leu Pro Gln
225                 230                 235                 240

Thr Leu Asp Lys Asp Ser Leu Gln Leu Pro Glu Gly Leu Cys Leu Met
                245                 250                 255

Gln Thr Val Phe Gly Glu Val Pro His Phe Gly Val Phe Cys Ser Ser
            260                 265                 270

Phe Ile Ala Lys Gly Val Arg Phe Gly Pro Phe Gln Gly Lys Val Val
        275                 280                 285

Asn Ala Ser Glu Val Lys Thr Tyr Gly Asp Asn Ser Val Met Trp Glu
    290                 295                 300

Ile Phe Glu Asp Gly His Leu Ser His Phe Ile Asp Gly Lys Gly Gly
305                 310                 315                 320

Thr Gly Asn Trp Met Ser Tyr Val Asn Cys Ala Arg Phe Pro Lys Glu
                325                 330                 335

Gln Asn Leu Val Ala Val Gln Cys Gln Gly His Ile Phe Tyr Glu Ser
            340                 345                 350

Cys Lys Glu Ile His Gln Asn Gln Glu Leu Leu Val Trp Tyr Gly Asp
        355                 360                 365

Cys Tyr Glu Lys Phe Leu Asp Ile Pro Val Ser Leu Gln Val Thr Glu
    370                 375                 380

Pro Gly Lys Gln Pro Ser Gly Pro Ser Glu Glu Ser Ala Glu Gly Tyr
385                 390                 395                 400

Arg Cys Glu Arg Cys Gly Lys Val Phe Thr Tyr Lys Tyr Tyr Arg Asp
                405                 410                 415

Lys His Leu Lys Tyr Thr Pro Cys Val Asp Lys Gly Asp Arg Lys Phe
            420                 425                 430

Pro Cys Ser Leu Cys Lys Arg Ser Phe Glu Lys Arg Asp Arg Leu Arg
        435                 440                 445

Ile His Ile Leu His Val His Glu Lys His Arg Pro His Lys Cys Ser
450                 455                 460

Thr Cys Gly Lys Cys Phe Ser Gln Ser Ser Ser Leu Asn Lys His Met
465                 470                 475                 480

Arg Val His Ser Gly Asp Arg Pro Tyr Gln Cys Val Tyr Cys Thr Lys
                485                 490                 495

Arg Phe Thr Ala Ser Ser Ile Leu Arg Thr His Ile Arg Gln His Ser
            500                 505                 510

Gly Glu Lys Pro Phe Lys Cys Lys Tyr Cys Gly Lys Ser Phe Ala Ser
        515                 520                 525
```

```
His Ala Ala His Asp Ser His Val Arg Arg Ser His Lys Glu Asp Asp
            530                 535                 540

Gly Cys Ser Cys Ser Ile Cys Gly Lys Ile Phe Ser Asp Gln Glu Thr
545                 550                 555                 560

Phe Tyr Ser His Met Lys Phe His Glu Asp Tyr
                565                 570

<210> SEQ ID NO 6
<211> LENGTH: 1299
<212> TYPE: PRT
<213> ORGANISM: Homo sapiens

<400> SEQUENCE: 6

Met Asp Ser Leu Asp His Met Leu Thr Asp Pro Leu Glu Leu Gly Pro
1               5                   10                  15

Cys Gly Asp Gly His Gly Thr Arg Ile Met Glu Asp Cys Leu Leu Gly
            20                  25                  30

Gly Thr Arg Val Ser Leu Pro Glu Asp Leu Leu Glu Asp Pro Glu Ile
        35                  40                  45

Phe Phe Asp Val Val Ser Leu Ser Thr Trp Gln Glu Val Leu Ser Asp
50                  55                  60

Ser Gln Arg Glu His Leu Gln Gln Phe Leu Pro Gln Phe Pro Glu Asp
65                  70                  75                  80

Ser Ala Glu Gln Gln Asn Glu Leu Ile Leu Ala Leu Phe Ser Gly Glu
                85                  90                  95

Asn Phe Arg Phe Gly Asn Pro Leu His Ile Ala Gln Lys Leu Phe Arg
            100                 105                 110

Asp Gly His Phe Asn Pro Glu Val Val Lys Tyr Arg Gln Leu Cys Phe
        115                 120                 125

Lys Ser Gln Tyr Lys Arg Tyr Leu Asn Ser Gln Gln Tyr Phe His
130                 135                 140

Arg Leu Leu Lys Gln Ile Leu Ala Ser Arg Ser Asp Leu Leu Glu Met
145                 150                 155                 160

Ala Arg Arg Ser Gly Pro Ala Leu Pro Phe Arg Gln Lys Arg Pro Ser
                165                 170                 175

Pro Ser Arg Thr Pro Glu Glu Arg Glu Trp Arg Thr Gln Gln Arg Tyr
            180                 185                 190

Leu Lys Val Leu Arg Glu Val Lys Glu Glu Cys Gly Asp Thr Ala Leu
        195                 200                 205

Ser Ser Asp Glu Glu Asp Leu Ser Ser Trp Leu Pro Ser Ser Pro Ala
210                 215                 220

Arg Ser Pro Ser Pro Ala Val Pro Leu Arg Val Val Pro Thr Leu Ser
225                 230                 235                 240

Thr Thr Asp Met Lys Thr Ala Asp Lys Val Glu Leu Gly Asp Ser Asp
                245                 250                 255

Leu Lys Ile Met Leu Lys Lys His His Glu Lys Arg Lys His Gln Pro
            260                 265                 270

Asp His Pro Asp Leu Leu Thr Gly Asp Leu Thr Leu Asn Asp Ile Met
        275                 280                 285

Thr Arg Val Asn Ala Gly Arg Lys Gly Ser Leu Ala Ala Leu Tyr Asp
290                 295                 300

Leu Ala Val Leu Lys Lys Val Lys Glu Glu Lys Lys
305                 310                 315                 320

Lys Lys Ile Lys Thr Ile Lys Ser Glu Ala Glu Asp Leu Ala Glu Pro
                325                 330                 335
```

```
Leu Ser Ser Thr Glu Gly Val Ala Pro Leu Ser Gln Ala Pro Ser Pro
            340                 345                 350

Leu Ala Ile Pro Ala Ile Lys Glu Pro Leu Glu Asp Leu Lys Pro
            355                 360                 365

Cys Leu Gly Ile Asn Glu Ile Ser Ser Phe Phe Ser Leu Leu Leu
        370                 375                 380

Glu Ile Leu Leu Leu Glu Ser Gln Ala Ser Leu Pro Met Leu Glu Glu
385                 390                 395                 400

Arg Val Leu Asp Trp Gln Ser Ser Pro Ala Ser Ser Leu Asn Ser Trp
                405                 410                 415

Phe Ser Ala Ala Pro Asn Trp Ala Glu Leu Val Leu Pro Ala Leu Gln
            420                 425                 430

Tyr Leu Ala Gly Glu Ser Arg Ala Val Pro Ser Ser Phe Ser Pro Phe
            435                 440                 445

Val Glu Phe Lys Glu Lys Thr Gln Gln Trp Lys Leu Leu Gly Gln Ser
            450                 455                 460

Gln Asp Asn Glu Lys Glu Leu Ala Ala Leu Phe Gln Leu Trp Leu Glu
465                 470                 475                 480

Thr Lys Asp Gln Ala Phe Cys Lys Gln Glu Asn Glu Asp Ser Ser Asp
                485                 490                 495

Ala Thr Thr Pro Val Pro Arg Val Arg Thr Asp Tyr Val Val Arg Pro
            500                 505                 510

Ser Thr Gly Glu Glu Lys Arg Val Phe Gln Glu Gln Glu Arg Tyr Arg
            515                 520                 525

Tyr Ser Gln Pro His Lys Ala Phe Thr Phe Arg Met His Gly Phe Glu
            530                 535                 540

Ser Val Val Gly Pro Val Lys Gly Val Phe Asp Lys Glu Thr Ser Leu
545                 550                 555                 560

Asn Lys Ala Arg Glu His Ser Leu Leu Arg Ser Asp Arg Pro Ala Tyr
                565                 570                 575

Val Thr Ile Leu Ser Leu Val Arg Asp Ala Ala Arg Leu Pro Asn
            580                 585                 590

Gly Glu Gly Thr Arg Ala Glu Ile Cys Glu Leu Leu Lys Asp Ser Gln
                595                 600                 605

Phe Leu Ala Pro Asp Val Thr Ser Thr Gln Val Asn Thr Val Val Ser
            610                 615                 620

Gly Ala Leu Asp Arg Leu His Tyr Glu Lys Asp Pro Cys Val Lys Tyr
625                 630                 635                 640

Asp Ile Gly Arg Lys Leu Trp Ile Tyr Leu His Arg Asp Arg Ser Glu
                645                 650                 655

Glu Glu Phe Glu Arg Ile His Gln Ala Gln Ala Ala Ala Lys Ala
            660                 665                 670

Arg Lys Ala Leu Gln Gln Lys Pro Lys Pro Pro Ser Lys Val Lys Ser
            675                 680                 685

Ser Ser Lys Glu Ser Ser Ile Lys Val Leu Ser Ser Gly Pro Ser Glu
            690                 695                 700

Gln Ser Gln Met Ser Leu Ser Asp Ser Ser Met Pro Pro Thr Pro Val
705                 710                 715                 720

Thr Pro Val Thr Pro Thr Thr Pro Ala Leu Pro Ala Ile Pro Ile Ser
                725                 730                 735

Pro Pro Pro Val Ser Ala Val Asn Lys Ser Gly Pro Ser Thr Val Ser
            740                 745                 750
```

-continued

```
Glu Pro Ala Lys Ser Ser Gly Val Leu Val Ser Pro Thr
    755             760             765
Met Pro His Leu Gly Thr Met Leu Ser Pro Ala Ser Ser Gln Thr Ala
    770             775             780
Pro Ser Ser Gln Ala Ala Arg Val Val Ser His Ser Gly Ser Ala
785             790             795             800
Gly Leu Ser Gln Val Arg Val Ala Gln Pro Ser Leu Pro Ala Val
                805             810             815
Pro Gln Gln Ser Gly Gly Pro Ala Gln Thr Leu Pro Gln Met Pro Ala
                820             825             830
Gly Pro Gln Ile Arg Val Pro Ala Thr Ala Thr Gln Thr Lys Val Val
                835             840             845
Pro Gln Thr Val Met Ala Thr Val Pro Val Lys Ala Gln Thr Thr Ala
                850             855             860
Ala Thr Val Gln Arg Pro Gly Pro Gly Gln Thr Gly Leu Thr Val Thr
865             870             875             880
Ser Leu Pro Ala Thr Ala Ser Pro Val Ser Lys Pro Ala Thr Ser Ser
                885             890             895
Pro Gly Thr Ser Ala Pro Ser Ala Ser Thr Ala Ala Val Ile Gln Asn
                900             905             910
Val Thr Gly Gln Asn Ile Ile Lys Gln Val Ala Ile Thr Gly Gln Leu
                915             920             925
Gly Val Lys Pro Gln Thr Gly Asn Ser Ile Pro Leu Thr Ala Thr Asn
                930             935             940
Phe Arg Ile Gln Gly Lys Asp Val Leu Arg Leu Pro Pro Ser Ser Ile
945             950             955             960
Thr Thr Asp Ala Lys Gly Gln Thr Val Leu Arg Ile Thr Pro Asp Met
                965             970             975
Met Ala Thr Leu Ala Lys Ser Gln Val Thr Thr Val Lys Leu Thr Gln
                980             985             990
Asp Leu Phe Gly Thr Gly Gly Asn Thr Thr Gly Lys Gly Ile Ser Ala
                995             1000            1005
Thr Leu His Val Thr Ser Asn Pro Val His Ala Ala Asp Ser Pro
    1010            1015            1020
Ala Lys Ala Ser Ser Ala Ser Ala Pro Ser Ser Thr Pro Thr Gly
    1025            1030            1035
Thr Thr Val Val Lys Val Thr Pro Asp Leu Lys Pro Thr Glu Ala
    1040            1045            1050
Ser Ser Ser Ala Phe Arg Leu Met Pro Ala Leu Gly Val Ser Val
    1055            1060            1065
Ala Asp Gln Lys Gly Lys Ser Thr Val Ala Ser Ser Glu Ala Lys
    1070            1075            1080
Pro Ala Ala Thr Ile Arg Ile Val Gln Gly Leu Gly Val Met Pro
    1085            1090            1095
Pro Lys Ala Gly Gln Thr Ile Thr Val Ala Thr His Ala Lys Gln
    1100            1105            1110
Gly Ala Ser Val Ala Ser Gly Ser Gly Thr Val His Thr Ser Ala
    1115            1120            1125
Val Ser Leu Pro Ser Met Asn Ala Ala Val Ser Lys Thr Val Ala
    1130            1135            1140
Val Ala Ser Gly Ala Ala Ser Thr Pro Ile Ser Ile Ser Thr Gly
    1145            1150            1155
Ala Pro Thr Val Arg Gln Val Pro Val Ser Thr Thr Val Val Ser
```

-continued

```
              1160                1165                1170

Thr Ser  Gln Ala Gly Lys Leu Pro Thr Arg Ile Thr  Val Pro Leu
    1175             1180                1185

Ser Val  Ile Ser Gln Pro Met Lys Gly Lys Ser Val  Val Thr Ala
    1190             1195                1200

Pro Ile  Ile Lys Gly Asn Leu Gly Ala Asn Leu Ser  Gly Leu Gly
    1205             1210                1215

Arg Asn  Ile Ile Leu Thr Thr Met Pro Ala Gly Thr  Lys Leu Ile
    1220             1225                1230

Ala Gly  Asn Lys Pro Val Ser Phe Leu Thr Ala Gln  Gln Leu Gln
    1235             1240                1245

Gln Leu  Gln Gln Gln Gly Gln Ala Thr Gln Val Arg  Ile Gln Thr
    1250             1255                1260

Val Pro  Ala Ser His Leu Gln Gln Gly Thr Ala Ser  Gly Ser Ser
    1265             1270                1275

Lys Ala  Val Ser Thr Val Val Thr Thr Ala Pro Ser  Pro Lys
    1280             1285                1290

Gln Ala  Pro Glu Gln Gln
    1295

<210> SEQ ID NO 7
<211> LENGTH: 27
<212> TYPE: DNA
<213> ORGANISM: artificial
<220> FEATURE:
<223> OTHER INFORMATION: synthetic

<400> SEQUENCE: 7
atttgttttt tgggtagtta aaggttg                                       27

<210> SEQ ID NO 8
<211> LENGTH: 29
<212> TYPE: DNA
<213> ORGANISM: artificial
<220> FEATURE:
<223> OTHER INFORMATION: synthetic

<400> SEQUENCE: 8
accaactatc ttcatcttaa taacatcca                                     29

<210> SEQ ID NO 9
<211> LENGTH: 25
<212> TYPE: DNA
<213> ORGANISM: artificial
<220> FEATURE:
<223> OTHER INFORMATION: synthetic

<400> SEQUENCE: 9
tggttaggtt ggttttaaat ttttg                                         25

<210> SEQ ID NO 10
<211> LENGTH: 26
<212> TYPE: DNA
<213> ORGANISM: artificial
<220> FEATURE:
<223> OTHER INFORMATION: synthetic

<400> SEQUENCE: 10
aacccaccct tataaattct caatta                                        26

<210> SEQ ID NO 11
```

```
<211> LENGTH: 24
<212> TYPE: DNA
<213> ORGANISM: artificial
<220> FEATURE:
<223> OTHER INFORMATION: synthetic

<400> SEQUENCE: 11
gacggcatcg cagcttggat acac                                          24

<210> SEQ ID NO 12
<211> LENGTH: 25
<212> TYPE: DNA
<213> ORGANISM: artificial
<220> FEATURE:
<223> OTHER INFORMATION: synthetic

<400> SEQUENCE: 12
tcgtagagag gctccctctg taggc                                         25

<210> SEQ ID NO 13
<211> LENGTH: 22
<212> TYPE: DNA
<213> ORGANISM: artificial
<220> FEATURE:
<223> OTHER INFORMATION: synthetic

<400> SEQUENCE: 13
caggtccgag gatcaaccca gc                                            22

<210> SEQ ID NO 14
<211> LENGTH: 22
<212> TYPE: DNA
<213> ORGANISM: artificial
<220> FEATURE:
<223> OTHER INFORMATION: synthetic

<400> SEQUENCE: 14
gggttctcct gggccatctt gc                                            22

<210> SEQ ID NO 15
<211> LENGTH: 20
<212> TYPE: DNA
<213> ORGANISM: artificial
<220> FEATURE:
<223> OTHER INFORMATION: synthetic

<400> SEQUENCE: 15
tcccgccagc ggttattcgg                                               20

<210> SEQ ID NO 16
<211> LENGTH: 25
<212> TYPE: DNA
<213> ORGANISM: artificial
<220> FEATURE:
<223> OTHER INFORMATION: synthetic

<400> SEQUENCE: 16
cctcctcgtc gcagtagaaa tacgg                                         25

<210> SEQ ID NO 17
<211> LENGTH: 25
<212> TYPE: DNA
<213> ORGANISM: artificial
<220> FEATURE:
<223> OTHER INFORMATION: synthetic

<400> SEQUENCE: 17
```

```
gcagaaactg ctggaggtgt tcacg                                          25

<210> SEQ ID NO 18
<211> LENGTH: 50
<212> TYPE: DNA
<213> ORGANISM: artificial
<220> FEATURE:
<223> OTHER INFORMATION: synthetic

<400> SEQUENCE: 18
cagctctaac cctaaacaag tgctcaaccc ttgaatgggc ctggatggct               50

<210> SEQ ID NO 19
<211> LENGTH: 50
<212> TYPE: DNA
<213> ORGANISM: artificial
<220> FEATURE:
<223> OTHER INFORMATION: synthetic

<400> SEQUENCE: 19
catttttaac cctaaacaag tttttaaccc ttgaatgggc ctggatggct               50
```